United States Patent
Ma

(10) Patent No.: US 7,317,192 B2
(45) Date of Patent: Jan. 8, 2008

(54) HIGH ENERGY POLYENERGETIC ION SELECTION SYSTEMS, ION BEAM THERAPY SYSTEMS, AND ION BEAM TREATMENT CENTERS

(75) Inventor: Chang-Ming Charlie Ma, Huntingdon Valley, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 0 days.

(21) Appl. No.: 10/559,058

(22) PCT Filed: Jun. 2, 2004

(86) PCT No.: PCT/US2004/017081

§ 371 (c)(1),
(2), (4) Date: Dec. 1, 2005

(87) PCT Pub. No.: WO2004/109717

PCT Pub. Date: Dec. 16, 2004

(65) Prior Publication Data

US 2006/0145088 A1    Jul. 6, 2006

Related U.S. Application Data

(60) Provisional application No. 60/475,027, filed on Jun. 2, 2003.

(51) Int. Cl.
  *H01J 1/50*      (2006.01)
  *H01J 3/00*      (2006.01)
  *G21G 5/00*      (2006.01)
(52) U.S. Cl. ............................. 250/396 ML; 250/298; 250/400; 250/492.1; 250/492.3

(58) Field of Classification Search ........ 250/396 ML, 250/298
See application file for complete search history.

(56) References Cited

U.S. PATENT DOCUMENTS 3,555,332 A    1/1971    Schroder et al. .............. 313/63
3,786,359 A    1/1974    King .......................... 328/233

(Continued)

FOREIGN PATENT DOCUMENTS

CA         2335071 A1    10/2000

(Continued)

OTHER PUBLICATIONS

Bonlie, J., et al., "Production of>$10^{21}$ W/cm$^2$ from a large aperture Ti:sapphire laser system," *Appl. Phys. B*, 2000, 70[Suppl.], S155-S160.

(Continued)

*Primary Examiner*—Robert Kim
*Assistant Examiner*—Bernard Souw
(74) *Attorney, Agent, or Firm*—Woodcock Washburn LLP

(57) ABSTRACT

Devices and methods are provided for generating laser-accelerated high energy polyenergetic positive ion beams that are spatially separated and modulated based on energy level. The spatially separated and modulated high energy polyenergetic positive ion beams are used for radiation therapy. In addition, methods are provided for treating patients in radiation treatment centers using therapeutically suitable high energy polyenergetic positive ion beams that are provided by spatially separating and modulating positive ion beams. The production of radioisotopes using spatially separated and modulated laser-accelerated high energy polyenergetic positive ion beams is also provided.

60 Claims, 51 Drawing Sheets

U.S. PATENT DOCUMENTS

| | | | |
|---|---|---|---|
| 4,022,927 A * | 5/1977 | Pfeiffer et al. | 430/5 |
| 4,069,457 A | 1/1978 | Martin et al. | 315/503 |
| 4,297,191 A | 10/1981 | Chen | 204/193 |
| 4,344,019 A | 8/1982 | Gavin et al. | 315/111.81 |
| 4,529,571 A | 7/1985 | Bacon et al. | 376/144 |
| 4,715,038 A | 12/1987 | Fraser et al. | 372/2 |
| 4,870,287 A | 9/1989 | Cole et al. | 250/492.3 |
| 4,937,532 A | 6/1990 | Dawson et al. | 359/342 |
| 5,175,755 A | 12/1992 | Kumakhov | 378/34 |
| 5,192,869 A | 3/1993 | Kumakhov | 250/505.1 |
| 5,235,606 A | 8/1993 | Mourou et al. | 375/25 |
| 5,317,616 A | 5/1994 | Swerdloff et al. | 378/65 |
| 5,335,258 A | 8/1994 | Whitlock | 378/122 |
| 5,382,914 A | 1/1995 | Hamm et al. | 315/505 |
| 5,394,411 A | 2/1995 | Milchberg et al. | 372/5 |
| 5,394,452 A | 2/1995 | Swerdloff et al. | 378/65 |
| 5,412,283 A | 5/1995 | Tronc | 315/5.41 |
| 5,438,454 A | 8/1995 | Ludewigt et al. | 359/641 |
| 5,440,133 A | 8/1995 | Moyers et al. | 250/492.3 |
| 5,442,675 A | 8/1995 | Swerdloff et al. | 378/65 |
| 5,497,008 A | 3/1996 | Kumakhov | 250/505.1 |
| 5,528,650 A | 6/1996 | Swerdloff et al. | 378/65 |
| 5,548,627 A | 8/1996 | Swerdloff et al. | 378/4 |
| 5,625,663 A | 4/1997 | Swerdloff et al. | 378/65 |
| 5,637,966 A | 6/1997 | Umstadter et al. | 315/507 |
| 5,661,773 A | 8/1997 | Swerdloff et al. | 378/65 |
| 5,668,371 A | 9/1997 | Deasy et al. | 350/306 |
| 5,673,300 A | 9/1997 | Reckwerdt et al. | 378/65 |
| 5,724,400 A | 3/1998 | Swerdloff et al. | 378/65 |
| 5,789,876 A | 8/1998 | Umstadter et al. | 315/507 |
| 5,930,331 A | 7/1999 | Rentzepis et al. | 378/136 |
| 6,005,250 A * | 12/1999 | Stickel et al. | 250/396 R |
| 6,034,377 A | 3/2000 | Pu | 250/492.3 |
| 6,043,488 A * | 3/2000 | Bahatt et al. | 250/294 |
| 6,057,655 A | 5/2000 | Jongen | 315/502 |
| 6,087,672 A | 7/2000 | Matsuda et al. | 250/505.1 |
| 6,271,529 B1 * | 8/2001 | Farley et al. | 250/492.21 |
| 6,333,966 B1 | 12/2001 | Schoen | 378/119 |
| 6,345,114 B1 | 2/2002 | Mackie et al. | 382/132 |
| 6,385,286 B1 | 5/2002 | Fitchard et al. | 378/65 |
| 6,433,336 B1 | 8/2002 | Jongen et al. | 250/305 |
| 6,438,202 B1 | 8/2002 | Olivera et al. | 378/65 |
| 6,534,764 B1 * | 3/2003 | Verentchikov et al. | 250/287 |
| 6,560,311 B1 | 5/2003 | Shepard et al. | 378/65 |
| 6,617,598 B1 | 9/2003 | Matsuda | 250/492.3 |
| 6,618,467 B1 | 9/2003 | Ruchala et al. | 378/65 |
| 6,636,622 B2 | 10/2003 | Mackie et al. | 382/132 |
| 6,639,234 B1 | 10/2003 | Badura et al. | 250/492.3 |
| 6,642,525 B2 * | 11/2003 | Kienzle et al. | 250/396 ML |
| 6,670,618 B1 | 12/2003 | Hartmann et al. | 250/491.1 |
| 6,680,480 B2 | 1/2004 | Schoen | 250/423 R |
| 6,683,318 B1 | 1/2004 | Haberer et al. | 250/492.3 |
| 6,693,283 B2 * | 2/2004 | Eickhoff et al. | 250/396 ML |
| 6,717,162 B1 | 4/2004 | Jongen | 250/505.1 |
| 6,725,078 B2 | 4/2004 | Bucholz et al. | 600/410 |
| 6,730,921 B2 | 5/2004 | Kraft | 250/492.1 |
| 6,736,831 B1 | 5/2004 | Hartmann et al. | 607/1 |
| 6,745,072 B1 | 6/2004 | Badura et al. | 607/2 |
| 6,777,700 B2 | 8/2004 | Yanagisawa et al. | 250/492.3 |
| 6,780,149 B1 | 8/2004 | Schulte | 600/1 |
| 6,799,068 B1 | 9/2004 | Hartmann et al. | 607/2 |
| 6,852,985 B2 | 2/2005 | Cowan et al. | 250/423 P |
| 6,862,469 B2 | 3/2005 | Bucholz et al. | 600/411 |
| 6,867,419 B2 | 3/2005 | Tajima | 250/423 P |
| 6,873,123 B2 | 3/2005 | Marchand et al. | 315/502 |
| 6,885,014 B2 * | 4/2005 | Benveniste | 250/492.21 |
| 6,897,457 B1 | 5/2005 | Holmes et al. | 250/492.21 |
| 6,906,338 B2 | 6/2005 | Tajima | 250/505.1 |
| 6,909,764 B2 | 6/2005 | Maksimchuk et al. | 376/190 |
| 6,992,308 B2 * | 1/2006 | Graf et al. | 250/492.21 |
| 6,998,625 B1 * | 2/2006 | McKenna et al. | 250/492.21 |
| 7,049,613 B2 * | 5/2006 | Yanagisawa et al. | 250/492.3 |
| 2002/0084422 A1 * | 7/2002 | Kienzle et al. | 250/396 ML |
| 2002/0090194 A1 | 7/2002 | Tajima | 385/147 |
| 2002/0136439 A1 | 9/2002 | Ruchala et al. | 382/131 |
| 2002/0150207 A1 | 10/2002 | Kapatoes et al. | 378/65 |
| 2003/0183774 A1 | 10/2003 | Tajima | 250/423 P |
| 2004/0018700 A1 | 1/2004 | Cowan et al. | 438/513 |
| 2004/0113099 A1 * | 6/2004 | Eickhoff et al. | 250/492.3 |
| 2004/0149934 A1 | 8/2004 | Yanagisawa et al. | 250/492.3 |
| 2004/0173763 A1 | 9/2004 | Moriyama et al. | 250/492.1 |
| 2004/0195951 A1 | 10/2004 | Suk et al. | 313/359.1 |
| 2004/0200983 A1 | 10/2004 | Fujimaki et al. | 250/492.3 |
| 2004/0227104 A1 | 11/2004 | Matsuda et al. | 250/492.1 |
| 2005/0029471 A1 * | 2/2005 | Kraft et al. | 250/492.1 |
| 2005/0051740 A1 | 3/2005 | Yanagisawa et al. | 250/492.1 |
| 2005/0069076 A1 | 3/2005 | Bricault et al. | 376/190 |
| 2005/0087700 A1 | 4/2005 | Tadokoro et al. | 250/492.21 |
| 2005/0099145 A1 | 5/2005 | Nishiuchi et al. | 315/500 |
| 2005/0127306 A1 * | 6/2005 | Yanagisawa et al. | 250/492.1 |
| 2005/0167616 A1 * | 8/2005 | Yanagisawa et al. | 250/492.22 |
| 2006/0145088 A1 * | 7/2006 | Ma | 250/396 ML |
| 2007/0034812 A1 * | 2/2007 | Ma et al. | 250/492.21 |

FOREIGN PATENT DOCUMENTS

| | | | |
|---|---|---|---|
| DE | | 3616879 A1 | 11/1986 |
| EP | | 0 555 376 B1 | 3/1998 |
| EP | | 0 986 070 A1 | 3/2000 |
| EP | | 0 986 071 A3 | 3/2000 |
| EP | | 1 085 786 A3 | 3/2001 |
| EP | | 1 584 353 A1 | 10/2005 |
| EP | | 1 617 713 A1 | 1/2006 |
| EP | | 1690323 * | 8/2006 |
| GB | | 2 341 301 A | 3/2000 |
| JP | | 06068984 A | 3/1994 |
| JP | | 06154351 A | 6/1994 |
| JP | | 200299075 | 12/2000 |
| JP | | 2000354637 A | 12/2000 |
| JP | | 2001000562 A | 1/2001 |
| JP | | 2001009050 A | 1/2001 |
| JP | | 2001245994 A | 9/2001 |
| WO | | 92/08235 A1 | 5/1992 |
| WO | | 00/16342 A1 | 3/2000 |
| WO | | 00/49624 A1 | 8/2000 |
| WO | | 00/62307 A1 | 10/2000 |
| WO | | 02/063637 A1 | 8/2002 |
| WO | | 02/103392 A1 | 12/2002 |
| WO | | 03/092812 A1 | 11/2003 |
| WO | | 03/101538 A1 | 12/2003 |
| WO | | 2004/053892 A2 | 6/2004 |
| WO | | 2004/109717 A2 | 6/2004 |
| WO | | 2004/101070 A1 | 11/2004 |
| WO | WO 2004/109717 | * | 12/2004 |
| WO | WO 2005/057738 | * | 12/2004 |
| WO | | 2005/018734 A2 | 3/2005 |
| WO | | 2005/018735 A2 | 3/2005 |
| WO | | 2005/057738 A2 | 6/2005 |
| WO | | 03/051201 A2 | 6/2006 |
| WO | WO 2006/086084 | * | 9/2006 |

OTHER PUBLICATIONS

Bortfeld, T., "An analytical approximation of the Bragg curve for therapeutic proton beams," *Med. Phys.*, Dec. 1997, 24(12), 2024-2033.

Cella, L., et al., "Potential role of intensity modulated proton beams in prostate cancer radiotherapy," *Int. J. Radiation Oncology Biol. Phys.*, 2001, 49, 217-223.

Chiu, C. et al., "Laser electron accelerators for radiation medicine: A feasibility study," *Med. Phys.*, Jul. 2004, 31(7), 2042-2052.

Chu, K.C., et al., "Direct measurement of the spectral phase of femtosecond pulses," *Opt. Lett.*, Apr. 15, 1995, 20(8), 904-906.

Deng, J., et al., "Electron beam commissioning for Monte Carlo dose calculation," *Phys. Med. Biol.*, 2000, 3 pages.

Deng, J., et al., "Photon beam characterization and modelling for Monte Carlo treatment planning," *Phys. Med. Biol.*, 2000, 45, 411-427.

Dorchies, F., et al., "Monomode guiding of 1 [16] W/cm$^2$ laser pulses over 100 rayleigh lengths in hollow capillary dielectric tubes," *Phys. Rev. Lett.*, Jun. 7, 1999, 82(23), 4655-4658.

Dunn, J., et al., "X-ray sensitive charge-coupled device instrumentation for short and ultrashort pulse laser-produced plasma experiments," *Rev. Sci. Instrum.*, Jan. 1995, 66, 706-708.

Fisher, D.L., et al., "Enhanced Raman forward scattering," *Phys. Rev. E*, Feb. 1996, 53(2), 1844-1851.

Fourkal, E. et al., "Coulomb explosion effect and the maximum energy of protons accelerated by high-power lasers," *Physical Review E.*, Mar. 2005, 71, 036412-1 to 036412-11.

Fourkal, E. et al., "Particle selection for laser-accelerated proton therapy feasibilty study," *Med. Phys.*, Jul. 2003, 30(7), 1660-1670.

Fuss, M., et al., "Proton radiation therapy (PRT) for pediatric optic pathway gliomas: comparison with 3D planned conventional photons and a standard photon technique," *Int. J. Radiation Oncology Biol. Phys.*, 1999, 45(5) 1117-1126.

Gitomer, S.J., et al., "Fast ions and hot electrons in the laser-plasma interation," *Phys. Fluids*, 1986, 29(8), 2679-2686.

Guethlein, G., et al., "Charge and mass resolved time of flight observations of 140 fs laser produced ions," *Rev. Sci. Instrum.*, Jan. 1995, 66, 333-335.

Guethlein, G., et al., "Electron temperature measurements of solid density plasmas produced by intense ultrashort laser pulses," *Physical Review letters*, Aug. 5, 1996, 77(6), 1055-1058.

Gustafsson, A., et al., "A generalized pencil beam algorithm for optimization of radiation therapy," *Med. Phys.*, Mar. 1994, 21(3), 343-356.

Holmes, T.W., et al., "A filtered backprojection dose calculation method for inverse treatment planning," *Med. Phys.*, Feb. 1994, 21(2), 303-313.

Itatani, J. et al., "Suppression of the amplified spontaneous emission on chirped-pulse-amplification lasers by clean high-energy seed-pulse injection," *Optics Communications*, Mar. 1, 1998, 148, 70-74.

Jiang, S.B., "Development of A Compensator Based Intensity-Modulated Radiation Therapy," *Ph.D. Thesis, Medical College of Ohio*, Toledo, OH, 1998.

Jiang, S.B., et al., "Modeling the extrafocal radiation and monitor chamber backscatter for photon beam dose calculation," *Med. Phys.*, 2001, 28, 55-66.

Jiang, S.B., et al., "Electron beam modeling and commissioning for Monte Carlo treatment planning," *Med. Phys.*, Jan. 2000, 27, 180-191.

Kainz, K. K. et al., "Dose properties of a laser accelerated electron beam and prospects for clinical application," *Med. Phys.*, Jul. 2004, 31(7), 2053-2067.

Kaluza, M. et al., "Influcence of the Laser Prepulse on Proton Acceleration in Thin-Foil Experiments," *Physical Review Letters*, Jul. 23, 2004, 93(4), pp. 045003-1 to 045003-4.

Kapur, A., et al., "Monte Carlo calculations of electron beam output factors for a medical linear accelerator," *Phys. Med. Biol.*, 1998, 43, 3479-3494.

Karlsson, M.G., et al., "Treatment head design for multileaf collimated high-energy electrons," *Med. Phys.*, 1999, 26(10), 2161-2167.

Kohno, R. et al., "Range-modulated pencil beam algorithm for proton dose calculations," *Jpn, J. Appl. Phys.*, 2001, 40, 5187-5193.

Kruer, W.L., et al., "J x B heating by very intense laser light," *Phys. Fluids*, Jan. 1985, 28(1), 430-432.

Lee, M.C., et al., "Monte Carlo and experimental investigation of multileaf collimated electron beams for modulated electron radiotherapy," *Med. Phys.*, Dec. 2000, 27(12), 2708-2718.

Lee, M.C., et al., "Monte Carlo characterization of clinical electron beams in transverse magnetic fields," *Phys. Med. Biol.*, 2000, 45, 2947-2967.

Li, J. S., et al., "Simulation of beam modifiers for Monte Carlo treatment planning," *Proc. ICCR XIIth*, Heldelberg, Germany, 2000, 437-439.

Lomax, A.., "Intensity modulation methods for proton radiotherapy," *Phys. Med. Biol.*, 1999, 44, 185-205.

Ma, C. M. et al., "A Monte Carlo dose calculation tool for radiotherapy treatment planning," *Physics in Medicine & Biology*, 2002, 47, 1671-1689.

Ma., C.-M., et al., "Monitor unit calculation for Monte Carlo treatment planning," *Phys. Med. Biol.*, 2004, 49, 1671-1687.

Ma, C.-M., "Characterization of computer simulated radiotherapy beams for Monte Carlo treatment planning," *Radiation Phys. Chem.*, 1998, 53, 329-344.

Ma, C.-M., et al., "Bragg-Gray theory and ion chamber dosimetry on photon beams," *Phys. Med. Biol.*, 1991, 36(4), 413-428.

Ma, C.-M., et al., "Calulation of absorbed dose ratios using correlated Monte Carlo sampling," *Med. Phys.*, Jul./Aug. 1993, 20(4), 1189-1199.

Ma, C.-M., et al., "Correction factors for water-proofing sleeves in kilovoltage x-ray beams," *Med. Phys.*, Sep. 1997, 24(9), 1057-1513.

Ma, C.-M., et al., "Energy- and intensity-modulated electron beams for radiotherapy," *Phys. Med. Biol.*, 2000, 45, 2293-2311.

Ma, C.-M. et al., "Laser accelerated proton beams for radiation therapy," *Med. Phys.*, Jun. 2001, 28(6), 1236.

Ma, C.-M., et al., "MCDOSE - a Monte Carlo dose calculation tool for radiotherapy treatment planning," *Proc. ICCR XIIth*, Hiedelberg, Germany, 2000, 123-125.

Ma, C.-M., et al., "Monte Carlo modelling of electron beams from medical accerators," *Phys. Med. Biol.*, 1999, 44, R157-R189.

Ma, C.-M., et al., "Monte Carlo verification of IMRT dose distributions from a commercial treatment planning optimization system," *Phys. Med. Biol.*, 2000, 45, 2483-2495.

Ma, C.-M., et al., "Development of a Laser Driven Proton Accelerator for Cancer Therapy," *Laser Physics.*, 2006, 16, 1-8.

Ma, L., et al., "An optimized leaf setting algorithm for beam intensity modulation using dynamic multileaf collimaters," *Phys. Med. Biol.*, 1998, 43, 1629-1643.

Ma. C.-M., et al., "Improvement of small field electron beam dosimetry using Monte Carlo simulation," *Proc. XII Int. Conference on the Use of Computers in Radiation Therapy*, Salt Lake City, USA, 1997, 159-162.

Ma., C.-M., et al., "Accurate characterization of Monte-Carlo calculation electron beams for radiotheapy," *Med. Phys.*, Mar. 1997, 24(3), 401-416.

Ma., C.-M., et al., Calculations of ion chamber displacement effect corrections for medium energy x-ray dosimetry, *Phys. Med. Biol.*, 1995, 40, 45-62.

Ma., C.-M., et al., "Clinical implementation of a Monte Carlo treatment planning system," *Med. Phys.*, Oct. 1999, 26(10), 2133-2143.

Ma., C.-M., et al., "Effect of size and composition on the central electrode on the response of cylindrical ionization chambers in high-energy photon and electron beams," *Phys. Med. Biol.*, 1993, 38, 267-290.

Ma., C.-M., et al., "An investigation of the response of a simple design of plane-parallel chamber," *Phys. Med. Biol.*, 1994, 39, 1593-1608.

Ma., C.-M., et al., "Monte Carlo calculated ion chamber stem effect corrections for medium-energy x-ray dosimetry," *Phys. Med. Biol.*, 1995, 40, 63-72.

Ma., C.-M., et al., "Within the next decade conventional cyclotrons for proton radiotherapy will become obsolete and replaced by far less expensive machines using compat laser systems for the acceleration of the protons," *Med. Phys.*, Mar. 2006, 33(3), 571-573.

Malka, V. et al., "Practicability of protontherapy using compact laser system," *Medical Physics*, Jun. 2004, 31(6), 1587-1592.

Max, C. E., et al., "Image improvement from a sodium-layer laser guide star adaptive optics system at Lick Observatory," *Science*, Sep. 12, 1997, 277, 1649-1652.

Nakajima, K., et al., "Observation of Ultrahigh Gradient Electron Acceleration by a Self-Modulated Intense Short Laser Pulse," *Phys. Rev. Lett.*, May 29, 1995, 74(22), 4428-4431.

Nakamura, T. et al., "Origin of protons accelerated by an intense laser and the dependence of their energy on the plasma density," *Phys. Rev. E. Stat. Nonlin. Soft Matter Physics*, Feb. 2003, 67(2 Pt. 2), 026403-1 to 026403-10.

Nelson, R., et al., "The EGS4 code system, " *Stanford Linear Accelerator Center Report, SLAC-265*, Stanford, CA, 1985.

Patterson, F.G., et al., "Suppression of parasitic lasing in large-aperture Ti:sapphire laser amplifiers," *Opt. Lett.*, Jul. 15, 1999, 24(14), 963-965.

Pawlicki, T., et al., "Monte Carlo Simulation for MLC-based Intensity Modulated Radiotherapy," *Int. J. Radiat. Oncol. Biol. Phys.*, 2000.

Pawlicki, T., et al., "Lens Dose in MLC-Based IMRT Treatments of the Head and Neck," *Int. J. Radiation Oncology Biol. Phys.*, 2004, 59(1), 293-299.

Perry, M.D., et al., "Petawatt laser pulses," *Opt. Lett.*, Feb. 1, 1999, 24(3); 160-162.

Perry, M.D., et al., "Hard x-ray production from high intensity laser solid interactions (invited)," *Rev. Sci. Instr.*, 1999, 70, 265-269.

Perry, M. D. et al., "Terawatt to Petawatt Subpicosecond Lasers," *Science*, May 13, 1994, 264, 917-924.

Price, D.F., et al., "Absorption of ultrashort laser pulses by solid targets heated rapidly to temperatures 1-1000eV," *Phys. Rev. Letts.*, 1995, 75(2), 252-255.

Rau, B., et al., "Spectroscopy of short, intense laser pulses due to gas ionization effects," *J. Opt. Soc. Amer. B*, Mar. 1997, 14(3), 643-649.

Rau, et al., "Strongly nonlinear magnetosonic waves and ion acceleration," *Phys. Plasma*, Oct. 1998, 5(10), 3575-3580.

Roth, M. et al., "Fast ignition by intense laser-accelerated proton beams," *Phys. Rev. Lett.*, Jan. 15, 2001, 86(3), 436-439.

Sentoku, et al., "Bursts of superreflected laser light from inhomogeneous plasmas due to the generation of relativistic solitary waves," *Phys. Rev. Lett.*, Oct. 25, 1999, 83(17), 3434-3437.

Sentoku, Y. et al., "High density collimated beams of relativistic ions produced by petwatt laser pulses in plasmas," *Phys, Rev. E. Stat. Phys. Plasmas Fluids Relat. Interdiscip. Topics*, Nov. 2000, 62(5 Pt B), 7271-7281.

Shahine, B. et al., "Energy Modulation of Laser Accelerated Proton-Beams for Radiation-Therapy," *Med. Phys.*, 2002, 29(6), 1326, (abstract).

Shahine, M.C., et al., "Monte Carlo dose calculation for energy- and intensity-modulated proton therapy," *Med. Phys.*, Jun. 2001, 28(6), (abstract).

Shepherd, R., et al., "Ultrafast x-ray streak camera for use in ultrashort laser-produced plasma research," *Rev. Sci. Instr.*, 1995, 66(1), 719-721.

Shultz, R. J., et al., "On the role of intensity-modulated radiation therapy in radiation oncology," *Med. Phys.*, 2002, 1473-1482.

Siders, C., et al., "Self-starting femtosecond pulse generation from a Ti:sapphire laser synchronously pumped by a pointing-stabilized mode-locked Nd;YAG laser," *Rev. Sci. Instr.*, 1994, 65(10), 3140-3144.

Slater, J., et al., "Conformal proton therapy for prostate carcinoma," *Int. J. Radiation Oncology Biol. Phys.*, 1998, 42(2) 299-304.

Spence, I. et al., "High Intensity laser generation of proton beams for the production of β+ Sources used in positron emission tomography," *AIP Conference Proceedings*, 2001, 584 (Resonance Ionization Spectroscopy 2000), 73-78.

Sullivan, A., et al., "Phase control for production of high-fidelity optical pulses for chirped-pulse amplification," *Opt. Lett.*, 1995, 20(2), 192-194.

Tajima, T., et al., "Laser electron accelerator," *Phys. Rev. Lett.*, Jul. 23, 1979, 43(4), 267-270.

Umstadter, D. et al., "Nonlinear optics in relativistic plasmas and laser wakefield acceleration of electrons," *Science*, 1996, 273, 472-475.

Umstadter, D. et al., "Production of a keV x-ray beam from synchrotron radiation in relativistic laser-plasma interaction," *Phys Rev Lett.* Sep. 24, 2004; 93(13):135005. Epub Sep. 24, 2004.

Vu, B.-T. V., et al., "Temporally and radially-resolved femtosecond optical measurements of solid density plasma reflectivities and transmissivities," *J. Quant. Spectrosc. Radiat. Transfer.*, 1995, 54(1/2), 413-418.

Wielopolski, L. et al., "A novel comprehensive quality control instrument for medical accelerators," *Medical Physics*, Jun. 1995, 22(6), 799-801.

Wilks, S.C. et al., "Energetic proton generation in ultra-intense laser-solid interactions," *Physics of Plasmas*, Feb. 2001, 8(2), 542-549.

Xing, L., et al., "Iterative methods for inverse treatment planning," *Phys, Med. Biol.*, 1996, 41, 2107-2123.

Yeboah, C., et al., "Intensity and energy modulated radiotherapy with proton beams: variables affecting optimal prostate plan," *Med. Phys.*, Feb. 2002, 29(2), 176-189.

Young, B.K.F., et al., "Measurements of x-ray emission and thermal transport in near solid density plasma heated by 130 femtosecond laser pulses," *Phys. Rev E..*, Oct. 1998, 58(4), 4929-4936.

Yu, W., et al., "Electron acceleration by a short relativistic laser pulse at the front of solid targets," *Phys. Rev. Lett.*, Jul. 17, 2000, 85(3), 570-573.

"Proton sources by laser-plasma interaction (LOA/SPL)," Downloaded http://wwwy.ensta.fr/~loa/SPL/protons_gb.html on Mar. 16, 2004, 3 pages.

"New proton treatment offers hope to men with prostate cancer," *KESQ News Channel 3*, CA, May 11, 2005, downloaded at : http://www.kesq.com/global/story.asp?s=3330402&nav=9qrxZjI8 2 pages.

Arrigoni, M. et al., "Terawatt Lasers Raise New Hopes for Radiotherapy," *Biophotonics International*, Jan. 2005, 3 pages.

Baumhacker, H. et al., "Correction of strong phase and amplitude modulations by two deformable mirrors in a multistaged Ti:sapphire laser," *Optics Letters*, Sep. 1, 2002, 27(17), 1570-1572.

Beg, F. N. et al., "Target charging effects on proton acceleration during high-intensity short-pulse laser-solid interactions," *Applied Physics Letters*, Apr. 12, 2004, 84(15), 2766-2768.

Borghesi, M. et al., "Electric field detection in laser-plasma interaction experiments via the proton imaging technique," *Physics of Plasmas*, 2002, 9(5, Pt. 2), 2214-2220 [Abstract Only] 1 page.

Borghesi, M. et al., "Proton imaging: a diagnostic for inertial confinement fusion/fast ignitor studies," *Plasma Physics and Controlled Fusion*, 2001, 43(12A), A267-A276 [Abstract Only] 1 page.

Bortfeld, T. et al., "Proton Beam Radiotherapy - The State of the Art," Abstract No. 4016, *AAPM 47th Annual Meeting*, Jul. 25, 2005, Seattle, Washington; 2 pages.

Brahme, A. et al., 2001, "Development of a Center for Light Ion Therapy and Accurate Tumor Diagnostics at the Karolinska Institute and Hospital," Jul. 30, 2001, at http://lbl.confex.com/lbl/2001/program/abstract_2148.htm.

Breschi, E. et al., "A new algorithm for spectral and spatial reconstruction of proton beams from dosimetric measurements," *Nuclear Instruments and Methods in Physics Research A*, 2004, 522, 190-195.

Bulanov, S.V. et al., "Feasibilty Of Using Laser Ion Accelerators In Proton Therapy," *Plasma Physics Reports*, May 2002, 28(5), 453-456.

Bulanov, S. V. et al., "Laser ion accelerators in oncological hadron-therapy," Feb. 2002, downloaded at http://www.ile.osaka-u.ac.jp/research/TSI/Timur/monoenergetic/ on Sep. 12, 2003.

Bulanov, S. V. et al., "Oncological hadron therapy with laser ion accelerators," *Phys. Lett.*, 2002, 299(2-3), 240-247.

Center for Ultrafast Optical Science (CUOS), at http://www.eecs.umich.edu/USL/ on Sep. 16, 2003, 2 pages.

Clark, E. L. et al., "Measurements of Energetic Proton Transport through Magnetized Plasma from Intense Laser Interactions with Solids," *Physical Review Letters*, 2000, 84(4), 670-673 [Abstract Only] 1 page.

Clark, E. L., et al., "Energetic heavy ion and proton generation from ultraintense laser-plasma interactions with solids," *Phys. Rev. Lett.*, 2000, 1654-1657 [Abstract Only] 1 page.

CNRS - "Using laser-accelerated protons to fight cancer," Paris, Jan. 18, 2006. Downloaded at http://www.2.cnrs.fr/en/410.htm?debut=8 &print=1 on Apr. 17, 2006.

Coutrakon, G., et al., "Beam Optics for a Scanned Proton Beam at Loma Linda University Medical Center," *AIP Conference Proceedings*, 2003, 680 (Application of Accelerators in Research and Industry), 1116-1120 [Abstract Only] 1 page.

Cowan, T. E. et al., "Ultra-low emittance, high current proton beams produced with a laser-virtual cathode sheath accelerator," *Nuclear Instruments & Methods in Physics Research Section A-Accelerators*

*Spectrometers Detectors and Associated Equipment*, May 21, 2005, 544(1-2), 277-284, [Abstract Only] 1 page.

Cowan, T. et al., "High Energy Density and Exotic Acceleration Schemes," summary of reported results and principal technical discussions from Working Group on High Energy Density Physics and Exotic Acceleration Schemes at the 2002 workshop on Advanced Accelerator Concepts at the Mandalay Beach resort, Jun. 22-28, 2002; at www.slac.stanford.edu/arp/arb/tn/arbvo14/ARDB300.pdf.

d'Humieres, E. et al., "Proton acceleration mechanisms in high-intensity laser interaction with thin foils," *Physics of Plasmas*, 12(9), Art. No. 062704, Sep. 2005, [Abstract Only] 1 page.

Esirkepov, T. et al., "Generation of High Quality Laser Accelerated Ion Beams," *Phys, Rev. Lett.*, Nov. 26, 2002, 89(17), 4 pages.

Esirkepov, T. et al., "Laser Ion-Acceleration Scaling Laws Seen in Multiparametric Particle-in-Cell Simulations," *Physical Review Letters*, Mar. 17, 2006, 96, pp. 105001-1 to 105001-4.

Esirkepov, T., "To achiever Schwinger limit on Earth," May 2003, 2 pages, downloaded from the internet at http://wwwapr.apr.jaeri.go.jp/aprc/e/results/simulation/timur/mirror/ on Jun. 14, 2005.

Fan, J. et al., "Implementation of Monte Carlo Dose Verification for Proton Therapy QA," Abstract No. 2939, *AAPM 47th Annual Meeting*, Seattle, WA, Jul 28, 2005; downloaded at http://www.aapm.org/meetings/05AM/prabs.asp?mid=18&aid=2939 on Jun. 29, 2005.

Ferrand, R. et al., "Use of Ultra Intense Lasers Hope for Cheap and Compact Proton Machines," *42nd Annual Meeting of the Societe francaise de Physique Medicale*, Jun. 3-6, 2003, Reims, France, (Abstract), p. 4.

Fourkal, E. et al., "Analytical calculation of spread-out Bragg-peak distributions for laser-accelerated proton beams," *AAPM 47th Annual Meeting*, Seattle, WA, Jul. 24, 2005, 3 pages.

Fourkal, E. et al., "Intensity modulated radiation therapy using laser-accelerated protons: a Monte Carlo dosimetric study," *Phys. Med. Biol.*, 2004, 49, 1-24.

Fourkal, E., et al., "Particle in cell simulation of laser-accelerated proton beams for radiation therapy," *Med. Phys.*, 2002, 29(12), 2788-2798.

Fuchs, J. et al., "Laser-driven proton scaling laws and new paths towards energy increase," *Nature Physics*, Published online: Dec. 25, 2005.

Gazda, M. J. et al., "Principles of radiation therapy," Cancer Management: A Multidisciplinary Approach, Ch. 2, 7th Ed, 2003, 9-19 downloaded at http://www.cancernetwork.com/handbook/contents.htm on May 18, 2004.

Hanson, T. "The little beam that could," *Eurekalert*, Feb. 1, 2006; available online at http://www.eurekalert.org/pub_releases/2006-02/danl-tlb03106.php.

Hatchett, S. P., et al., "Electron, photon, and ion beams from the relativistic interaction of Petawatt laser pulses with solid targets," *Physics of Plasmas*, 2000, 7(5, Pt. 2), 2076-2082 [Abstract Only] 1 page.

Jones, D. T. L., "Magnetically scanned proton therapy beams: rationales and principles," *Rad. Phys. And Chem.*, 2001, 61(3-6), 615-618.

Joshi, C. et al., "Plasma accelerators at the energy frontier and on tabletops," *Physics Today*, 2003, 56(6), 47-53 [Abstract Only] 1 page.

Kainz, K. K. et al., "Dual Scattering Foil Design for Poly-Energetic Electron Beams," *Physics in Medicine & Biology*, Mar. 7, 2005, 50(5), 755-767 [Abstract Only] 1 page.

Kaluza, M. C., *Characterisation of Laser-Accelerated Proton Beams*, Max-Planck-Institute für Quantenoptik, Jun. 14, 2004, 1-139.

Krushelnick, K. et al., "Multi-MeV Ion Production from High-Intensity Laser Interactions with Underdense Plasmas," *Physical Review Letters*, 1999, 83(4), 737-740 [Abstract Only] 1 page.

Ledingham, K W. D., et al., "Application for Nuclear Phenomena Generated by Ultra-Intense Lasers," Science, May 16, 2003, 300, 1107-1111.

Litzenberg, D. et al., "The biological effectiveness of laser-accelerated sub-picosecond proton pulses," 44th AAPM Annual Meeting, Montreal, Jul. 14, 2002, Abstract No. 8623. Retrieved online at URL: http://www.aapm.org/meetings/02AM/pdf/8623081256.pdf.

Lomax, A.J., "Intensity Modulated Proton Therapy: Methods and Clinical Applications," *42nd Annual Meeting of the Société Française de Physique Médicale*, Jun. 3-6, 2003, Abstract, 1 page.

Lomax, T., "Swiss Protontherapy" Department of Radiation Medicine, The Paul Scherrer Institute, Switzerland, Jun. 2003.

Luo, W. et al., "A Dosimetric Comparison between Laser-Proton Therapy and Photon IMRT," Abstract No. 3704, *AAPM 47th Annual Meeting*, Seattle, WA, Jul. 24, 2005.

Luo, W. et al., "Particle selection and beam collimation system for laser-accelerated proton beam therapy," Med. Phys., Mar. 2005, 32(3), 794-806.

Mackinnon, A. J. et al., "Effect of Plasma Scale Length on Multi-MeV Proton Production by Intense Laser Pulses," *Physical Review Letters*, 2001, 86(9), 1769-1772 [Abstract Only] 1 page.

Maksimchuck, A., et al., "Forward ion acceleration in thin films driven by a high intensity laser," *Phys. Rev. Lett.*, 2000, 84, 4108-4111 [Abstract Only] 1 page.

Maksimchuk, K., et al., "Laser protons," *Physical Review Letters*, May 1, 2000 downloaded at http://www.aip.org/physnews/graphics/html/lasproton.html on Sep. 16, 2003.

Malka, V., "Particle beams produced by ultra short and intense lasers," Workshop on "Extreme Field Science and Relativistic Engineering," JAERI, Jan. 6-7 (2004), 29 pages.

Matsukado, K. et al., "Development of the Laser-Plasma Ion Source for Cancer Therapy," *The Review of Laser Engineering*, Nov. 2003, 31(11), 1 page Abstract, downloaded at http://wwwsoc.nii.ac.jp/lsj/abstract/2003/V31No11_0721.html on Jun. 14, 2005.

Matsukado, K. et al., "Energetic Protons from a Few-Micron Metallic Foil Evaporated by an Intense Laser Pulse," *Phys. Rev. Letts*, 2003, 91(21) [Abstract only] 1 page.

McKenna, P. et al., "Characterisation of the astra laser in proton acceleration experiments," 2001/2002 *Central Laser Facility annual report* 2001-2002, 79-81.

McKenna, P. et al., Characterization of Multiterawatt Laser-solid interactions for Protron Acceleration, *Review of Scientific Instr.*, 2002, 73(12), 4176-4184.

McKenna, P. et al., "Characterization of proton and heavier ion acceleration in ultrahigh-intensity laser interactions with heated target foils," *Phys Rev E Stat Nonlin Soft Matter Phys.* Epub Sep. 21, 2004, 70(3 Pt 2), 036405, available online at http://intapp.medscape.com/px/medlineapp/ ; 1 page.

McKenna, P. et al., "Nuclear reactions in copper induced by protons from a petawatt laser-foil interaction," *Applied Physics Letters*, 2004, 84(5), 675-677 [Abstract Only], 1 page.

Medema, J. et al., "Fully Automated and Unattended [$^{18}$F] Fluoride and [$^{18}$F]FDG Production using PLC Controlled Systems," Originally downloaded from the internet on May 30, 2003 at http://www.kvi.nl/~agorcalc/ecpm31/abstracts/medema2.html.

Mendonça, J. T. et al., "Proton and neutron sources using terawatt lasers," *Meas. Sci Technol.*, 2001, 12, 1801-1812.

Mourou, G. A. et al., "Extreme light; Focusing light with the power of 1,000 Hoover Dams onto a point the size of a Cell Nucleus accelerates electrons to the speed of light in a femtosecond," *Scientific American*, May 2002, 81-86.

Nakano, T. et al., "CT based treatment planning system of proton beam therapy for ocular melanoma," Nuclear Instruments and Methods in Physics Research B, 2003 210, 316-324.

Oishi, Y. et al., "Proton Generation by Ultra-Short High-Power Laser and the Dependence on Laser Intensity and Pulse Duration," *the Review of Laser Engineering*, Nov. 2003, 31(11), 1 page Abstract, downloaded at http://wwwsoc.nii.ac.jp/lsj/abstract/2003/V31No11_0747.html on Jun. 14, 2005.

Prelec, K., "Ions and Ion Accelerators For Cancer Treatment," *Fizika*, B 6, 1997, 4, 177-206.

Pukhov, A., "Strong field interaction of laser radiation," *Reports on Progress in Physics*, 2003, 66(1), 47-101 [Abstract Only] 1 page.

Santala, M. I. K. et al., "Production of radioactive nuclides by energetic protons generated from intense laser-plasma interactions," Applied Physics Letters, Jan. 1, 2001, 78(1), 19-21.

Schreiber, J., "Pointing of laser-accelerated proton beams," *Physics of Plasma*, 2006, 13, 033111-1 to 033111-5.

Scientific Report of the 2nd Workshop on Application of Bright and Ultra-Short Particle Sources with Intense Table-Top Lasers, Carre des Sciences, Paris, Dec. 2-4, 2002, 1-19.

Sentoku, Y. et al., "High-energy ion generation in interaction of short laser pulse with high-density plasma," Appl. Phys. B, 2002, 74, 207-215.

Silva, L. O. et al., "Protons hock Acceleration in Laser-Plasma Interaction," *Physical Review Letters*, 2004, 92(1), 015002/1-0150024 [Abstract Only] 1 page.

Smedarchina, Z. et al., "Kinetic isotope effects for concerted multiple proton transfer: A direct dynamics study of an active-site mode of carbonic anhydrase II," *Journal of the American Chemical Society*, 2003 125(1), 243-251 [Abstract Only] 1 page.

Smith, A., M. D., Anderson Cancer Center, Univ. of Texas, Chairing Session at World Congress in Med. Phys. And Bioeng. Sydney, Australia, Aug. 2003, "How particles can be therapeutic," downloaded at http://physicsweb.org/articles/world/16/8/9 on Nov. 2, 2006.

Snavely, R.A., et al., "Intense high energy proton beams from petawatt laser irradiation of solids," *Phys. Rev. Lett.*, 2000, 2945-2948 [Abstract Only] 1 page.

Spence, I. et al., "Laser generation of proton beams for the production of short-lived positron emitting radioisotopes," *Nuclear Instruments & Methods in Physics Research Section B; Beam Interactions with Materials and Atoms*, 2001, 183(3-4), 449-458 [Abstract Only] 1 page.

Tajima, T., "Laser Wakefield Accelerator," downloaded from the internet at http://www.ph.utexas.edu/dept/research/tajima/ on May 19, 2003.

Tajima, T., "Ultraintense Laser and Relativistic Engineering," *The Review of Laser Engineering*, Nov. 2003, 31(11), 1 page Abstract, downloaded at http://wwwsoc.nii.ac.jp/lsj/abstract/2003/V31No11_0707.html on Jun. 14, 2005.

Terranova, F. et al., "Multi-GeV laser driven proton acceleration in the high current regime," downloaded at http://hadron.kek.jp/Nufact/Terranova_WG3.pdf on Dec. 15, 2006.

Umstadter, D. et al., High-Field Science Group - HFS group Web Site. URL: http://www.eecs.umich.edu/USL-HFS/, Sep. 16, 2003.

Umstadter, D. et al., "New developments in laser acceleration of beams," *IEEE Proceedings of the 2001 Particle Accelerator Conf.*, Chicago, 2001, pp. 117-121.

Umstadter, D., et al., "Relativistic laser-plasma interactions," *J. Phys. D: Appl. Phys.*, 2003, 36, R151-R165.

Vorobiev, L. G. et al., "Concepts of a compact achromatic proton gantry with a wide scanning field," *Nucl. Instr. & Methods in Phys. Res., Sect. A: Accel. Spectr. Detect. And Assoc. Equip.* 1998, 406(2), 307-310.

Vrenken, H. et al., "A design of a compact gantry for proton therapy with 2D-scanning," *Methods in Physics Res., Sect. A: Accel. Spectr. Detect. And Assoc. Equip.*, 1999, 426(2-3), 618-624. AN 1999:330619.

Wilks, S. C. et al., "Absorption of ultraintense laser pulses," *Physical Reviews Letters*, 1992, 1383-1386 [Abstract Only] 1 page.

Wilks, S. C. et al., "Energetic proton generation in ulta-intense laser-solid interactions," *Physics of Plasmas*, 2001, 8(2), 542-549 [Abstract Only].

Wlazelek, A., "Cancer-blaster shoots for Valley," Retrieved from the Internet on Jan. 20, 2005 at : http://www.mcall.com/news/local/all-al_5protonjan20,0,3504507.story?coll=all-newslocal-hed.

Yang, J. M., Nuclear reactions in copper induced by protons from a petawatt laser-foil interaction, *Applied Physics Letters*, Feb. 2, 2004, 84(5), 675-677.

Yu, Q.-C., "A Proton beam delivery system for conformal therapy and intensity modulated therapy," *Goaneng Wuli Yu Gewuli* (written in Chinese) 2001, 25(8), 793-798. (English abstract included on p. 798).

Yu, Q.-C., "Soft-Modulating And Double-Scattering Beam Delivery System For Proton Therapy," *Goaneng Wuli Yu Hewuli* (written in Chinese), 2001, 25(3), 271-276. (English abstract included on p. 276).

Archambeau, J.O., et al., "Role of proton beam irradiation in treatment of pediatric CNS malignancies," *Int. J. Radiation Oncology Biol. Phys.*, 1992, 22, 287-294.

Austin-Seymour, M., et al., "considerations in fractionated proton radiotherapy: clinical potential and results," *Radiother. Oncol.*, 1990, 17, 29 [Abstract only].

Beeckman, W., et al., "Preliminary design of a reduced cost proton therapy facility using a compact, high field isochronous cyclotron," *Nucl. Instr. Meth.*, B56/57, 1991, 1201-1204.

Bettega, D. et al., "Radiobiological studies on the 65 MeV therapeutic proton beam at Nice using human tumour cells," *International Journal of Radiation Biology*, Oct. 2000, 76(10), 1297-1302.

Birdsall, C. K. and Langdon, A. B., Overall View of A One-Dimensional Electrostatic Program in: *Plasma Physics via Computer Simulation*, 1985, Chapter 2, (McGraw-Hill Book Company, Singapore), pp. 7-27.

Bonlie, J., et al., "Ultrashort pulse Ti:sapphire laser system pumped by frequency doubled Nd:glass lasers," in *Generation, Amplification and Measurement of Ultrashort Laser Pulses III*, White, W.E., et al., (Eds.), Proc. SPIE, 1996, vol. 2701, pp. 107-116 [Abstract only].

Bortfeld, T., et al., "Methods of image reconstruction from projections applied to conformation radiotherapy," *Phys. Med. Biol.*, 1990, 35(10) 1423-1434.

Brahme, A., "Optimization of stationary and moving beam radiation therapy techniques," *Radiotherapy & Oncology*, 1988, 12, 129-140.

Brahme, et al., "Optimization of proton and heavy ion therapy using an adaptive inversion algorithm," *Radiother. Oncol.*, 1989, 15, 189-197.

Bulanov, S. V. et al., "Relativistic interaction of ultra-short laser pulses with plasmas," General Physics Institute, *AIP Conf. Proceedings*, 2002, Moscow, Russia, 104-118.

Bulanov, S. V., et al., "Generation Of Collimated Beams Of Relativistic Ions In Laser-Plasma Interactions," *JETP Letts.*, 2000, 71(10), 407-411.

Bulanov, S.V., et al., "Interaction Of Petawatt Laser Pulses With Underdense Plasmas," *Plasma Phys.*, 1999, 25, 701-714.

Bulanov. S. V. et al., "Generation of High-Quality Charged Particle Beams during the Acceleration of Ions by High-Power Laser Radiation," *Plasma Physics Reports*, Dec. 2002, 28(12), 975-991.

Burman C, et al., "Fitting Of Normal Tissue Tolerence Data To An Analytic Function," *Int. J. Radiat. Oncol. Biol. Phys.*, 1991, 123-135.

Burman, C., et al., "Planning Delivery, And Quality Assurance Of Intensity-Modulated Radiotherapy Using Dynamic Multileaf Collimator: A Strategy For Large-Scale Implementation For The Treatment Of Carcinoma Of The Prostate," *Int. J. Radiat. Oncol. Biol. Phys.*, 1997, 39(4), 863-873.

Candy, J., et al., "A Symplectic Integration Algorithm For Separable Hamiltonian Functions," *J. Comp. Phys.*, 1991, 92, 230-239.

Carlsson, A. K. et al., "Monte Carlo And Analytical Calculation Of Proton Pencil Beams For Computerized Treatment Plan Optimization," *Phys. Med. Biol.*, 1997, 42, 1033-1053.

Clark, E. et all, "Multi-MeV heavy ion production from ultra-intense laser plasma interactions," *Session JP1 - Poster Session*, Nov. 17, 1999; retrieved online at http://flux.aps.org/meeting/YR99/DPP99/abs/S475073.html on Feb. 13, 2007 [Abstract only].

Coutrakon, G., et al., "A Prototype Beam Delivery System For The Proton Medical Accelerator At Loma Linda," *Med. Phys.*, 1991, 18(6), 1093-1099.

Davies, W. G., "The Design of Ion-Optical Systems for Medical and Industrial Irradiation," *Nuclear Instruments and Methods in Physics Research*, 1989, B40/41, 1178-1181.

Emami, B., et al., "Tolerance Of Normal Tissue To Therapeutic Irradiation," *Int. J. Radiat. Oncol. Biol. Phys.*, 1991, 21, 109-122.

Esarey, E., et al., "Overview of Plasma-Based Accelerator Concepts," *IEEE Trans Plasma Sci.*, Apr. 1996, 24(2), 252-288.

Esirkepov, T. et al., "Proposed Double-Layer Target For The Generation Of High-Quality Laser-Accelerated Ion Beams," *Physical Review Letters*, Oct. 21, 2002, 89(17), 175003-1 to 175003-4.

Ferrari, A., et al., "Intermediate And High Energy Models In FLUKA: Improvements, Benchmarks And Application," *Conference Proc. Nuclear Data for Science & Tech.*, Reffo, G., et al., (Eds.), SIF, Bologna, 1997, 59, 247-253.

Flanz, J.B., et al., "Initial Equipment Commissioning Of The Northeast Proton Therapy Center," *Proc. The* 1998 *Cyclotron Conference*, 1998, 319-323.

Fortov, V. E. et al., "Combustion And Detonation In Pulsed Power Generators," *Challenges in Propellants and Combustion: 100 years after Nobel*, May 27-31, 1996.

"GEANT: Detector Description And Simulation Tool," Technical Report CERN Program Library, long writeup, CERN, Geneva, Switzerland W5013, 1993, 467 pages.

Hendricks, J.S., et al., "Recent MCNP Developments," *IEEE Transactions on Nuclear Science*, 1992, 39(4), 1035-1040.

Holmes, T.W., et al., "A Comparison Of Three Inverse Treatment Planning Algorithms," *Phys. Med. Biol.*, 1994, 39, 91-106.

Jiang, S. B., "Development of A Compensator Based Intensity-Modulated Radiation Therapy," 1998, Medical College of Ohio, UMI Microform 9930422.

Jongen, y.A., et al., "Proton Therapy System For MGh's NPTC: Equipment Description And Progress Report," *Cyclotrons & their Applications*, Cornell, J.C. (Ed.), New Jersey: World Scientific, 1996, 606-609.

Key, M.H., et al., "Studies Of The Relativistic Electron Source And Related Phenomena In Petawatt Laser Matter Interactions," *In First International Conference On Inertial Fusion Sciences And Applications*, Bordeaus, France, 1999, 1-9.

Kjellberg, R.N., "Stereotactic Bragg Peak Proton Radiosurgery For Cerebral Arteriovenous Malformations," *Ann. Clin. Res.*, 1986, 47, 17-19.

Landau, L., "On The Energy Loss Of Fast Particles By Ionization," *J. Phys. USSR*, 1944, 201-210.

Lee, M., et al., "A Comparison Of Proton And Megavoltage X-Ray Treatment Planning For Prostate Cancer," *Radiother, Oncol.*, 1994, 239-253 [Abstract only].

Li, J. S. et al., "A Particle Track-Repeating Algorithm For Proton Beam Dose Calculation," *Phys. Med. Biol.*, 2005, 50, 1001-1010.

Li, J.-S., et al., "Monte Carlo based superposition dose calculation for proton beam radiotherapy," *Med. Phys.*, 2001, 1250 [Abstract only].

Lomax, A.J., "Potential Role Of Intensity-Modulated Photons And Protons In The Treatment Of The Breast And Regional Nodes," *Int. J. Rad. Oncol. Biol. Phys.*, 2003, 55(3), 785-792.

Lomax, A.J., et al., "A Treatment Planning Inter-Comparison Of Proton And Intensity Modulated Photon Radiotherapy," *Radiother. Oncol.*, 1999, 51, 257-271.

Lomax, A.J., et al., "intensity modulation in radiotherapy: photons versus protons in the paranasal sinus," *Radiother. Oncol.* 2003, 66, 11-18.

Matsukado, K. et al., "Ion Generation Via Interaction Between Intense Ultra-Short-Laser Pulse And Solid Target For Application To Cancer Therapy," *AIP Conference Proceedings, CP647 (Advanced Accelerator Concepts)*, 2002, 265-268.

Miralbell, R., et al., "Potential Reduction Of The Incidence Of Radiation-Induced Second Cancers By Using Proton Beams In the Treatment Of Pediatric Tumors," *Int. J. Rad. Onc. Biol. Phys.*, 2002, 54(3), 824-829.

Modena, A., et al., "Electron Acceleration From the Breaking of Relativistic Plasma Waves," *Nature*, 1995, 377, 606-608.

Moliere, G.Z., "Theorie Der Streuung Schneller Gelandener Teilchen II: Mehrfach-Und Vielfachstreunng," *Z. Naturforsch*, 1948, 78-85.

Mourou, G.A., et al., "Ultrahigh-Intensity Lasers: Physics Of The Extreme On A Tabletop," *Physics, Today*, Jan. 1998, 22-28.

Moyers, M., "Proton Therapy," in: *The Modern Technology of Radiation Oncology*, Van Dyk, J. (Ed.), Medical Physics Publishing, Madison, 1999, Chapter 20, 823-869.

Moyers, M.F., et al., "Water Equivalence Of Various Materials For 155 To 250 Mev Protons," *Med. Phys.*, May/Jun. 1992, 19(3), (abstract V4).

Nchodu, M. R. et al., "Measurements of Energy spectra in the NAC proton therapy beam," *Radiation Protection Dosimetry*, 1997, 70(1), 477-480.

Nelson, G. A. et al., "Research Activites At The Loma Linda University And Proton Treatment Facility - An Overview," *Physica Medica*, 2001, 17(Suppl. 1), 30-32.

Olifant, M.O., "The Acceleration Of Particles To Very High Energies," DSIR, U. Birmingham Archive, *Proc. Phys. Soc.*, 1947, 59, 666-677 [Abstract only].

Olivier, S. S., "First Significant Image Improvements From A Sodium-Layer Laser Guide Star Adaptive Optics System At Lick Observatory," *SPIE*, vol. 3126, 240-248.

Pawlicki, T. et al., "Monte Carlo Calculated Beamlets for Photon Beam Inverse Planning," *Medical Physics*, Jun. 1999, 26(6), 1064-1065, Abstract No. MO-D1-07.

Peacock, J. H. et al., "Normal-Tissue Effects In Radiotherapy: Physics Meets Biology. Report On A Workshop Held At Hartsfield Manor, Betchworth, Surrey, UK, Jul. 14-16 Jul. 1997," *Int. J. Radiat. Biol.*, 1998, 73(3), 341-344.

Pedroni, E., "Therapy Planning System For The SIN-Pion Therapy Facility," in *Treatment Planning for External Beam Therapy with Neutrons*, Burger, G., et al. (Eds.), Munich: Urban and Schwarzenberg, 60-69.

Ritchie, A.B., et al., "Ultrashort Pulse Laser Ionization Of Ions In A Plasma," *Phys. Rev. Lett.*, 1998, 58(5) 6460-6464.

Rogers, D.W.O., et al., "Monte Carlo Techniques Of Electron And Photon Transport For Radiation Dosimetry," in *The Dosimetry of Ionizing Radiation*, vol. III, Kase, K., et al. (Eds.), Academic press, San Diego, CA, 1990, 427-439, 522-523, 526-535, 537-539.

Sakagami, H. et al., "Pulse Expansion And Soliton-Like Propagation Of Ultrahigh Intense Short Pulse Laser," i *Fast Ignitor and High Field Science*, Chapter 2, Tajima, T. et al., (Eds.), Plenum, NY, 2000, pp. 29-38.

Seddon, J.M., "Relative Survival Rates After Alternative Therapies For Uveal Melanoma," *Ophthalmology.*, 1990, 97(6), 769-777.

Shipley, W., et al., "Advanced Prostate Cancer: The Results Of A Randomized Comparative Trial Of High Dose Irradiation Boosting With Conformal Protons Compared With Conventional Dose Irradiation Using Photons Alone," *Int. J. Radiation Oncology Biol. Phys.*, 1995, 32, 3-12.

Sisterson, J.M., "Clinical Use Of Protons And Ion Beams From A Worldwide Prespective," *Nucl. Instr. Meth. Phys. Res.*, 1989, B40/41, 1350-1353.

Sisterson, J.M., "Proton Therapy in 1996" *AIP Conference Proceedings*, Feb. 5, 1997, vol. 392, pp. 1261-1264.

Sisterson, J.M., *Particles* Newsletter No. 7, Jan. 1991, 10 pages.

Slater J. M. et al., "Carcinoma Of The Tonsillar Region: Potential For Use Of Proton Beam Therapy," *Int. J. Radiation Oncology Biol. Phys.*, 1992, 22, 311-319.

Slater, J. D., et al., "The Potential For Proton Beam Therapy In Locally Advanced Carcinoma Of The Cervix," *Int. J. Radiation Oncology Biol. Phys.*, 1992, 22, 343-347.

Spoirou, S.V., et al., "A Gradient Inverse Planning Algorithm With Dose-Vol. Constraints," *Med. Phys.*, 1998, 25(3), 321-333.

Stoyer, M. A. et al., "Observation of High Energy Protons Produced with a High Intensity Laser," *Session JF - Applications of Nuclear Physics*, Oral Session Abstract, Oct. 23, 1999; retrieved online at http://flux.aps.org/meetings/YR99/DNP99/abs/S550.html on Feb. 14, 2007.

Strickland, D., et al., "Compression Of Amplified Chirped Optical Pulses," *Opt. Comm.*, 1985, 56(3), 219-221.

Tajima, T., "High Energy Laser Plasma Accelerators," *Laser Part. Beams*, 1985, 3(4), 351-413.

Tajima, T., "Finite Size Particle Method," in *Computational Plasma Physics: With Applications to Fusion and Astrophysics*, Chapter 2, Addison-Wesley, Reading, MA, 1989, 37-50.

Tatsuzaki, H., Et Al., "3-D Comparative Study Of Proton Vs. X-Ray Radiation Thereapy For Rectal Cancer," *Int. J. Radiation Oncology Biol. Phys.*, 1991, 22, 369-374.

Tatsuzaki, H., et al., "Comparative Treatment Planning: Proton Vs X-Ray Beams Against Glioblastoma Multiform," *Int. J. Radiation Oncology Biol. Phys.*, 1991, 22, 265-273.

Umstadter, D., et al., "Nonlinear Optics in Relativistic Plasmas and Laser Wake Field Acceleration of Electrons," *Science*, 1996, 273, 472-475.

Vavilov, "Ionization Losses Of High Energy Heavy Particles," *Soviet Physics JETP*, 1957, 5(4), 749-751.

Verhey, L.J., et al., "Proton Beam Therapy," *Ann. Rev. Biophys. Bioeng.*, 1982, 11, 331-357.

Webb, S., "Optimisation Of Conformal Radiotherapy Dose Distributions By Simulated Annealing," *Phys. Med. Biol.*, 1990, 34(10), 1349-1370 [Abstract only].

Webb, S., "Optimizing The Planning Of Intensity-Modulated Radiotherapy," *Phys. Med. Biol.*, 1994, 39, 2229-2246.

Wilks, S.C., et al., "Absorption Of Ultrashort, Ultra-Intense Laser Light By Solids And Overdense Plasmas," *IEEE J. Quantum Electron.*, 1997, 33(11), 1954-1968.

Wilson, R.R., "Radiological Uses Of Fast Protons," *Radiology*, 1946, 47, 487-491.

* cited by examiner

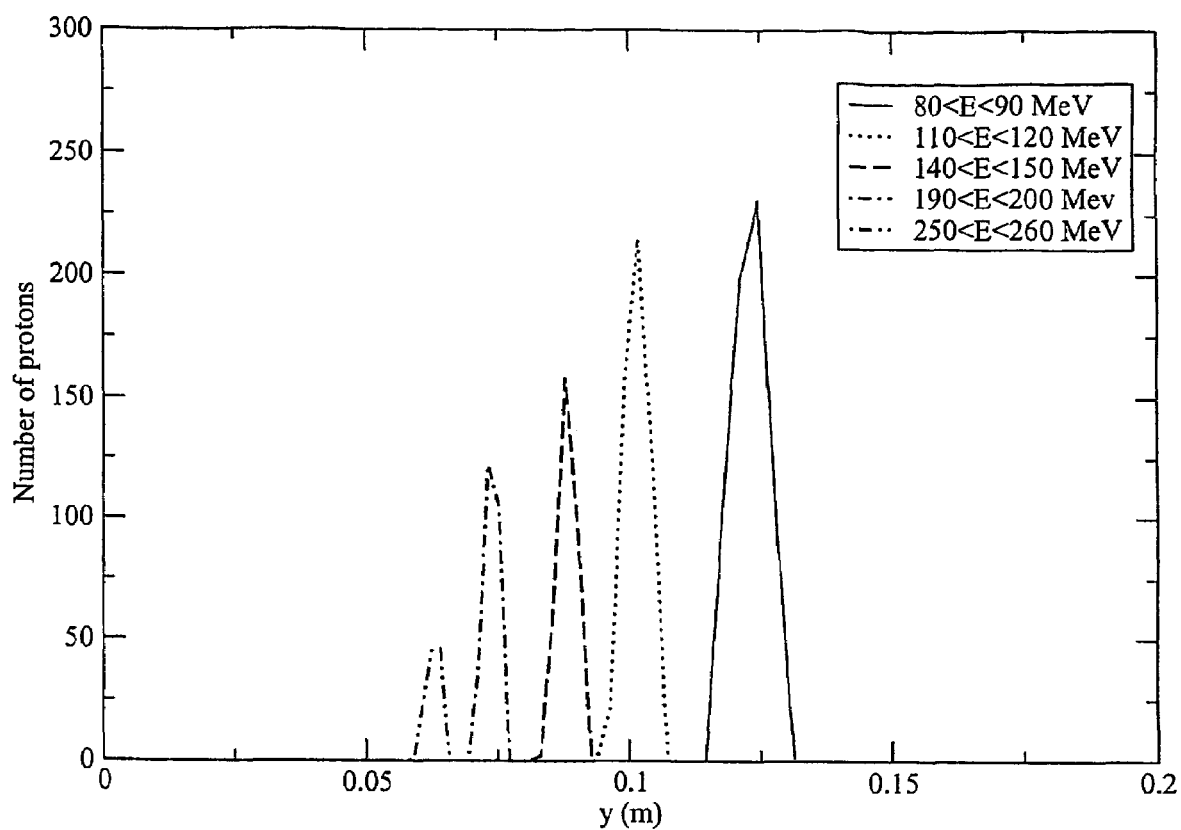

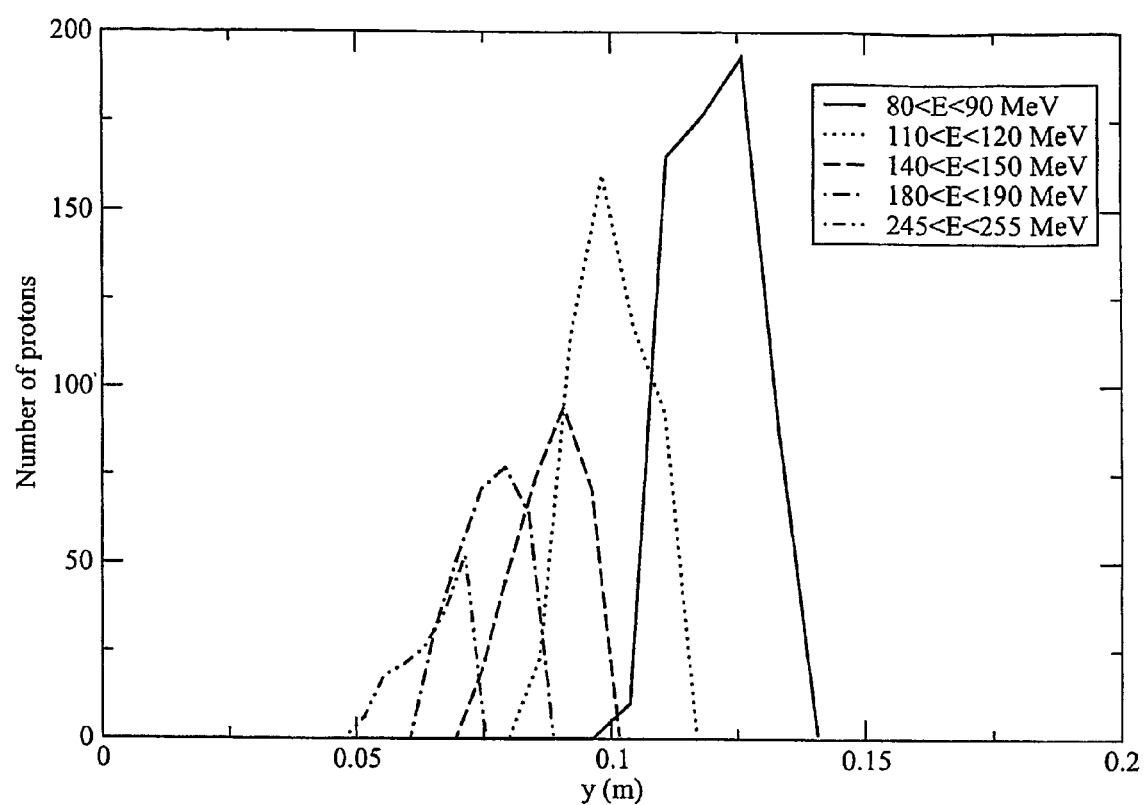

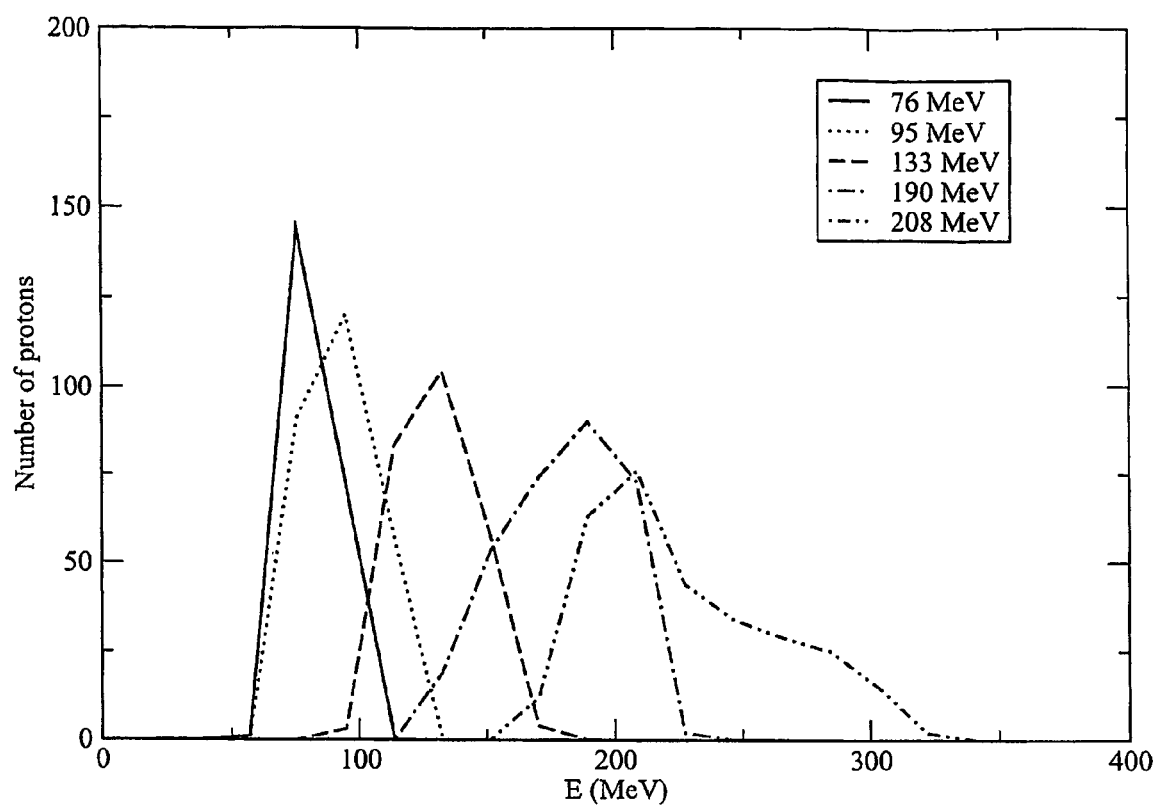

Figure 13
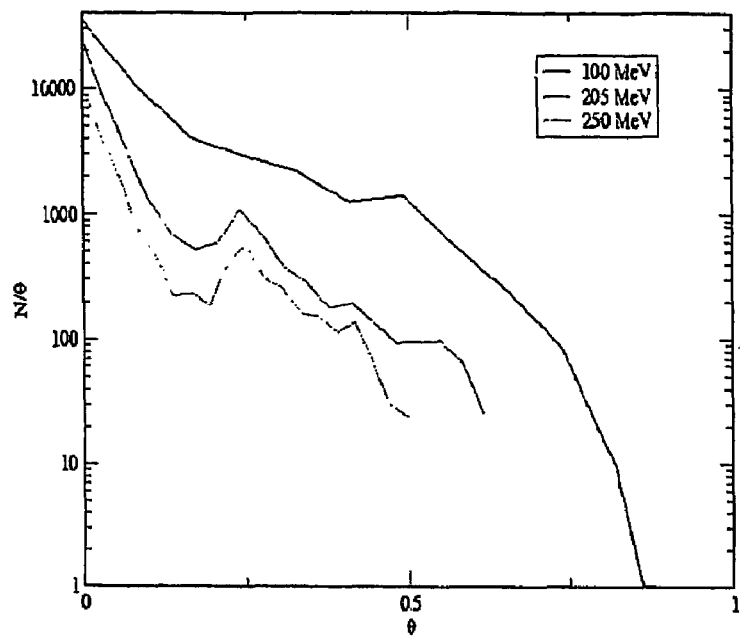
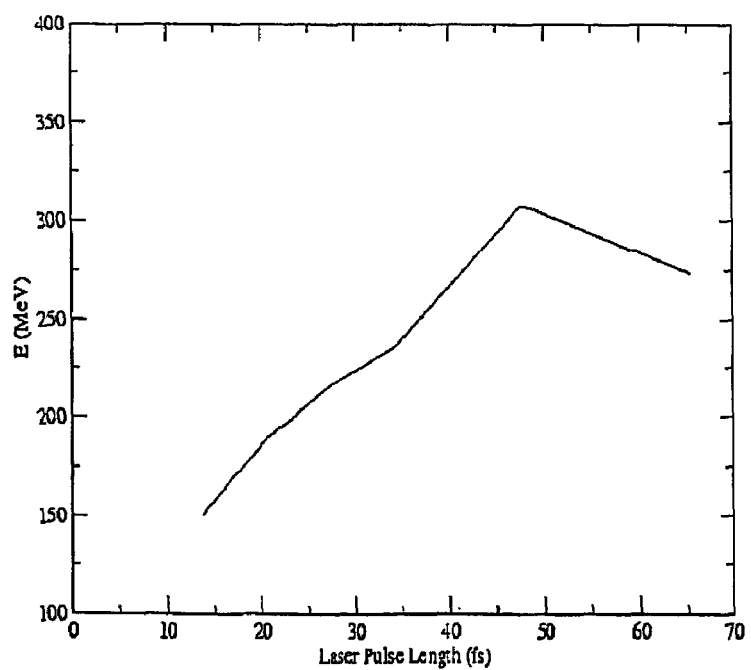

Figure 14
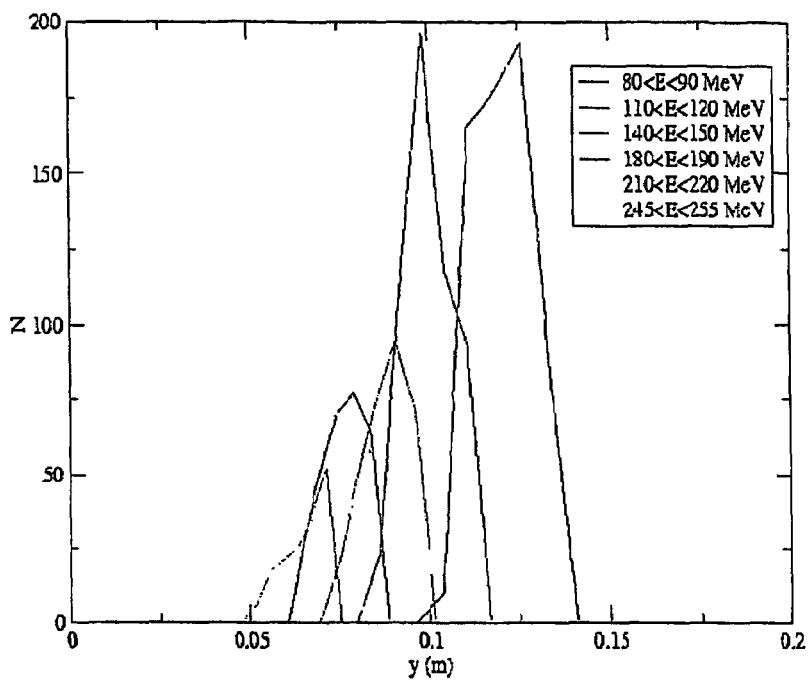
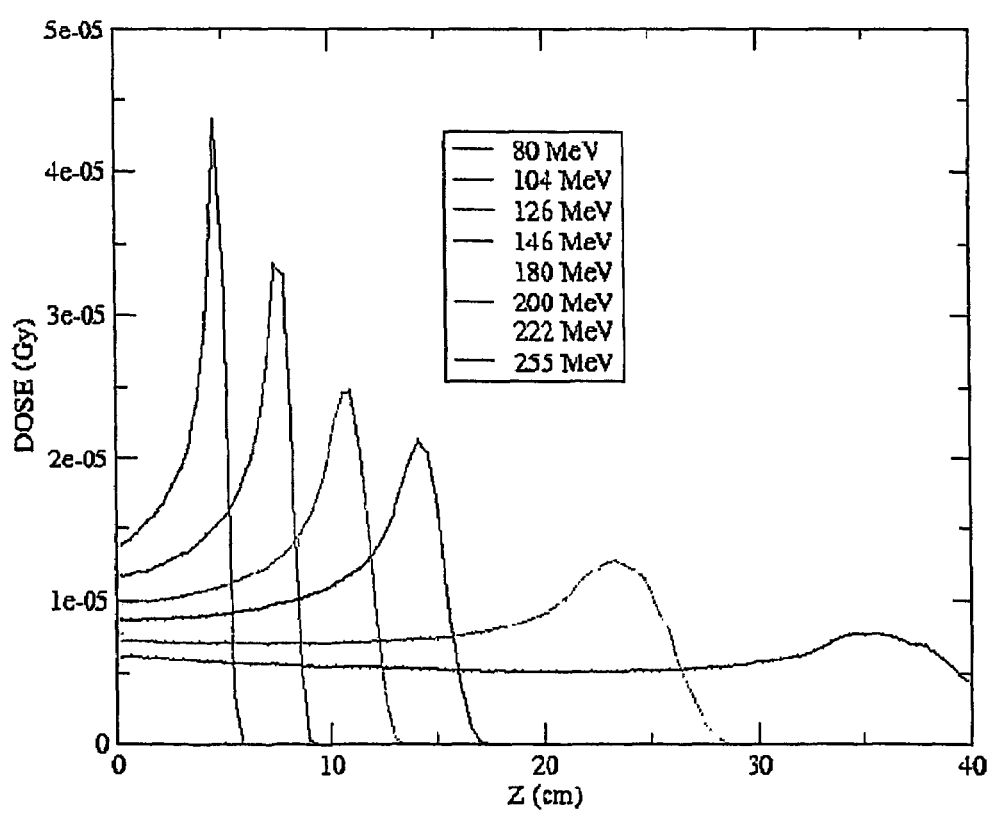

Figure 15
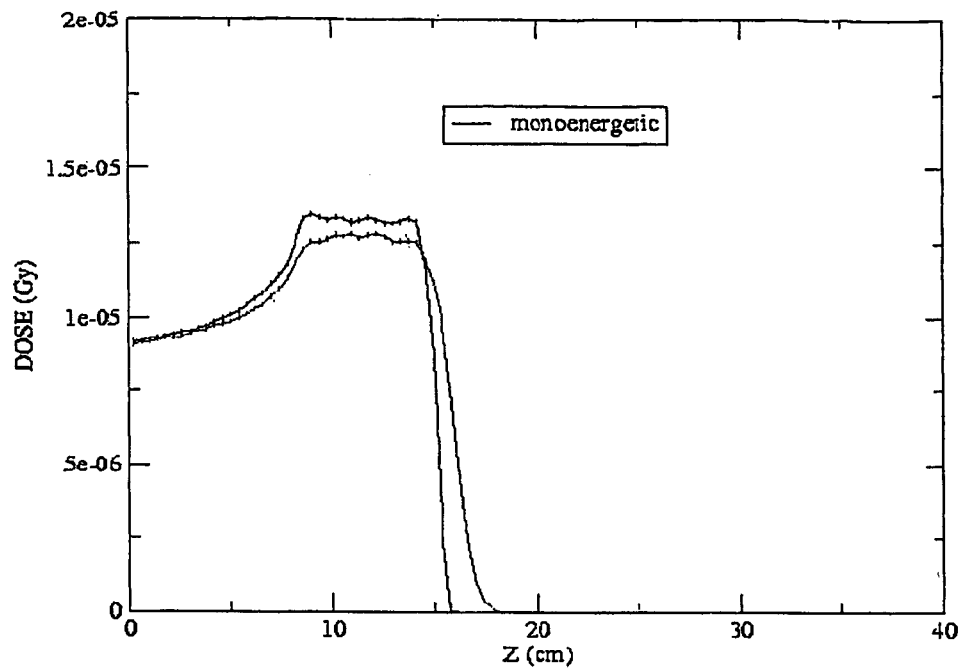
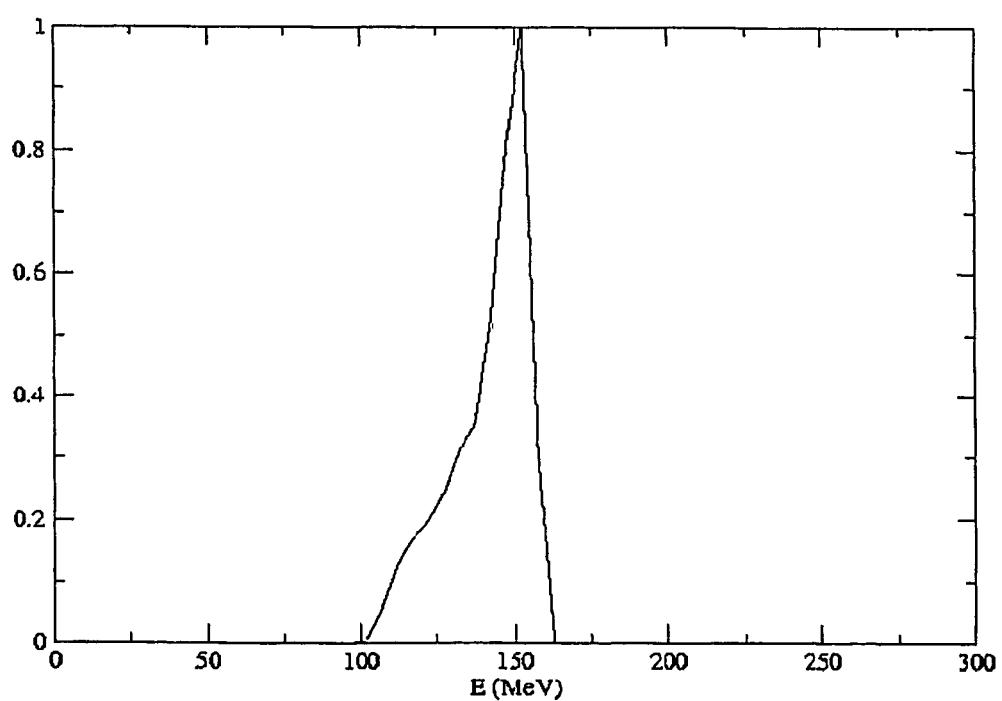

Figure 33
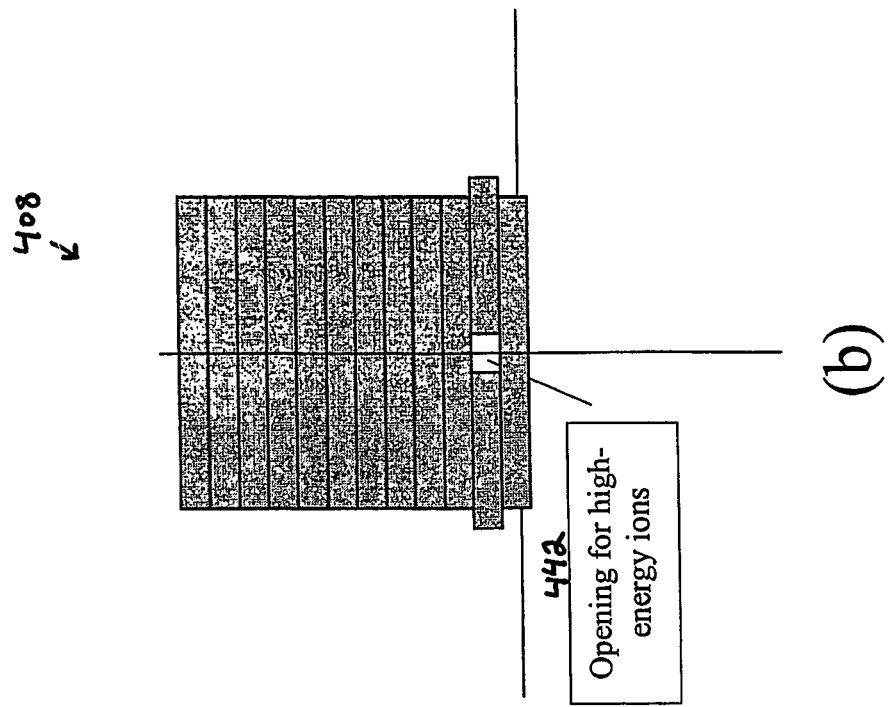
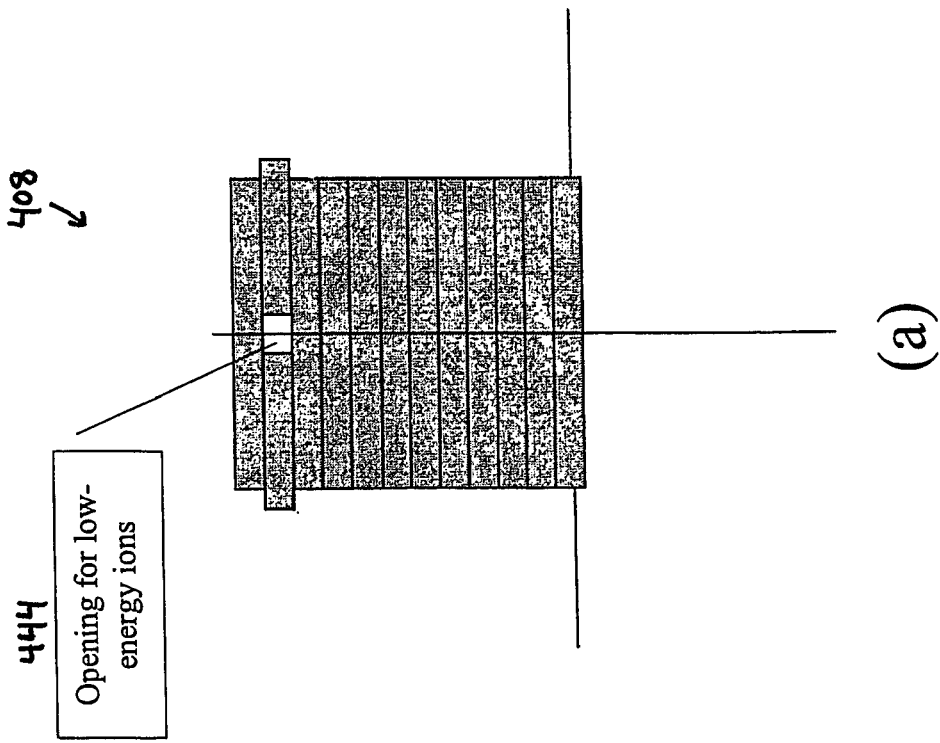

HIGH ENERGY POLYENERGETIC ION SELECTION SYSTEMS, ION BEAM THERAPY SYSTEMS, AND ION BEAM TREATMENT CENTERS

CROSS REFERENCE TO RELATED APPLICATIONS

This patent application claims the benefit of U.S. provisional patent application Ser. No. 60/475,027, filed Jun. 2, 2003, the entirety of which is incorporated by reference herein.

GOVERNMENT RIGHTS

The work leading to the disclosed invention was funded in whole or in part with Federal funds from the National Institutes of Health and the Health Resources and Services Administration. The Government may have certain rights in the invention under NIH contract number CA78331 and HRSA Grant No. 4C76HF00691-01-01.

FIELD OF THE INVENTION

The present invention is related to the field of devices and methods for generating high energy ion beams. The present invention is also related to uses of high energy ion beams for radiation therapy. In addition, the present invention is related to the field of treating patients in cancer treatment centers using high energy ion beams.

BACKGROUND OF THE INVENTION

Radiation therapy is one of the most effective tools for cancer treatment. It is well known that the use of proton beams provides the possibility of superior dose conformity to the treatment target as well as providing a better normal tissue sparing, as a result of the Bragg peak effect, compared to photons (e.g., X-rays) and electrons. See, e.g. T. Bortfeld, "*An analytical approximation of the Bragg curve for therapeutic proton beams*", Med. Phys., 2024–2033 (1997). While photons show high entrance dose and slow attenuation with depth, protons have a very sharp peak of energy deposition as a function of beam penetration. As a consequence, it is possible for a larger portion of the incident proton energy to be deposited within or very near the 3D tumor volume, thus avoiding radiation-induced injury to surrounding normal tissues that commonly occurs with x-rays and electrons.

Despite the dosimetric superiority characterized by the sharp proton Bragg peak, utilization of proton therapy has lagged behind that of photon therapy. This lag is apparently due to the operating regime (the total operating cost for accelerator maintenance, energy consumption, and technical support) for proton accelerators being at least an order of magnitude higher compared to electron/X-ray medical accelerators. Currently, proton therapy centers utilize cyclotrons and synchrotrons. See, e.g., Y. A. Jongen et al., "*Proton therapy system for MGH's NPTC: equipment description and progress report*", Cyclotrons and their Applications, J. C. Cornell (ed) (New Jersey: World Scientific) 606–609 (1996); "*Initial equipment commissioning of the North Proton Therapy Center*", Proc. of the 1998 Cyclotron Conference (1998); and F. T. Cole, "*Accelerator Considerations in the Design of a Proton Therapy Facility*", Particle Acceleration Corp. Rep (1991). Despite a somewhat limited number of clinical cases from these facilities, treatment records have shown encouraging results particularly for well localized radio-resistant lesions. See, e.g., M. Fuss et al., "*Proton radiation therapy (PRT) for pediatric optic pathway gliomas: Comparison with 3D planned conventional photons and a standard photon technique*", Int. J. Radiation Oncology Biol. Phys., 1117–1126 (1999); J. Slater et al., "*Conformal proton therapy for prostate carcinoma*" Int. J. Radiation Oncology Biol. Phys., 299–304 (1998); W. Shipley et al., "*Advanced prostate cancer: the results of a randomized comparative trial of high dose irradiation boosting with conformal protons compared with conventional dose irradiation using photons alone*", Int. J. Radiation Oncology Biol. Phys., 3–12 (1995); and R. N. Kjellberg, "*Stereotactic Bragg Peak Proton Radiosurgery for Cerebral Arteriovenous Malformations*" Ann Clin. Res., Supp. 47, 17–25 (1986). This situation could be greatly improved by the availability of a compact, flexible, and cost effective proton therapy system, which would enable the widespread use of this superior beam modality and therefore bring significant advances in the management of cancer.

Thus, there remains the problem of providing a practical solution for a compact, flexible and cost-effective proton therapy system. See, e.g., C.-M. Ma et al., "*Laser accelerated proton beams for radiation therapy*", Med. Phys., 1236 (2001); and E. Fourkal et al., "*Particle in cell simulation of laser-accelerated proton beams for radiation therapy*", Med. Phys., 2788–2798 (2002). Such a proton therapy system will require three technological developments: (1) laser-acceleration of high-energy protons, (2) compact system design for ion selection and beam collimation, and (3) the associated treatment optimization software to utilize laser-accelerated proton beams.

U.S. Patent Application Pub. No. US 2002/0090194 A1 (Tajima) discloses a system and method of accelerating ions in an accelerator to optimize the energy produced by a light source. It is disclosed that several parameters may be controlled in constructing a target used in the accelerator system to adjust performance of the accelerator system.

Simulations of the laser acceleration of protons reported by Fourkal et al., showed that, due to their broad energy spectrum, it is unlikely that laser accelerated protons can be used for therapeutic treatments without prior proton energy selection. If such an energy distribution is achieved, however, it should be possible to provide a homogeneous dose distribution through the so-called Spread Out Bragg's Peak ("SOBP"). Using multiple beams (beamlets) it should also be possible to conform the dose distribution to the target laterally (intensity modulation). Intensity-modulated radiation therapy ("IMRT") using photon beams could deliver more conformal dose distribution to the target while minimizing the dose to surrounding organs compared to conventional photon treatments. In "*On the role of intensity-modulated radiation therapy in radiation oncology*", Med. Phys., 1473–1482 (2002), R. J. Shultz, et al. addressed the role of the intensity-modulated radiation therapy in treatments of specific disease sites. This topic of research is still in its latent stage requiring accumulation and analysis of more data, but the findings of Shultz et al. suggest that at least there could be an advantage of using IMRT for treatments of such sites as the digestive system (colorectal, esophagus, stomach), bladder and kidney.

Giving a homogeneous dose distribution in the target's depth direction may be possible; see, e.g., C. Yeboah et al., "*Intensity and energy modulated radiotherapy with proton beams: Variables affecting optimal prostate plan*", Med. Phys., 176–189 (2002); and A. Lomax, "*Intensity modulation methods for proton radiotherapy*", Phys. Med. Biol., 185–205 (1999). Accordingly, Energy- and Intensity-Modulated Proton Therapy ("EIMPT") should further improve target coverage and normal tissue sparing effects. In recent years, the planning and delivery of X-rays has improved considerably so that the gap between the conventional proton techniques and X-ray methods has decreased dramatically. The main pathway of research has been toward the optimization of individual beamlets and the calculation of optimal intensity distributions (for each beamlet) for intensity modulated treatments. See, e.g., E. Pedroni, "*Therapy planning system for the SIN-pion therapy facility*", in *Treatment Planning for External Beam Therapy with Neutrons*, ed. G. Burger, A. Breit and J. J. Broerse (Munich: Urban and Schwarzenberg); and T. Bortfeld et al., "*Methods of image reconstruction from projections applied to conformation radiotherapy*", Phys. Med. Biol., 1423–1434 (1990). Unfortunately, the implementation of intensity modulation for proton beams has lagged behind that of photons due to the design limitations of conventional beam delivery methods in proton therapy. See, e.g., M. Moyers "*Proton Therapy*", The Modern Technology of Radiation Oncology, ed. J. Van Dyk (Medical Physics Publishing, Madison, 1999). Thus, there remains the problem of providing a combination of a compact proton selection and collimation device and treatment optimization algorithm to make EIMPT possible using laser-accelerated proton beams.

Laser acceleration was first suggested in 1979 for electrons (T. Tajima and J. M. Dawson, "*Laser electron accelerator*", Phys. Rev. Lett., 267–270 (1979)), and rapid progress in laser-electron acceleration began in the 1990's after Chirped Pulse Amplification ("CPA") was invented (D. Strickland, G. Mourou, "*Compression of amplified chirped optical pulses,*" Opt. Comm., 219–221 (1985)) and convenient high fluence solid-state laser materials such as Ti:sapphire were discovered and developed. The first experiment that has observed protons generated with energy levels much beyond several MeV (58 MeV) is based on the Petawatt Laser at Lawrence Livermore National Laboratory ("LLNL"). See, e.g., M. H. Key et al., "*Studies of the Relativistic Electron Source and related Phenomena in Petawatt Laser Matter Interactions*", in First International Conference on Inertial Fusion Sciences and Applications (Bordeaux, France, 1999); and R. A. Snavely et al., "*Intense high energy proton beams from Petawatt Laser irradiation of solids*", Phys. Rev. Lett., 2945–2948 (2000). Until then, there had been several experiments that observed protons of energy levels up to 1 or 2 MeV. See, e.g., A. Maksimchuk et al., "*Forward Ion acceleration in thin films driven by a high intensity laser*", Phys. Rev. Lett. 4108–4111, (2000). Another experiment at the Rutherford-Appleton Laboratory in the U.K. has been reported recently with proton energy levels of up to 30 MeV. See, e.g., E. L. Clark et al., "*Energetic heavy ion and proton generation from ultraintense laser-plasma interactions with solids*", Phys. Rev. Lett., 1654–1657 (2000).

It has long been understood that ion acceleration in laser-produced plasma relates to the hot electrons. See, e.g., S. J. Gitomer et al., "*Fast ions and hot electrons in the laser-plasma interaction*", Phys. Fluids, 2679–2686 (1986). A laser pulse interacting with the high density hydrogen-rich material (plastic) ionizes it and subsequently interacts with the created plasma (collection of free electrons and ions). The commonly recognized effect responsible for ion acceleration is a charge separation in the plasma due to high-energy electrons, driven by the laser inside the target (see, e.g., A. Maksimchuk et al., Id., and W. Yu et al., "*Electron Acceleration by a Short Relativistic Laser Pulse at the Front of Solid Targets*", Phys Rev. Lett., 570–573(2000)) or/and an inductive electric field as a result of the self-generated magnetic field (see, e.g., Y. Sentoku et al., "*Bursts of Superreflected Laser Light from Inhomogeneous Plasmas due to the Generation of Relativistic Solitary Waves*", Phys. Rev. Lett., 3434–3437 (1999)), although a direct laser-ion interaction has been discussed for extremely high laser intensities, on the order of $10^{22}$ W/cm$^2$; see, e.g., S. V. Bulanov et al, "*Generation of Collimated Beams of Relativistic Ions in Laser-Plasma Interactions*", JETP Letters, 407–411 (2000). These electrons can be accelerated up to multi-MeV energy levels (depending on laser intensity) due to several processes, such as ponderomotive acceleration by propagating laser pulse (W. Yu et al., Id.); resonant absorption in which a part of laser energy goes into creation of a plasma wave which subsequently accelerates electrons (S. C. Wilks and W. L. Kruer, "*Absorption of Ultrashort, ultra-intense laser light by solids and overdense plasmas*" IEEE J. Quantum Electron., 1954–1968 (1997)); and "vacuum heating" due to the v×B component of the Lorentz force (W. L. Kruer and K. Estabrook, "*J×B heating by very intense laser light,*" Phys. Fluids, 430–432 (1985)). Because of the number of mechanisms for electron acceleration and the corresponding electric field generation, different regimes of ion acceleration are possible. Understanding the mechanisms of ion acceleration in the interaction of laser pulse with a solid target and quantification of the ion yield in terms of the dependencies on the laser pulse and the plasma parameters are useful for designing laser proton therapy systems.

Having the quantified ion yield of a laser-accelerated proton ion beam alone is typically insufficient for preparing a therapeutically-suitable proton ion dose. Such proton ion beams have a wide energy distribution that further require energy distribution shaping (i.e., the resulting high energy polyenergetic ion beam) to be therapeutically suitable. In addition to needing to shape the polyenergetic beam's energy distribution, beam size, direction and overall intensity need to be controlled to provide proton beams that are therapeutically sufficient for irradiating a target in a patient. Lower-energy protons typically treat shallower regions in a patient's body, whereas higher-energy protons treat deeper regions. Thus, there remains the problem of providing systems and methods for forming therapeutically-suitable polyenergetic ion beams from sources of laser-accelerated high energy protons that are capable of treating a predetermined three dimensional conformal region within a body. Such ion selection systems are presently needed to provide low-cost, compact, ion therapy systems to enable the greater availability of positive ion beam therapy to society.

SUMMARY OF THE INVENTION

The present inventor has now designed ion selection systems for forming therapeutically-suitable polyenergetic ion beams. In a first aspect of the present invention there are provided ion selection systems, having a collimation device capable of collimating a laser-accelerated high energy polyenergetic ion beam, the laser-accelerated high energy polyenergetic ion beam including a plurality of high energy polyenergetic positive ions; a first magnetic field source capable of spatially separating the high energy polyenergetic positive ions according to their energy levels; an aperture capable of modulating the spatially separated high energy polyenergetic positive ions; and a second magnetic field source capable of recombining the modulated high energy polyenergetic positive ions.

The present inventor has also designed methods of forming high energy polyenergetic positive ion beams from laser-accelerated high-energy polyenergetic ion beam sources that are suitable for ion beam therapy. Thus, in a second aspect of the present invention there are provided methods of forming a high energy polyenergetic positive ion beam, including the steps of forming a laser-accelerated high energy polyenergetic ion beam including a plurality of high energy polyenergetic positive ions, the high energy polyenergetic positive ions characterized as having a distribution of energy levels; collimating the laser-accelerated ion beam using a collimation device; spatially separating the high energy positive ions according to their energy levels using a first magnetic field; modulating the spatially separated high energy positive ions using an aperture; and recombining the modulated high energy polyenergetic positive ions using a second magnetic field.

Within additional aspects of the invention there are provided laser-accelerated high energy polyenergetic positive ion therapy systems that are capable of delivering therapeutic polyenergetic beams to a three-dimensional conformal target in a body. In these aspects of the invention there are provided laser-accelerated high energy polyenergetic positive ion therapy systems, including: a laser-targeting system, the laser-targeting system having a laser and a targeting system capable of producing a high energy polyenergetic ion beam, the high energy polyenergetic ion beam including high energy positive ions having energy levels of at least about 50 MeV; an ion selection system capable of producing a therapeutically suitable high energy polyenergetic positive ion beam from a portion of the high energy positive ions; and an ion beam monitoring and control system.

In another aspect of the invention, there are provided methods of treating patients with a laser-accelerated high energy polyenergetic positive ion therapy system, including the steps of identifying the position of a targeted region in a patient; determining the treatment strategy of the targeted region, the treatment strategy including determining the dose distributions of a plurality of therapeutically suitable high energy polyenergetic positive ion beams for irradiating the targeted region; forming the plurality of therapeutically suitable high energy polyenergetic positive ion beams from a plurality of high energy polyenergetic positive ions, the high energy polyenergetic positive ions being spatially separated based on energy level; and delivering the plurality of therapeutically suitable high energy polyenergetic positive ion beams to the targeted region according to the treatment strategy.

In a related aspect of the invention, there are provided laser-accelerated ion beam treatment centers, including: a location for securing a patient; a laser-accelerated high energy polyenergetic positive ion therapy system capable of delivering a therapeutically suitable polyenergetic positive ion beam to a patient at the location, the ion therapy system having a laser-targeting system, the laser-targeting system having a laser and at least one target assembly capable of producing a high energy polyenergetic ion beam, the high energy polyenergetic ion beam including high energy polyenergetic positive ions having energy levels of at least about 50 MeV; an ion selection system capable of producing a therapeutically suitable high energy polyenergetic positive ion beam using the high energy polyenergetic positive ions, the high energy polyenergetic positive ions being spatially separated based on energy level; and a monitoring and control system for the therapeutically suitable high energy polyenergetic positive ion beam.

In additional aspects of the present invention there are provided methods of producing radioisotopes using the laser-accelerated high energy polyenergetic ion beams provided herein. In these aspects of the present invention there are provided methods of producing radioisotopes, including the steps of forming a high energy polyenergetic positive ion beam, including forming a laser-accelerated ion beam having a plurality of high energy positive ions, the high energy polyenergetic positive ions characterized as having an energy distribution; collimating the laser-accelerated high energy polyenergetic ion beam using at least one collimation device; spatially separating the high energy polyenergetic positive ions according to energy using a first magnetic field; modulating the spatially separated high energy polyenergetic positive ions using an aperture; recombining the spatially separated high energy polyenergetic positive ions using a second magnetic field; and irradiating a radioisotope precursor with the recombined spatially separated high energy polyenergetic positive ions.

Other aspects of the present invention will be apparent to those skilled in the art in view of the detailed description of the invention as provided herein.

BRIEF DESCRIPTION OF THE DRAWINGS

The foregoing summary, as well as the following detailed description, is further understood when read in conjunction with the appended drawings. For the purpose of illustrating the invention, there is shown in the drawings exemplary embodiments of the invention; however, the invention is not limited to the specific methods and instrumentalities disclosed. In the drawings:

FIG. 3 shows the proton spatial distributions $N=N(y)$ per laser pulse for a given number of the total protons simulated versus y-axis at the plane x=40 cm, z=0 cm, for a primary collimator opening of 1×1 cm$^2$ defined at 100 cm source to surface distance ("SSD"). N represents the number of protons in a given range of spatial y-coordinate. The solid line represents protons in the energy range $80 \leq E \leq 90$ MeV, the dotted line represents protons in the energy range $110 \leq E \leq 120$ MeV, the dashed line represents protons in the energy range $140 \leq E \leq 150$ MeV, the dashed-dotted line represents protons in the energy range $190 \leq E \leq 200$ MeV and the dashed-two dotted line represents protons in the energy range $250 \leq E \leq 260$ MeV.

FIG. 6(*a*) shows the proton spatial distributions N=N(y) versus y-axis at the plane x=40 cm, z=0 cm, for a primary collimator opening of 5×5 cm² defined at 100 cm SSD. The solid line represents protons in the energy range 80≦E≦90 MeV, the dotted line represents protons in the energy range 110≦E≦120 MeV, the dashed line represents protons in the energy range 140≦E≦150 MeV, the dashed-dotted line represents protons in the energy range 180≦E≦190 MeV and the dashed-two dotted line represents protons in the energy range 245≦E≦255 MeV.

FIG. 6(*b*) shows the proton energy distributions N=N(E) versus energy at plane x=40 cm, z=0 cm, for a primary collimator opening of 5×5 cm² defined at 100 cm SSD. The solid line represents protons with energy distribution peaked at E=76 MeV, the dotted line represents protons with energy distribution peaked at E=95 MeV, the dashed line represents protons with energy distribution peaked at E=133 MeV, the dashed-dotted line represents protons with energy distribution peaked at E=190 MeV and the dashed-two dotted line represents protons with energy distribution peaked at E=208 MeV.

FIG. 9(*b*) shows the SOBP dose distribution with a 4×4 cm² field normalized to the initial fluence of protons. The solid line represents the dose distribution calculated using 16 1×1 cm² beamlets with the spectrum shown in FIG. 9(*a*) (solid line). The dashed line represents the dose distribution calculated using a spectrum of ideal mono-energetic protons. One-standard deviation associated with the calculations is on the order of 1%.

FIG. 13 shows the angular distribution of laser-accelerated protons, relative number per radian (top) and maximum proton energy as a function of laser pulse length (bottom) for a laser intensity of $10^{21}$ W/cm².

FIG. 14 shows Laser-accelerated proton energy spectra collimated by a small aperture (top) and dose distributions from these spectra (bottom) for a laser intensity of $10^{21}$ W/cm² and 50 fs pulse length.

FIG. 15 shows depth dose curves of protons of different energy levels and intensities to form a SOBP (top) using monoenergies (solid) or the spectra in FIG. 14 (dashed), and the weight of each energy spectrum for the spectrum-based SOBP (bottom).

FIG. 31($b$) depicts a schematic illustration of a collimator 2 (i.e., a multileaf collimator) in the x–z plane showing openings in the collimator for selecting positive ions of a particular energy.

FIG. 33 depicts a schematic illustration of a multileaf collimator in the x–z plane: ($a$) shows openings in the multileaf collimator for selecting low energy ions; ($b$) shows openings in the multileaf collimator for selecting high energy ions.

FIG. 42($b$) depicts a perspective view of an embodiment of a laser-accelerated high energy polyenergetic positive ion beam treatment center that includes an optical monitoring and control system.

FIG. 42($c$) depicts a perspective view of an embodiment of a laser-accelerated high energy polyenergetic positive ion beam treatment center that includes more than one ion therapy system.

FIG. 42($d$) depicts a perspective view of an embodiment of a laser-accelerated high energy polyenergetic positive ion beam treatment center that includes more than one ion therapy system, with each of the ion therapy systems having an optical monitoring and control system.

DETAILED DESCRIPTION OF ILLUSTRATIVE EMBODIMENTS

Figure 1:
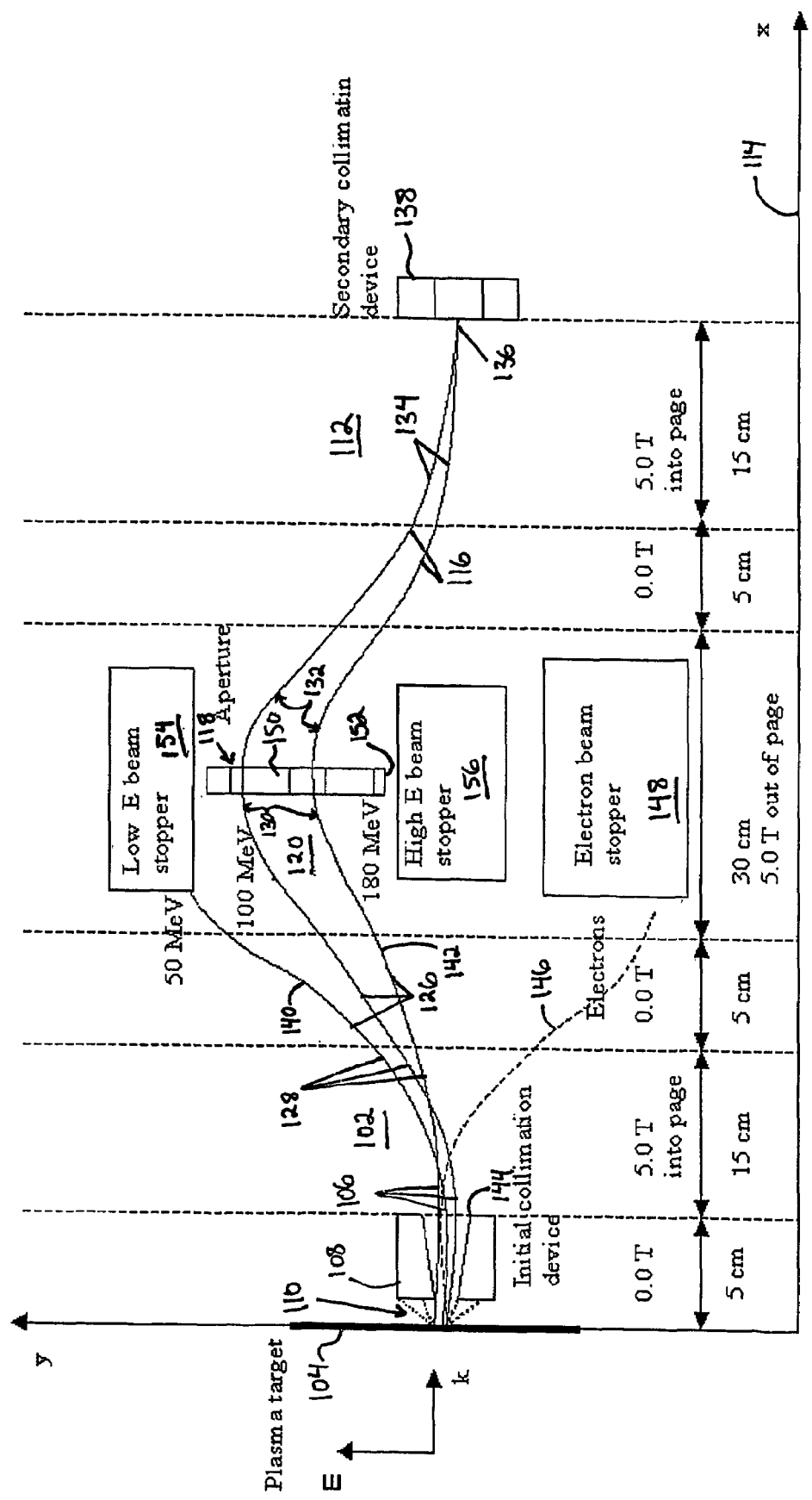
FIG. 1 is a schematic diagram of one embodiment of the polyenergetic ion selection system of the present invention. E represents the electric field of the pulse polarized along the y-axis. k is the wave vector of the pulse directed along the x-axis. The pulse is initialized to the left of the target and propagates from the left to the right side of the diagram.

The following abbreviations and acronyms are used herein:

CORVUS a treatment optimization system for photon IMRT from NOMOS
CPA chirped pulse amplification
CT computer-aided tomography
DICOM Digital Imaging and Communications in Medicine
DICOM RT DICOM Radiation Therapy Supplement
DVH dose-volume histogram
EIMPT energy- and intensity-modulated proton therapy
EGS4 Electron Gamma Shower (version 4) Monte Carlo code system
GEANT(3) a Monte Carlo system for radiation (proton, neutron, etc) simulation
IMRT intensity-modulated (photon) radiation therapy
JanUSP a high power ($10^{19}$–$10^{21}$ W/cm$^2$) laser at LLNL
LLNL Lawrence Livermore National Laboratory
LLUMC Loma Linda University Medical Center, Loma Linda, Calif.
MCDOSE an EGS4 user-code for dose calculation in a 3-D geometry
MGH Massachusetts General Hospital, Boston, Mass.
MLC multileaf collimator
NOMOS NOMOS Corp., Sewickley, Pa.
NTCP normal tissue complication probability
PC personal computer
PIC particle-in-cell (simulation technique for laser plasma physics)
PMC primary monitor chamber
PSA prostate-specific antigen
PTV planning target volume
PTRAN a Monte Carlo code system for proton transport simulation
RTP radiotherapy treatment planning
SMC secondary monitor chamber
SOBP spread out Bragg peak (for proton/ion beams)
SSD source-surface distance
TCP tumor control probability
MeV million electron volts
GeV billion electron volts
T Tesla As used herein, the term "protons" refers to the atomic nuclei of hydrogen ($H^1$) having a charge of +1.

As used herein, the term "positive ions" refers to atoms and atomic nuclei having a net positive charge.

As used herein, the term "polyenergetic" refers to a state of matter being characterized as having more than one energy level.

As used herein, the term "high energy" refers to a state of matter being characterized as having an energy level greater than 1 MeV.

As used herein, the term "beamlet" refers to a portion of a high energy polyenergetic positive ion beam that is spatially separated, or energetically separated, or both spatially and energetically separated.

The terms "primary collimator", "primary collimation device", "initial collimator", and "initial collimation device" are used interchangeably herein.

The terms "energy modulation system" and "aperture" are used interchangeably when it is apparent that the aperture referred to is capable of modulating a spatially separated high energy polyenergetic positive ion beam.

All ranges disclosed herein are inclusive and combinable.

In one embodiment of the present invention there is provided a laser-accelerated polyenergetic ion selection system for radiation therapy. The design of this system typically includes a magnetic field source that is provided to spatially separate protons of different energy levels. A magnetic field source is also provided to separate out plasma electrons that initially travel with the protons. While these two magnetic field sources are typically provided by the same magnetic field source, two or more separate magnetic field sources may be provided to carry out these functions. After the protons have been spatially separated, one or more apertures are typically provided to select an energy distribution needed to cover the treatment target in the depth direction for a given beamlet. The form of an aperture is dictated by the location as well as the depth dimension of the target, as described more fully below. Once the spatial position and the target size are known, the proton energy spectrum needed to cover the target for a given beamlet in the depth direction is calculated by combining the depth dose curves of different proton energy levels, as described more fully below. Due to the angular distribution of protons, a primary collimation device is typically employed to reduce spatial mixing of different energy protons. The primary collimation device is typically employed to collimate the positive ions into a magnetic field that separates the ions by energy levels. As a result of this spatial mixing, the proton energy spectrum in a given spatial location typically has a small spread that depends on the energy of the protons. The depth dose curves are typically calculated using the spread out (i.e., polyenergetic) proton spectrum. In this regard, the depth dose curves for the proton energy modulation are typically modified to account for this polyenergetic spreading effect, as described more fully below.

Description of a proton selection and collimation system:
In one embodiment of the present invention there is provided an ion selection and collimation device needed for proton energy modulation. Using the 2D particle in cell simulation code (PIC), described by C. K. Birdsall and A. B. Langdon in *Plasma Physics via Computer Simulation* (McGraw-Hill Book Company, Singapore 1985), the interaction of a petawatt laser pulse with a thin dense foil (hydrogen rich) was simulated, yielding protons with energy well beyond 200 MeV and maximum energy reaching 440 MeV. The simulations were performed for a 3.6 µm (in the radial direction) full width at half-maximum (FWHM, 14 femtosecond (fs) linearly polarized laser pulse with a wavelength, $\lambda=0.8$ µm and intensity $I=1.9\times10^{22}$ W/cm², normally incident onto a thin dense plasma slab (ionized foil) with a density thirty times higher than the critical density $n_{cr}=4\pi^2 m_e c^2\epsilon_0/(e^2\lambda^2)$ and thickness $d\approx1$ µm. Such la reach of the recent technological developments, as described by G. A. Mourou et al., in "*Ultrahigh-Intensity Lasers: Physics of the Extreme on a Tabletop*", Physics Today, 22–28 (1998). The basic configuration of such as laser light source system is described in U.S. Pat. No. 5,235,606, issued Aug. 10, 1993 to Mourou et al., which is incorporated by reference herein. U.S. patent application Ser. No. 09/757,150 filed by Tajima on Jan. 8, 2001, Pub. No. U.S. 2002/0090194 A1, Pub. Date Jul. 11, 2002, "Laser Driven Ion Accelerator" discloses a system and method of accelerating ions in an accelerator using such a laser light source system, the details of which are incorporated by reference herein in their entirety.

The protons coming from a thin foil are typically accelerated in the forward direction by the electrostatic field of charge separation induced by the high intensity laser. Further details of this process are described by V. Yu. Bychenkov et al., in "*High energy ion generation in interaction of short laser pulse with solid density plasma*", Appl. Phys. B, 207–215 (2002). Over a period of several tens of plasma frequency $\omega_p=\sqrt{ne^2/m_e\epsilon_0}$ cycles, protons are typically accelerated to relativistic energy levels. The maximum value of the proton energy levels typically depend on several factors, including laser pulse length and intensity, and plasma foil thickness. The late time dynamics can be discerned by PIC code, which shows that protons reach a stationary distribution (energy, angular) and move in a formation together with the electrons. This reassures the preservation of the low proton emittance, shielding proton space charge, which otherwise could be detrimental to the emittance. The angular distribution of protons exhibits the spread which depends on the energy. Typically, the general trend is such that the higher the energy of the accelerated protons, the more they are emitted in the forward direction. The depth dose distribution calculated using the laser-accelerated proton spectrum shows that the polyenergetic positive ion spectrum emitted from the target typically cannot be readily used for radiation treatments. A high energy deposition to the area beyond the effective Bragg peak typically arises from the high entrance dose to the superficial structures and the long tails in the polyenergetic dose distributions. Thus, in one embodiment of the present invention, one delivers a homogeneous dose to the tumor volume to minimize the dose to the surrounding healthy tissues. This is achieved by providing an ion (e.g., proton) selection and collimation device that generates the desired polyenergetic proton energy distribution. This device separates polyenergetic positive ions (e.g., protons) into spatial regions according to their energy. The spatially separated regions of the positive ions are subsequently controlled using at least one magnetic field. The spatially separated positive ions are controllably modulated using an aperture to provide the desired dose. Optionally, the device also includes a magnetic field source for generating a magnetic field to eliminate the plasma electrons that travel with the positive ions. This optional magnetic field source can be the same or a different magnetic field as the one spatially separating the polyenergetic positive ions. This magnetic field is also useful for eliminating plasma electrons traveling together with the laser-accelerated positive ions.

A schematic diagram of one embodiment of the ion selection system (100) is provided in FIG. 1. Referring to this figure, there is provided a series of magnetic field sources that produce a magnetic field pattern $B=B(z)e_z$, the z-direction being perpendicular to the page. A first magnetic field source provides a first magnetic field (102), listed as "5.0 T into page", at a distance from 5 cm to 20 cm from a plasma target (104) located at 0 cm along the x (primary beam) axis (114). High energy polyenergetic positive ions (110) are generated by the interaction between the plasma target (104) with a suitable laser pulse (not shown). A beam of high energy polyenergetic positive ions (e.g., protons) (106) enter the first magnetic field (102) after exiting an initial collimation device (108). The protons are shown exiting the initial collimation device (108) into the first magnetic field (102), the protons being characterized as having an angular spread. A second magnetic field (112)

source provides a second magnetic field listed as "5.0 T into page" at a distance from 60 cm to 75 cm from the plasma target (104) along the x (primary beam) axis (114). High energy polyenergetic positive ions (116) (protons in certain embodiments) enter the second magnetic field (112) after exiting an aperture (118). Also shown in FIG. 1 is a third magnetic field source providing a third magnetic field (120), which is listed as "5.0 T out of page" at a distance from 25 cm to 55 cm from the plasma target (104) located at 0 cm along the x axis (114). The x axis as drawn is parallel to the beam axis (114) of the laser in this embodiment. Other coordinate orientations and coordinate systems, such as cylindrical and spherical coordinate systems, can be suitably used. High energy polyenergetic positive ions (126) enter the third magnetic field (120) after exiting the first magnetic field (102). The first magnetic field (102) is shown spatially separating the trajectories (128) of the high energy polyenergetic positive ions by energy level. The third magnetic field (120) is shown bending the trajectories of spatially separated ions (130) towards the aperture (118). The aperture modulates the ion beam by controllably selecting a portion of the spatially separated ions, as described further herein. The third magnetic field (120) is also shown bending the trajectories of the spatially separated polyenergetic positive ions (132) towards the beam axis and towards the second magnetic field (112). The second magnetic field (112) recombines the spatially separated and modulated ions (134) to form a recombined ion beam (136). The recombined ion beam (136) is shown entering a secondary collimation device (138). Upon exiting the secondary collimation device (138), a high energy polyenergetic positive ion beam is provided that is suitable for use in high energy polyenergetic positive ion radiation therapy. Suitable magnetic field sources for this and various embodiments of the present invention typically have a magnetic field strength in the range of from about 0.1 to about 30 Tesla, and more typically in the range of from about 0.5 to about 5 Tesla. The Lorentz force of the magnetic field typically spreads out the polyenergetic protons. The lower energy protons (140) typically are deflected more from their original trajectories exiting the initial collimation device 108) ("initial collimator") than are the high energy protons (142).

As described herein, many of the embodiments of the present invention use magnetic field sources to provide magnetic fields for manipulating the positive ion beams. In additional embodiments of the present invention one or more of the magnetic field sources are replaced by, or combined with, one or more electrostatic field sources for manipulating the positive ion beams.

The initial collimator (108) typically defines the angular spread of the incoming beam (106) entering the first magnetic field (102). The tangent of the angle of the beam spread of the beam (106) exiting the initial collimator (108) is typically about the ratio of one half the distance of the initial collimator exit opening (144) where the beam exits the collimator to the distance of the collimator exit opening (144) to the proton beam source (i.e., the plasma target, 104). Typically, this angle is less than about 1 radian. The emitting angle is the angle of the initial energy distribution exiting the target system (i.e., target, 104 and initial collimation device, 108). Electrons (146) are typically deflected in the opposite direction from the positive ions by the first magnetic field and absorbed by a suitable electron beam stopper (148). Suitable electron stoppers (148) include tungsten, lead, copper or any material of sufficient thickness to attenuate the electrons and any particles they generate to a desired level. The aperture (118) is typically used to select the desired energy components, and the matching magnetic field setup (in this embodiment, the second magnetic field, 112) is selected that is capable of recombining the selected protons (134) into a polyenergetic positive ion beam. Suitable apertures typically can be made from tungsten, copper or any other materials of sufficient thickness that are capable of reducing the energy levels of positive ions. This energy level reduction is typically carried out to such a degree that the positive ions can be differentiated from those ions that do not go through the aperture. In various embodiments of the present invention, the aperture geometry can be a circular, rectangular, or irregular-shaped opening (150)(or openings) on a plate (152)(or slab), which when placed in a spatially separated polyenergetic ion beam, is capable of fluidically communicating a portion of the ion beam therethrough. In other embodiments, the aperture (118) can be made from a plate that has multiple openings that are controllably selected, such as by physical translation or rotation into the separated ion beam to spatially select the desirable energy level or energy levels to modulate the separated ion beam. The modulation of the ion beam gives rise to a therapeutically suitable high energy polyenergetic positive ion beam (136) as described herein. Suitable apertures include multi-leaf collimators. In addition to controllably selecting the spatial position of the openings that fluidically communicate the spatially separated ion beams, the aperture openings may also be controllably shaped or multiply shaped, using regular or irregular shapes. Various combinations of openings in the aperture (118) are thus used to modulate the spatially separated ion beam (130). The spatially separated positive ions (132) are subsequently recombined using the second magnetic field (134).

The high and low energy positive ion (e.g., proton beam) stoppers (154 and 156, respectively) typically eliminate unwanted low-energy particles (140) and high-energy particles (not shown). Because of the broad angular distribution of the accelerated protons (which depends on a given energy range), there is typically a spatial mixing of different energy positive ions after they pass through the first magnetic field. For example, a portion of the low energy protons may go to regions where the high energy particles reside, and vice versa. Reducing the spatial mixing of protons is typically carried out by introducing a primary collimation device, such as the initial collimation device 108 of the embodiment depicted in FIG. 1. A primary collimation device is typically used to collimate protons to the desired angular distribution.

As described further below, proton spatial differentiation is typically carried out by passing the positive ions through a small collimator opening prior to their entering the first magnetic field. An example of a small collimator opening is depicted in FIG. 1 as the initial collimator opening (144). Typically, the collimator exit opening (144) is not arbitrarily small, since smaller openings typically lower the dose rate and increase the treatment time. As a result of the finite size of the collimator opening (144), the protons are typically spatially mixed. Accordingly, any given spatial location for a collimator opening (however small) typically provides a polyenergetic proton energy distribution. While not being bound by any particular theory of operation, the energy modulation calculations take into account the polyenergetic characteristics of the positive ions entering the ion selection device to provide the needed depth dose curves. The polyenergetic characteristics of these positive ions is understood through the influence of the magnetic field on the dynamics of the positive ions. The following description is directed to the dynamics of protons, as one illustrative embodiment. Additional embodiments to other positive ions in addition to protons are also envisioned.

To describe the proton's dynamics in the magnetic field, a numerical code is written which solves the following equation of motion, $$\frac{dp_i}{dt} = ev_i \times B \quad (1)$$

where $p=m_p v/\sqrt{1-v^2/c^2}$, B is the magnetic induction vector, $m_p$ is the proton rest mass and i signifies the particle number. For one embodiment of the present invention, this equation was solved using a symplectic integration algorithm developed by J. Candy and W. Rozmus in "*A Symplectic Integration Algorithm for Separable Hamiltonian Functions* ", J. Comp. Phys. 230–239 (1991). The initial conditions [$(r_0^i, v_0^i)$] were obtained from the PIC simulation data, which provided the phase-space distribution for protons. The contribution of the self-consistent fields on the proton dynamics were neglected, since the Lorentz force created by the external magnetic field to separate the electrons from the protons is greater for the magnetic field induction used in the calculations than the Coulomb force in the region beyond the initial collimation device. Using the equation of balance between the Lorentz and the inter-particle Coulomb forces, one arrives at a condition for particles spatial separation distance for which the magnetic force prevails over the Coulomb force, $$r > \left(\frac{e}{4\pi\varepsilon_0 Bv}\right)^{1/2} \quad (2)$$

where B is the magnitude of the magnetic field, v is the particle velocity and e is an elementary charge. The average inter-particle distance r can be obtained from the particle density $r=n^{-1/3}$, thus the inequality (2) can be rewritten in the form:

$$n < \left(\frac{4\pi\varepsilon_0 Bv}{e}\right)^{3/2} \quad (3)$$

Providing the lowest therapeutic energy protons of about 50 MeV, which corresponds to proton velocity of v=0.3c, and the magnetic field induction B=5 T, the condition (3) gives, $n<2*10^{20}$ cm$^{-3}$. The particle density in the region beyond the initial collimation device can be estimated using the arguments presented by E. Fourkal et al. in "*Particle in cell simulation of laser-accelerated proton beams for radiation therapy*", Id. (2002). In this region the particle density is $n=4*10^{13}$ cm$^{-3}$, which is far below the estimated threshold value of $2*10^{20}$ cm$^{-3}$. This estimate validates the assumption of the insignificant contribution of the self-consistent electrostatic field on the proton dynamics in the external magnetic field.

The calculations of the proton dynamics in the magnetic field have also neglected such boundary effects as edge focusing due to the influence of the fringing field patterns at the edge of a sector field. These effects are expected to be small in the bulk of the selection system due to the canceling action of alternating magnetic field patterns (with the same absolute value of the field induction). As the positive ions (e.g., protons) leave the final field section, the boundary fringe field can introduce some focusing effect. This effect can be accounted for by using the magnetic field distribution at the boundary.

Monte Carlo calculations: While not being bound by any particular theory of operation, the GEANT3 Monte Carlo radiation transport code is used for dose calculations. GEANT3 is used to simulate the transport and interactions of different radiation particles in different geometries. The code can run on different platforms. A detailed description of the operation and usage of GEANT3 has been given by R. Brun et al., in *GEANT3—Detector description and simulation tool Reference Manual* (1994). GEANT3 is equipped with different user selectable particle transport modes. Being more versatile than most Monte Carlo codes concerning the production of secondaries, GEANT3 has three options to deal with these rays. An important user controlled variable for these options is DCUTE below which the secondary particle energy losses are simulated as continuous energy loss by the incident particle, and above it they are explicitly generated. In the first option, the secondary particles are produced over the entire energy range of the incident particle. This mode is termed as "no fluctuations". The second mode of energy loss is "full fluctuations", in which secondaries are not generated, and the energy loss straggling is sampled from a Landau ("*On the energy loss of fast particles by ionization*", J. Phys. USSR, 201–210 (1944)), Vavilov ("*Ionisation losses of high energy heavy particles*", Soviet Physics JETP, 749–758 (1957)) or Gaussian distribution each according to its validity limits (R. Brun et al., Id.). The third is "restricted fluctuations", with generation of secondaries above DCUTE and restricted Landau fluctuations below DCUTE. In principle, choosing energy loss fluctuations typically carries an advantage if energy deposited is scored in voxel sizes larger than the range of secondaries. This results in great savings of computation time and avoids tracking a large number of secondaries generated below DCUTE. Typically, a continuous energy loss by the incident particle is assumed according to the Berger-Seltzer formulae.

Moliere multiple scattering theory is used by default in GEANT3. Multiple scattering is well described by Moliere theory. See, e.g., G. Z. Moliere, "*Theorie der Streuung schneller geladener Teilchen I: Einzelstreuung am abgeschirmten Coulomb-Feld*", Z. Naturforsch., a, 133–145 (1947); and G. Z. Moliere, "*Theorie der Streuung schneller geladener Teilchen II: Mehrfach-und Vielfachstreuung*", Z. Naturforsch., a, 78–85 (1948). A limiting factor in the Moliere theory is the average number of Coulomb scatters $\Omega_0$ for a charged particle in a step. When $\Omega_0<20$, the Moliere theory is typically not applicable. According to E. Keil et al. in "*Zur Eifach-und Mehrfachstreuung geladener Teilchen*", Z. Naturforsch, a, 1031–1048 (1960), the range $1<\Omega_0\leq 20$ is called the plural scattering regime. In this range a direct simulation method is used for the scattering angle in GEANT3 (R. Brun et al., Id.). A simplification of the Moliere theory by a Gaussian form is also implemented in GEANT3. The Gaussian multiple scattering represents Moliere scattering to better than 2% for $10<\Omega_0\leq 10^8$.

The hadronic interactions in matter (elastic, inelastic, nuclear fission, neutron nuclear capture) are described by two software routines, GHEISHA and FLUKA, which are available to users of GEANT. The GHEISHA code generates hadronic interactions with the nuclei of the current tracking medium, evaluating cross-sections and sampling the final state kinematics and multiplicity, while the GEANT philosophy is preserved for the tracking purposes. A number of routines that exist in GHEISHA are responsible for generating the total cross-sections for hadronic interactions, calculating the distance to the next hadronic interaction according to the total cross-sections and finally the main steering routine for the type of occurred hadronic interaction. FLUKA is a simulation program, which as a standalone code contains transport and the physical processes for hadrons and leptons and tools for geometrical description. In GEANT, only the hadronic interaction part is included. As with the GHEISHA package, the FLUKA routines can compute the total cross-sections for hadronic processes, and perform the sampling between elastic and inelastic processes. The cross-sections for both types of interactions are computed at the same time as the total cross-section. Subsequently, a particle is sent to the elastic or inelastic interaction routines. After the interaction, the eventual secondary particles are written to the GEANT stack.

The following control parameters were used to calculate the depth dose distributions for proton beams in the example presented herein: The cutoff energy for particles was 20 keV, the Rayleigh effect was considered, δ-ray production was turned on, continuous energy loss for particles below cutoff energy levels sampled directly from the tables, Compton scattering was turned on, pair production with generation of $e^-/e^+$ was considered, photoelectric effect was turned on, and positron annihilation with generation of photons was considered.

Results and Discussion: The PIC simulations show that the maximum proton energy of the polyenergetic proton beam is a function of many variables including the laser pulse intensity and duration, as well as the target density and its thickness. The quantitative dependence of the maximum proton energy on laser/plasma target parameters can be found in Fourkal et al. The overall results of this study showed that the maximum proton energy increases with decreasing thickness of the plasma target reaching the plateau for the target thicknesses on the order of the hot electron Debye length (for a given laser intensity). In the same time, the proton energy is a non-monotonous function of the laser pulse length, reaching the maximum value for the laser-pulse length of the order of 50 femtoseconds. Thus, depending on the simulation parameters, one can obtain a broad spectrum of energy distributions for the accelerated protons.

Figure 2A:
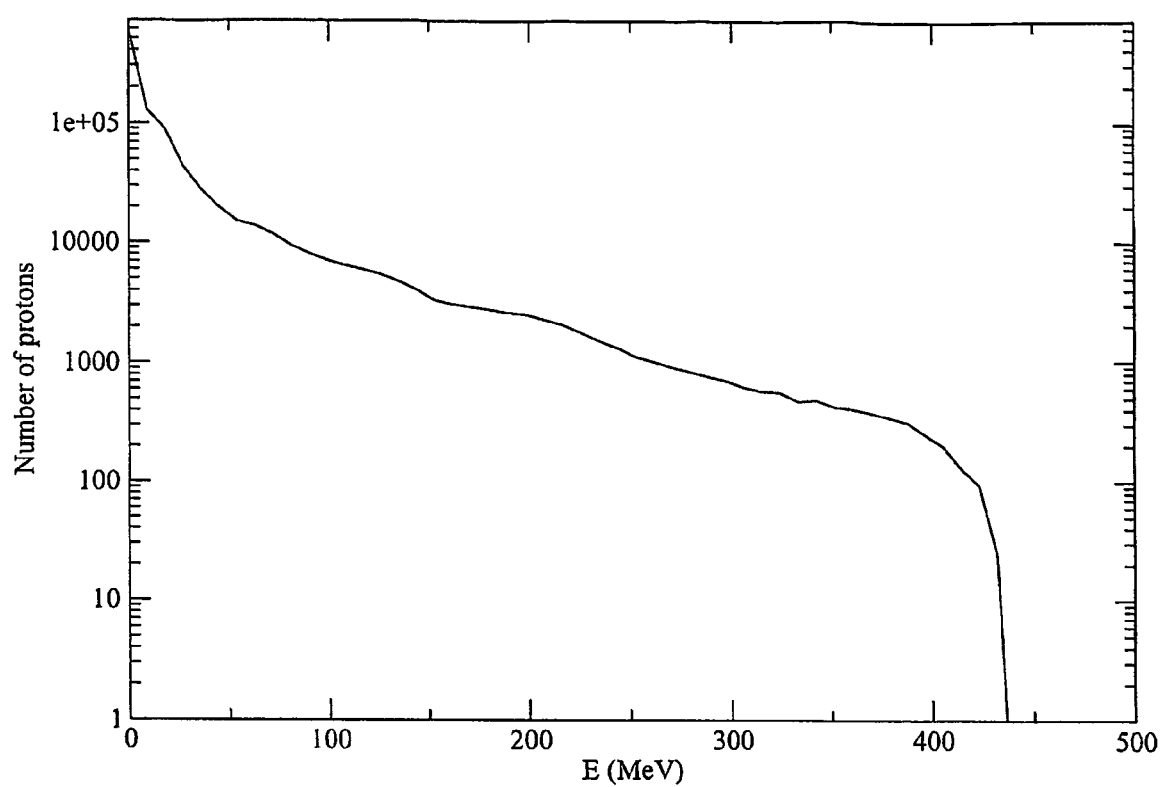
FIG. 2(a) shows the energy distribution of protons at $t=400/\omega_{pe}$. $\omega_{pe}=1.18*10^{15}$ rad/s. N represents the number of protons in a given energy range when the total number of protons used in the simulation is 1048576.
Figure 2B:
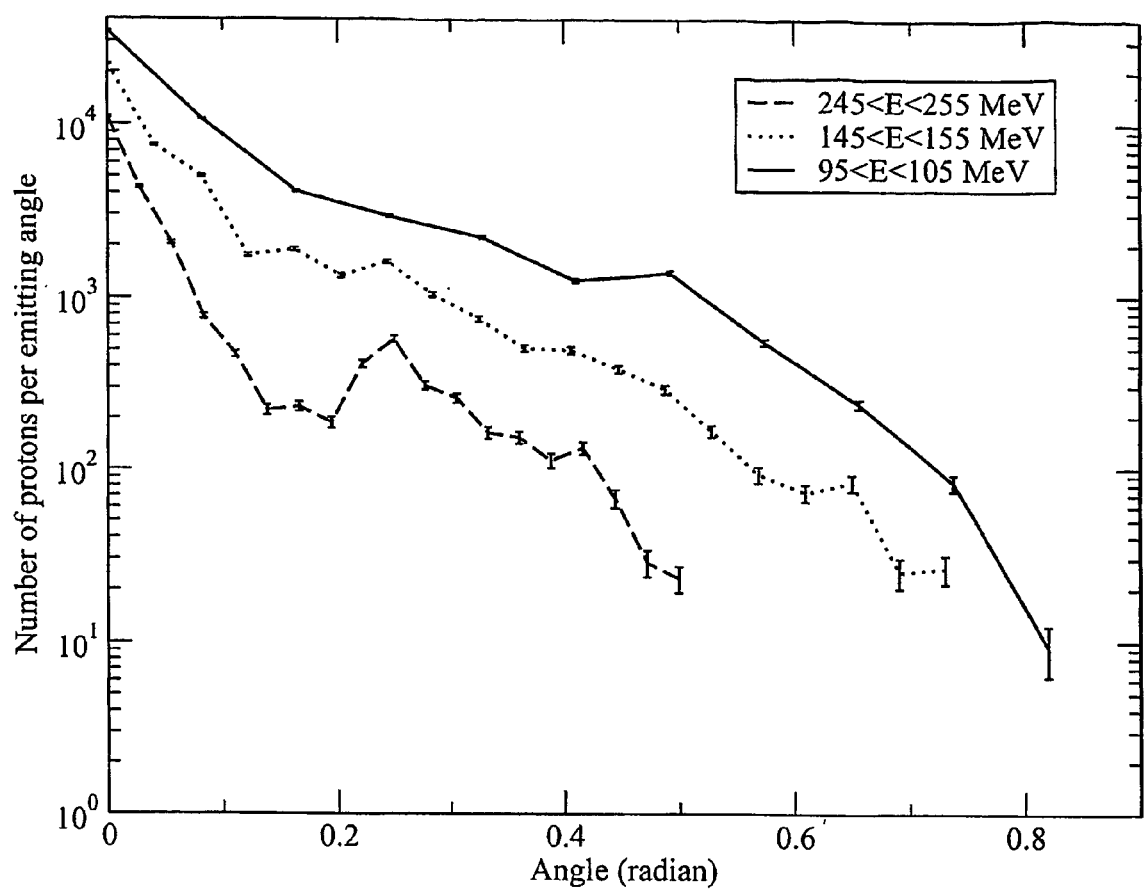
FIG. 2(b) shows the angular distributions of accelerated protons at $t=400/\omega_{pe}$. The solid line shows the distribution for protons in the energy range $95 \leq E \leq 105$ MeV, the dotted line represents the protons in the energy range $145 \leq E \leq 155$ MeV, and the dashed line represent protons in the energy range $245 \leq E \leq 255$ MeV. The laser pulse length and intensity are 14 fs and $I=1.9*10^{22}$ W/cm$^2$ correspondingly. The error bars represent one-standard deviation statistical uncertainty.

FIGS. 2(a) and 2(b) show the energy and angular distributions for the protons accelerated by the laser pulse described above. For the laser/plasma parameters chosen in the simulation, the maximum proton energy reaches the value of 440 MeV, which is much higher than typically needed for radiotherapy applications. To reduce the unwanted protons, as well as to collimate them to a specific angular distribution, a primary collimation device is provided. Its geometrical size and shape is typically tailored to the energy and angular proton distributions. For example, in one embodiment of the present invention there is provided a 5 cm long tungsten collimator that absorbs the unwanted energy components. Because of its density and the requirement for the compactness of the selection system, tungsten is a favorable choice for collimation purposes. A suitable primary collimator opening provides a 1×1 $cm^2$ field size defined at 100 cm SSD. Protons that move into an angle larger than this are typically blocked. With the magnetic field configuration shown in FIG. 1, for example, the solution to the equation of motion (1) with the initial conditions given by the proton phase space spectra obtained from the PIC simulations, yields the proton spatial distributions N=N(y) at the plane x=40 cm, z=0 cm, as shown in FIG. 3.

This shows that the magnetic field spreads the polyenergetic protons into spatial regions according to their energy and angular distributions. Their spatial distribution is such that the lower energy particles are deflected at greater distances away from the central axis, and as the proton energy increases the spatial deflection decreases. Therefore, the contribution of both the magnetic field and the primary collimator (with a specific collimator opening) creates such a spatial proton distribution that allows the energy selection or proton energy spectrum reformation, using an aperture. The geometric shape of an aperture typically determines the energy distribution of the therapeutic protons.

Figure 4:
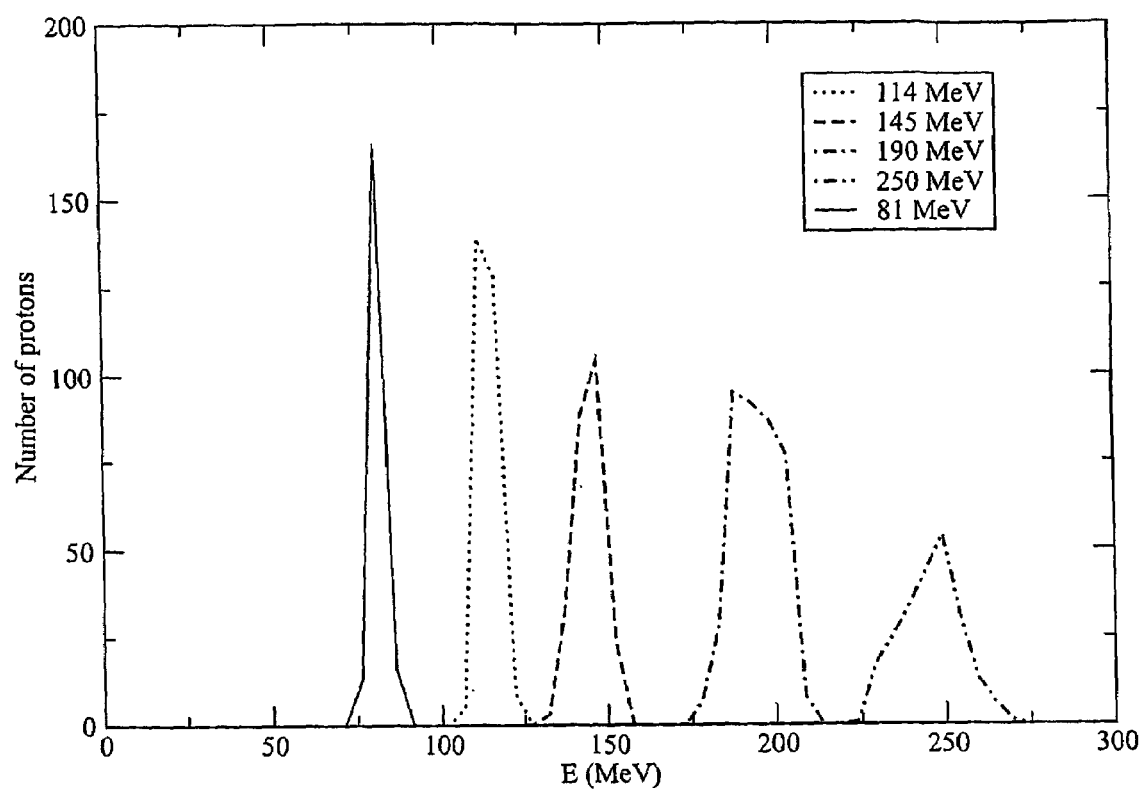
FIG. 4 shows the proton energy distributions $N=N(E)$ per laser pulse for a given number of the total protons simulated versus energy at plane x=40 cm, z=0 cm, for a primary collimator opening of 1×1 cm² defined at 100 cm SSD. The solid line represents protons with energy distribution peaked at E=81 MeV, the dotted line represents protons with energy distribution peaked at E=114 MeV, the dashed line represents protons with energy distribution peaked at E=145 MeV, the dashed-dotted line represents protons with energy distribution peaked at E=190 MeV and the dashed-two dotted line represents protons with energy distribution peaked at E=250 MeV.
Figure 5:
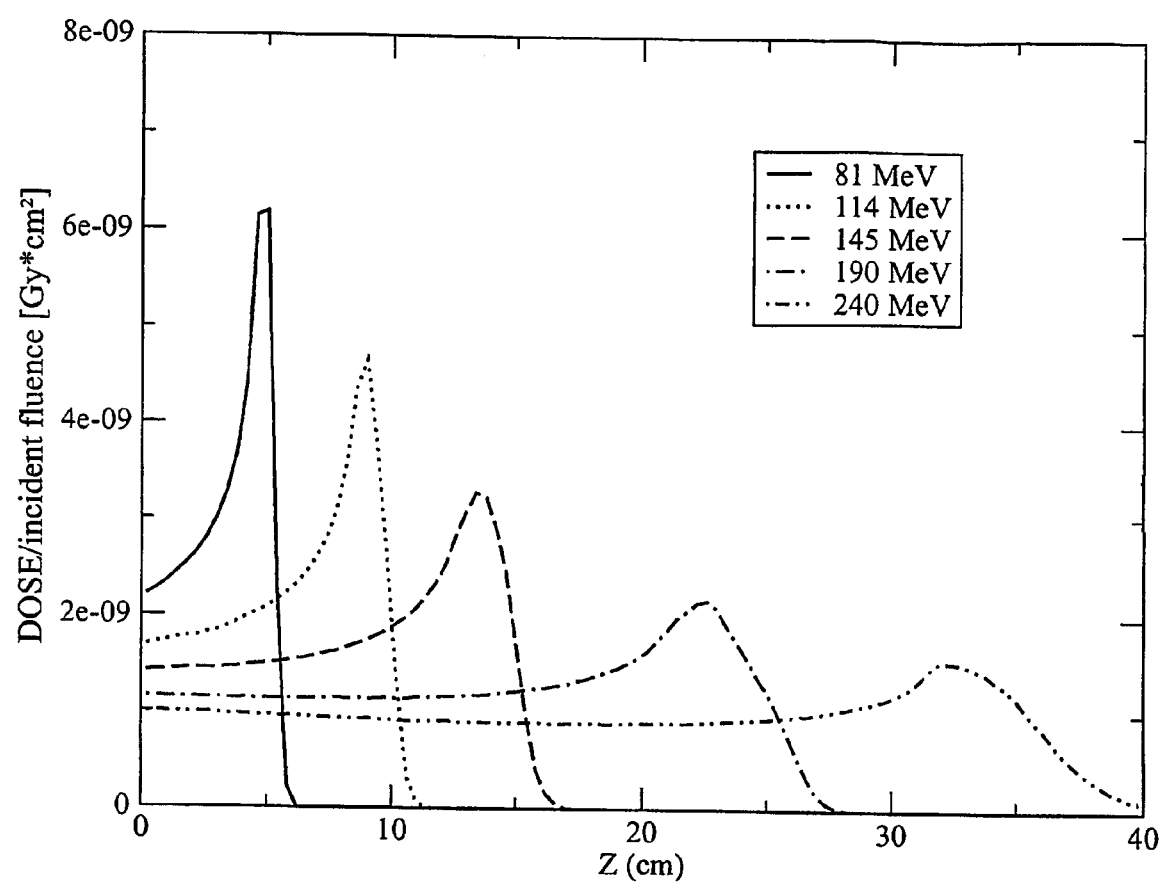
FIG. 5 shows the depth dose distributions for protons with energy spectra shown in FIG. 4 normalized to the initial proton fluence. The solid line represents the dose distribution calculated using the proton spectrum peaked at E=81 MeV, the dotted line represents the dose distribution calculated using the proton spectrum peaked at E=114 MeV, the dashed line represents the dose distribution calculated using the proton spectrum peaked at E=145 MeV, the dashed-dotted line represents the dose distribution calculated using the proton spectrum peaked at E=190 MeV, and the dashed-two dotted line represents the dose distribution calculated using the proton spectrum peaked at E=240 MeV. The primary collimator opening is 1×1 cm² defined at 100 cm SSD. One-standard deviation associated with the calculations is on the order of 1%.

As mentioned above, due to the presence of the angular spread, there is typically a spatial mixing of different energy protons. As a result of this mixing, the proton energy distribution in a given spatial location is typically no longer monochromatic, but has a spread around its peak. FIG. 4 shows the proton energy distributions at different spatial locations. These distributions were calculated by counting the number of protons in the given spatial location of width Δy=3 mm as a function of energy. This figure shows that the lower energy particles have a much smaller spread than the high energy particles. Without being bound to a particular theory of operation, this result is apparently due to the higher energy protons not being deflected as much in the magnetic field as are the lower energy particles. Because of the energy spread effect, the depth dose curves needed for the energy modulation calculations typically are modified to include the effect of the energy spread in the calculations, since mono-energetic protons are not typically for the depth dose calculations. Using the GEANT3 Monte Carlo transport code the dose distributions for the proton energy spectra shown in FIG. 4 for a 4×4 $cm^2$ field size was calculated. The results of the simulation are shown in FIG. 5. The presence of an energy spread in the proton spectra leads to the broadening of the dose distributions, which leads to a less sharp falloff of the energy-modulated Bragg peak as compared to the case of mono-energetic beams. See, e.g., T. Bortfeld. The broadening is typically most profound for the higher energy protons.

Figure 7:
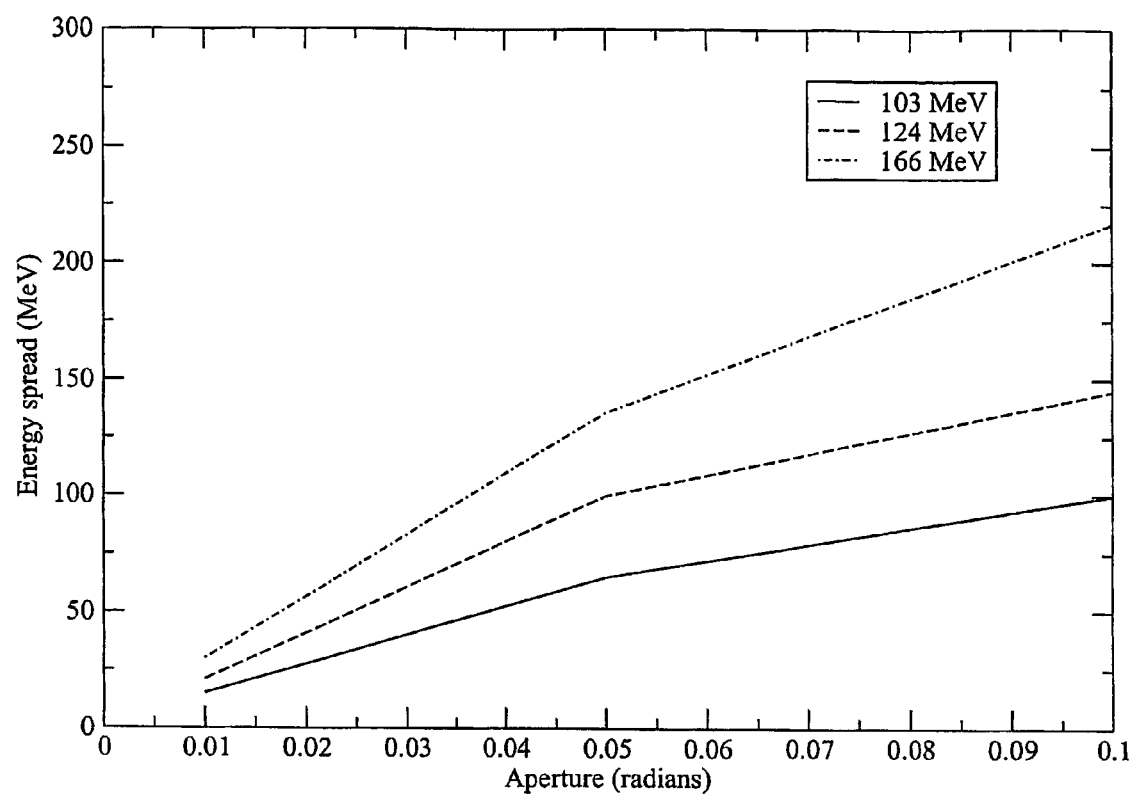
FIG. 7 shows the energy spread versus the primary collimator opening. The solid line corresponds to the protons peaked at energy 103 MeV, the dashed line corresponds to the protons peaked at energy 124 MeV and dashed-dotted line corresponds to the protons peaked at energy 166 MeV.

FIGS. 6(a) and 6(b) show the spatial distribution of protons N=N(y) at the plane x-40 cm, z=0 cm for the magnetic field configuration shown in FIG. 1, using a primary collimator opening of 5×5 $cm^2$ defined at 100 cm SSD and the proton energy distributions $N_i=N_i(E)$, where index i denotes the energy levels of the polyenergetic proton beams. Comparing FIG. 5, 6(a) and 6(b) to FIGS. 3 and 4 the spatial separation of protons at larger openings is less effective leading to the higher order of spatial mixing and the larger spread in the energy distributions. The energy spread as used herein is defined as the difference between the maximum and the minimum energy in the distribution. FIG. 7 shows the energy spread as a function of a collimator opening for several proton energy levels; the energy spread increases with increasing aperture opening and is more profound for higher energy particles.

Figure 8:
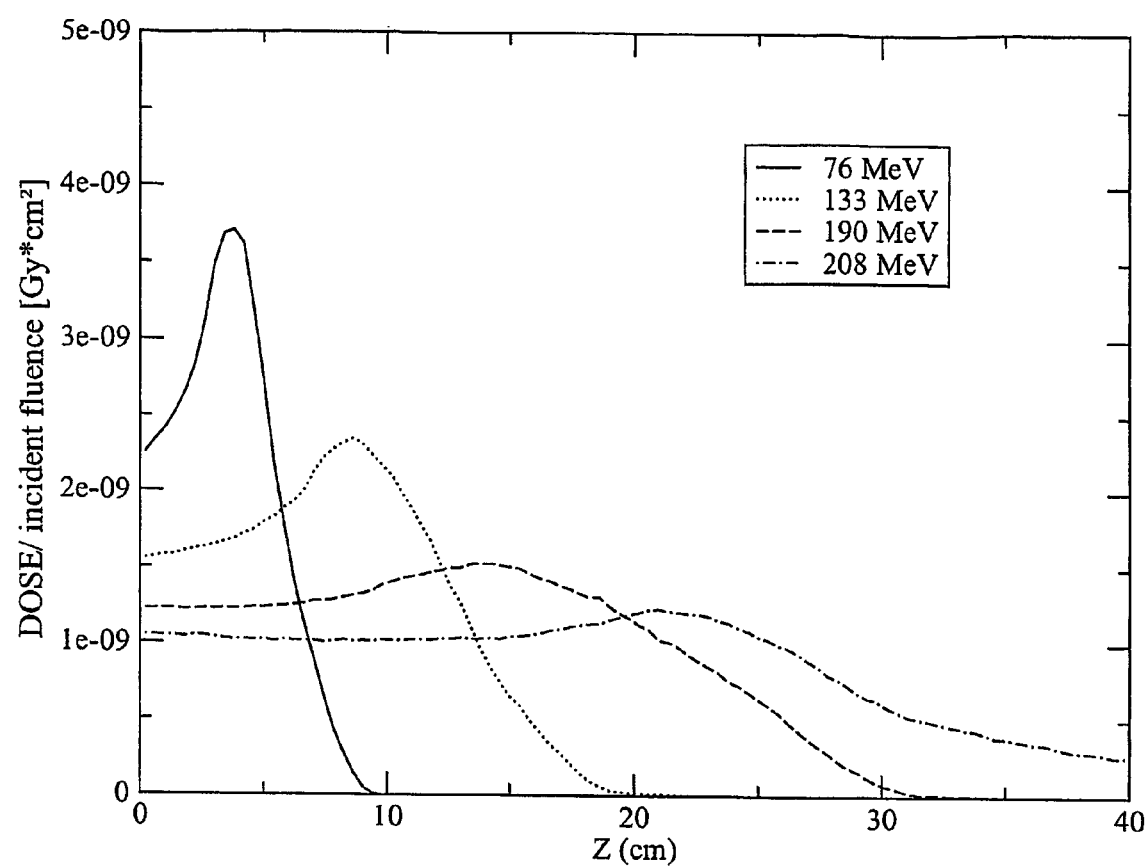
FIG. 8 shows the depth dose distributions for protons with energy spectra shown in FIG. 6(*b*) normalized to the initial proton fluence. The solid line represents the dose distribution calculated using the proton spectrum peaked at E=76 MeV, the dotted line represents the dose distribution calculated using the proton spectrum peaked at E=133 MeV, the dashed line represents the dose distribution calculated using the proton spectrum peaked at E=190 MeV, the dashed-dotted line represents the dose distribution calculated using the proton spectrum peaked at E=208 MeV. The primary collimator opening is 5×5 cm² defined at 100 cm SSD. One-standard deviation associated with the calculations is on the order of 1%.

As a result of the energy spread effect, the depth dose curves will typically have less sharp falloff beyond the effective Bragg peak region for wider apertures as compared to the cases of narrower collimator openings. FIG. 8 shows the dose distributions for the proton energy spectra shown in FIG. 6(b), which corresponds to a primary collimator of 5×5 $cm^2$ defined at 100 cm SSD, normalized to the incident proton fluence. Comparing FIG. 5 with FIG. 8 shows that desirable dosimetric characteristics from the laser accelerated protons are typically obtained for smaller primary collimator openings. Suitable primary collimator openings are typically smaller than about 2000 cm², more typically smaller than about 100 cm², and even more typically smaller than about 1 cm², when defined at 100 cm SSD. Typically there is a lower limit on the size of the collimator opening, which is suitably determined by the field size, dose rate, or both, that the system can yield after beam collimation. The geometry of the collimator opening typically influences the treatment time.

Once the depth dose distributions for polyenergetic proton beamlets are determined, a proton energy distribution that provides a homogeneous dose along the target's depth direction is calculated using the target location and volume. In one embodiment, the following steps are carried out to calculate the desired proton energy distribution:

1. The geometrical size of the target (in the depth direction) determines the proton energy range for radiating the target. Using the depth dose distributions for a given energy range, the weights for the individual polyenergetic beamlet are computed, with the assumption that the weight for the beamlet with the energy distribution, which gives the effective Bragg peak at the distal edge of the target, is set to one. The weights $W_i=W_i(E)$ are computed based on the requirement of the constancy of the dose along the depth direction of the target.

2. Once the weights are known, the proton energy distribution $N(E)$ for providing a suitable dose along the target's depth dimension are calculated by convolving the weights $W_i(E)$ with the energy distributions $N_i(E)$ of polyenergetic proton beamlets to give $$N(E) = \sum_i W_i(E) N_i(E) \quad (4)$$

where index i runs through energy levels of the polyenergetic proton beamlets for radiating the area of interest (in depth direction). A suitable energy modulation prescription for protons is provided by the formulation of the absorbed dose distribution for electrons introduced by Gustafsson, A., et al., in "*A generalized pencil beam algorithm for optimization of radiation therapy*", Med. Phys., 343–356 (1994), in which the incident particle differential energy fluence integrated over the surface and solid angle corresponds to the energy distribution defined in Eq. (4). As an example, a hypothetical target with spatial dimensions 4×4×5 cm³, located at depth lying between 9 cm and 14 cm is considered. The energy range of polyenergetic protons required to cover this target is 110 MeV<E<152 MeV. Using both the depth dose distributions for polyenergetic proton beamlets with the spread out energy spectra discussed earlier and the condition of a constancy of the resultant dose along the target's depth direction, the weights $W_i$ for each individual beamlet, that are indicated in Table 1 are readily obtained.

TABLE 1

| $W_{152}$ | 1.00 | $W_{149}$ | 0.25 | $W_{146}$ | 0.15 |
|---|---|---|---|---|---|
| $W_{143}$ | 0.12 | $W_{140}$ | 0.10 | $W_{137}$ | 0.095 |
| $W_{134}$ | 0.09 | $W_{131}$ | 0.085 | $W_{128}$ | 0.08 |
| $W_{125}$ | 0.07 | $W_{122}$ | 0.06 | $W_{119}$ | 0.05 |
| $W_{116}$ | 0.04 | $W_{113}$ | 0.035 | $W_{110}$ | 0.03 |

Distribution of weights corresponding to protons with a different characteristic energy: In one embodiment of the present invention, a procedure for finding the weights is provided. This procedure is mathematically similar to minimizing the following functional $$\Gamma(z) = \sum_i W_i D_i(z) - D_0, \text{ for } 9 \text{ cm} \leq z \leq 14 \text{ cm} \quad (5)$$

where i denotes energy bins, $D_i$ is the depth-dose distribution corresponding to the ith polyenergetic energy bin and $D_0$ is a constant corresponding to a specific dose level (typically larger than the distant Bragg peak in view of the contribution from the adjacent depth-dose distributions). The physical meaning of the weights are described further. The absolute value of each individual weight is correlated to the physical method associated with the actual energy modulation process in the selection system. The design of the energy modulation system (i.e., the aperture) is achieved by either using an aperture whose geometric shape is correlated to the weights or by using a slit, which can move along the y-axis in the region where the protons are spread according to their energy levels, and the time spent in a given region will be proportional to the value of the weight for the given energy. Convolving the weights of the Table (1) with the energy distributions for each individual beamlet according to equation (4), one obtains the actual modulated energy distribution that will deliver the SOBP for the given target's depth dimension. This energy distribution differs from that calculated using monoenergetic proton beams (for which the weights themselves represent the actual energy distribution) because of the presence of particles with energy levels beyond the ones associated with the weights, which typically arises from a consequence of a finite primary collimator. The presence of these "extra particles" typically makes the dose distribution beyond the SOBP fall off less sharply than that obtained using mono-energetic beams.

Figure 9A:
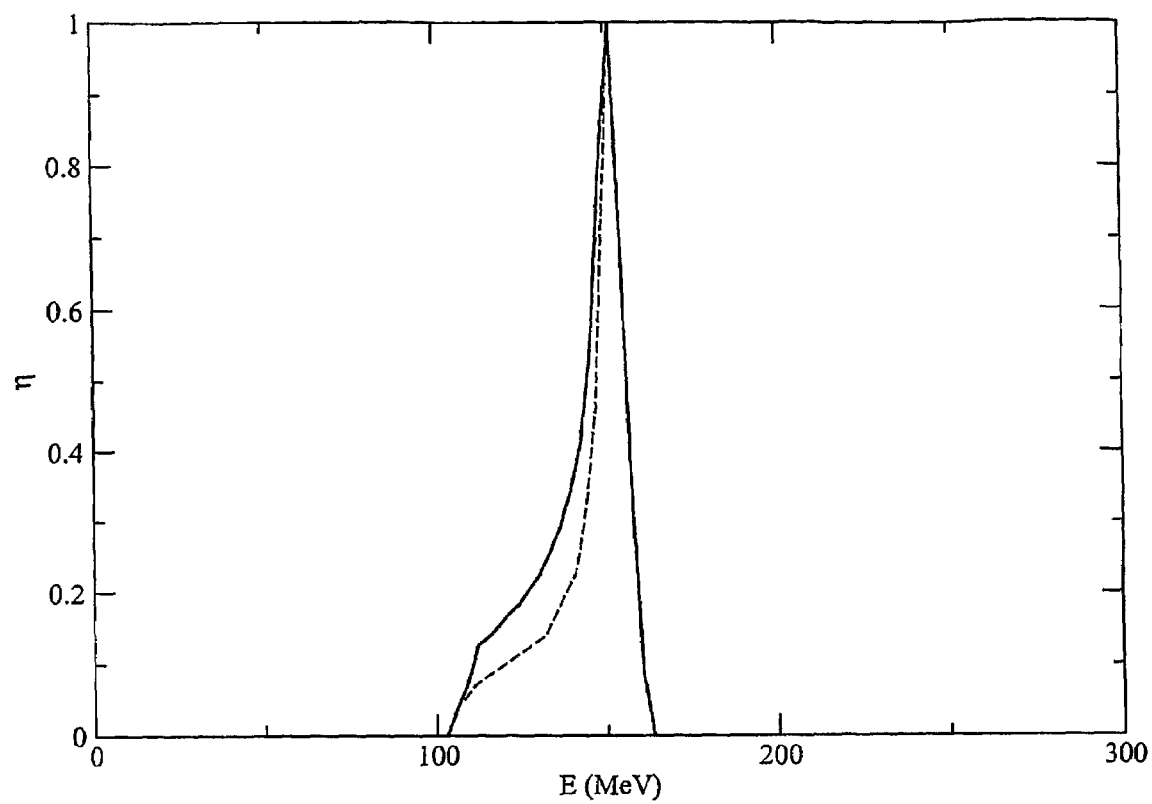
FIG. 9(*a*) shows the modulated proton energy distribution based on 1×1 cm² primary collimator opening defined at 100 cm SSD. η represents the number of protons in a given energy range normalized to the number of protons with energy E=152 MeV. The solid line represents the energy spectrum calculated using polyenergetic proton beams. The dashed line represents the energy spectrum calculated using mono-energetic protons.
Figure 9B:
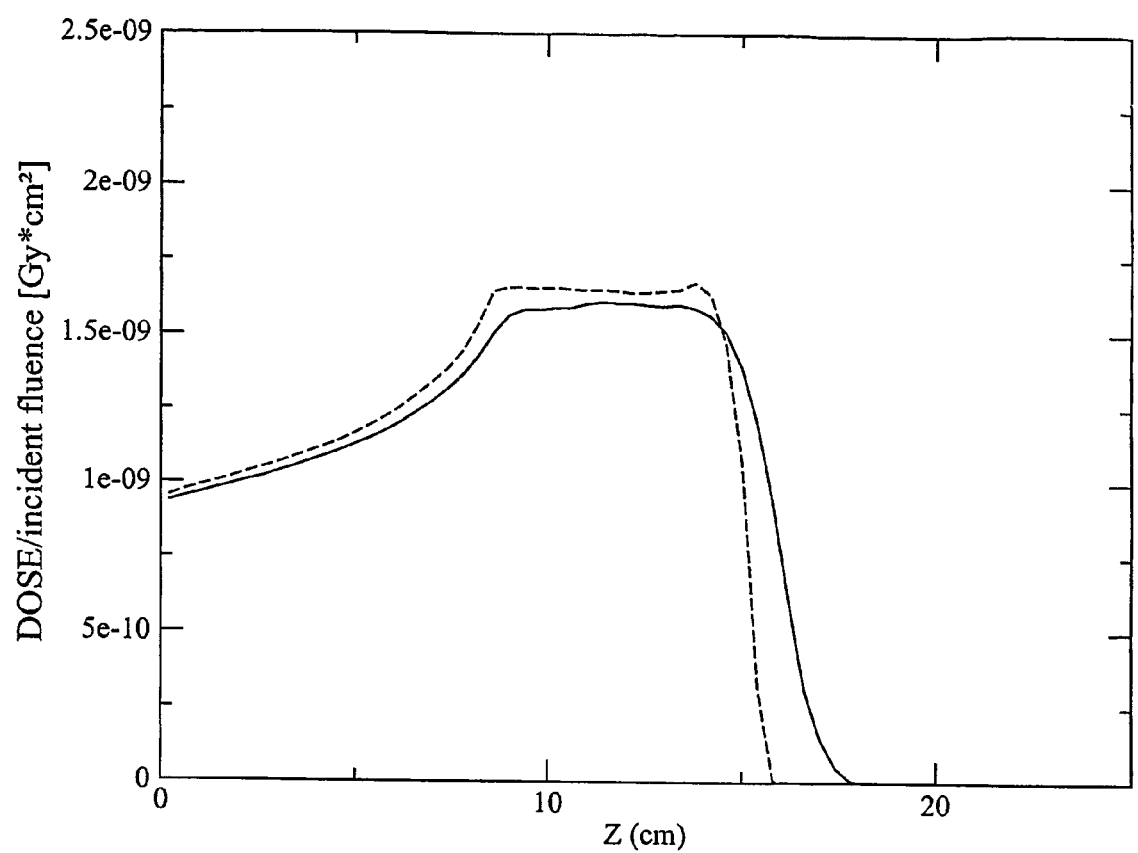

FIG. 9 shows the proton energy spectrum (a) and the corresponding dose distribution (normalized to the incident proton fluence) (b) for a target considered in the calculations. The resultant dose distribution shows the quick fall off of the dose beyond the distal edge of the target although not as dramatic as for an ideal case of convolving mono-energetic protons shown also in FIG. 9(b). The entrance dose is still significant compared to the dose to the target. In order to reduce the entrance dose, several proton beams coming from different directions but converging at the target could be used, so that the target receives the prescribed dose and the surrounding healthy tissue receives much less dose. Therefore, the energy and intensity modulated proton therapy is expected to further improve target coverage and normal tissue sparing.

Dose Rate Determination: As mentioned earlier, it is important to determine the absolute dose rate that the ion selection system can yield. This quantity is closely related to the absolute number of accelerated protons. From the PIC simulations it was determined that for a laser intensity of about I=1.9×10²² W/cm² and pulse length of about 14 fs, the number of protons accelerated to energy levels higher than about 9 MeV is about 4.4×10⁵ when the total number of protons used in PIC simulation is 1048576. Without being bound by a particular theory of operation, not all of the protons in the plasma slab are believed to interact with the laser. Only those protons that are located in the laser's propagation path typically experience the strongest interaction.

In simulation studies, the laser occupies an area of about ⅗ of the total size of the simulation box (in a direction perpendicular to the propagation), which provides about 6.3×10⁵ protons (out of 1048576) that will "sample" the laser. This means that about 70% of the effective number of protons are accelerated to energy levels higher than about 9 MeV. On the other hand, the total number of protons in a plasma slab that subtends the laser pulse can be estimated using the proton density of the foil nf as well as the laser focal area S and the thickness of the foil d to give $N = S \times n_f \times d \approx 2 \times 10^{12}$. Finally this gives about $N = 0.7 \times 2 \times 10^{12} = 1.4 \times 10^{12}$ protons that will be typically accelerated to energy levels greater than about 9 MeV.

With the above in mind, the absolute dose delivered to the target is estimated in the following way. The polyenergetic beams needed to cover the target in depth direction (9 cm $\leq z \leq$ 14 cm) will typically have an energy range of about 110–152 MeV. The number of protons in the energy range of about 147 MeV<E<157 MeV moving into the angle of 0.01 radian (approximately 2.6% of the total number of protons in the energy range 147 MeV<E<157 MeV) is $N = 2.6 \times 10^8$, which corresponds to $\Phi_0 = 2.6 \times 10^8$ l/cm$^2$ (1×1 cm$^2$ field size) per laser pulse for the initial fluence of protons at a distance of about 100 cm from the source.

FIG. 9(b) shows that the dose deposited by protons in the Monte Carlo simulations (normalized to the initial fluence) at depths 9 cm $\leq d \leq$ 14 cm is about $D_0 = 1.6 \times 10^{-9}$ Gy*cm$^2$. This gives $D = D_0 * \Phi_0 \approx 0.43$ Gy per laser shot. Typical lasers operating in a 10 Hz repetition rate yield D≈256 Gy per minute for the pencil beam of 1×1 cm$^2$. The dose rate is typically not only a function of laser-plasma parameters but also depends on the location and volume of the target. This leads to D≈64 Gy/min for the target located at depth z=25 cm (the distal edge of the target) with volume of 1×1×5 cM$^3$. While not being bound to any particular theory of operation, the reduction of the dose rate in this case is apparently due to both the smaller number of protons in the energy range needed to cover the deeply seated target, as well as the less energy deposited within the target (the height of the Bragg peak gets smaller as the proton energy increases). The calculation presented above estimates the absolute dose rate for 1×1 cm$^2$ pencil beam. More typically, the cross-section of the treatment volume is larger in area than 1×1 cm$^2$ and the "effective" dose rate becomes smaller and comparable to that of conventional linear accelerators. Larger targets can be effectively treated by scanning the high energy polyenergetic positive ion beam over the target. In an alternative embodiment, treatment target volumes larger than the cross section of the beam is irradiated by varying the field size to cover the cross sectional depth at the field volume using different proton energy levels in individual beams. Multiple beams varying in energy, area, location and shape can be combined to conform to the targeted volume. For example, for the hypothetical target considered in the energy-modulation calculations with spatial dimensions of 4×4×5 cM$^3$, the dose rate becomes D=256/16=16 Gy/min. The same estimations would give D=4 Gy/min for a target located at depth z-25 cm and a volume of 4×4×5 cm$^3$. The calculations presented above can also be used to estimate the treatment time needed for a given target. Assuming the 2 Gy treatment regiment, the time needed to deliver this dose to a target with a volume of 4×4×5 cm$^3$ located at depth of 14 cm is t=2/16=0.125 minute. This is carried out using a laser-accelerated high energy polyenergetic positive ion beam treatment center (200), such as the one described in FIG. 17.

Figure 17:
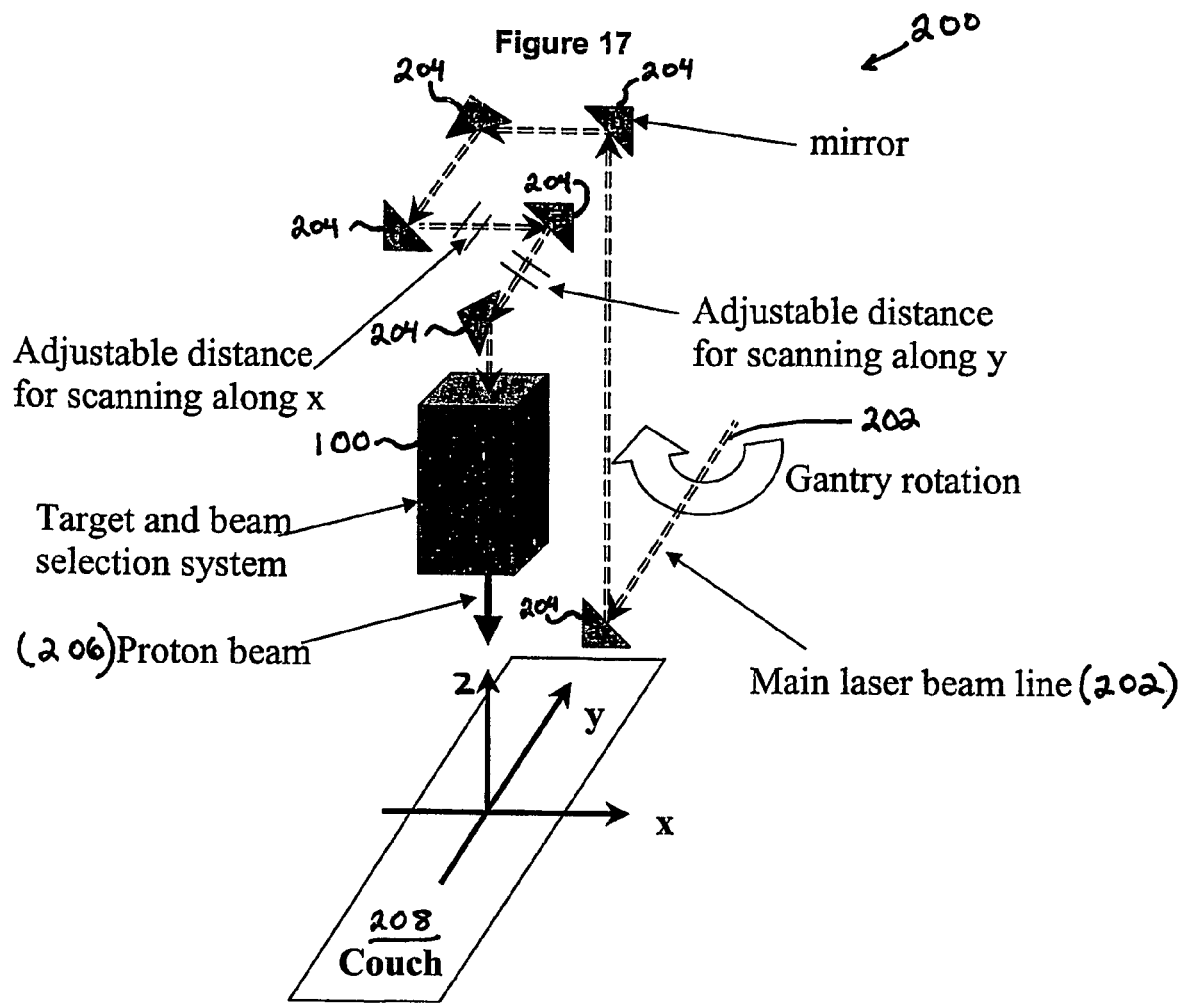
FIG. 17 shows a schematic diagram of one embodiment of a laser-accelerated positive ion beam treatment center (e.g., laser-proton therapy unit, the laser is not shown) having a laser beam line and beam scanning mechanism of the laser-driven proton therapy system of the invention.

Referring to the laser-accelerated high energy polyenergetic positive ion beam treatment center (200) in FIG. 17, there is provided a main laser beam line (202) that is reflectively transported using a series of beam reflectors, e.g., mirrors (204, a–f), to a target and ion selection system (100). The target and ion selection system (100) includes the target system for generating high energy polyenergetic ions and an ion separation system, such as depicted schematically in FIG. 1 (with target) and 18 (without target). The proton beam exiting the target and ion selection system includes therapeutically suitable high energy polyenergetic positive ions that are generated as described above. As shown, the proton beam exiting the target and ion selection system are directed in the direction parallel to the direction of the laser beam entering the target and ion selection system. The proton beam (206) is shown directed towards a couch (208), which locates the patient and the patient's target. The mirrors (204a–f) and target and ion selection system (100) are capable of being rotated (here shown capable of being rotated in the x-z plane, the z direction being perpendicular to the x-y plane) around the axis of the main laser beam line using a gantry. Typically, the final mirror (204, f) from which the laser beam is reflected into the target and ion selection system (100) is fixed to the target and ion selection system. The distance between the final mirror (204, f) and mirror (204, e) and ion selection system is shown adjustable along the y direction to permit scanning of the proton beam (206) along the y direction. The distance between mirror (e) and mirror (d) is shown adjustable along the x direction to permit scanning of the proton beam along the x direction. Suitable target and ion selection systems (100) are compact (i.e., less than about 100 to 200 kg in total mass, and less than about 1 meter in dimension). The compactness of the target and ion selection systems permit their positioning with robotically-controlled systems to provide rapid scanning of the proton beam (206) up to about 10 cm/s.

One embodiment of the high energy polyenergetic positive ion beam radiation treatment centers of the present invention includes the components as shown in FIG. 17, along with a suitable laser (such as described with respect to FIG. 12 below) and a system for monitoring and controlling the therapeutically suitable high energy polyenergetic positive ions. Suitable lasers are typically housed in a building, such as in the same building as the positive ion beam treatment center, or possibly in a nearby building connected by a conduit for containing the laser beam. The main laser beam line (202) is typically transported through the building within shielded vacuum conduit using a series of mirrors (e.g., 204) to direct the laser beam (202) to the target and ion selection system (100). The target and ion selection system (100) is typically mounted on a gantry, which is placed in a treatment room. In additional embodiments of the present invention, the main laser beam (202) is split using a beam splitter into a plurality of laser beams emanating from a single laser. Each of the laser beams emanating from the beam splitter is directed to an individual target and ion selection system (100) for treating a patient. In this fashion, high energy polyenergetic positive ion radiation treatment centers are provided using one laser source and a plurality of ion therapy systems to treat a plurality of patients. In certain embodiments of the high energy polyenergetic positive ion radiation treatment centers of the present invention, there are provided a plurality of treatment rooms, each treatment room having an individual target and ion selection system, a location for a patient, and a proton beam monitoring and controlling system. A plurality of treatment rooms equipped this way enables a greater number of patients that can be treated with the investment of one high power laser for providing therapeutically suitable high energy polyenergetic positive ions.

Laser-accelerated proton beams also typically generate neutrons, which may contaminate the ion beam. The energy modulation process leads to a large portion of proton energy being deposited within the beam stoppers as well as the aperture and collimators. As described earlier, $N=1.4\times10^{12}$ protons have energy levels higher than 9 MeV. In this regard, these protons can be accelerated by the laser, and only 0.02% of the total proton energy is allowed to go through the final collimator and be deposited within the target. Proper shielding is typically provided to prevent the "waste" protons and unselected particles and their descendants from leaking out of the treatment unit. There is a finite probability that some of the contaminant particles may pass through the final (or secondary) collimating device (138) or leak out through the shielding. Determining the number of contaminant particles is typically considered in the shielding calculations.

Coulomb Expansion of Proton beam: Without being bound by a particular theory of operation and referring to FIG. 1, it is believed that as the protons go through the aperture (118), the subsequent recombining magnetic field configuration (112), and through the secondary collimation device (138), the protons (134) form a non-neutral proton plasma with uncompensated charge, which typically tends to spread apart due to a repulsive force arising from the Coulomb interaction among the protons. This repulsive force typically introduces an extra divergence to the proton beam in addition to the initial divergence. The initial divergence is typically due to the angular spread of the laser-accelerated protons, which is typically controlled by the geometry of the primary collimation device. The magnitude of the repulsive force depends on the proton density at the exit region. Both the theoretical description as well as the particle in cell simulations can be used to estimate the rate at which the given distribution of protons will expand. For simplicity, a spherically symmetrical distribution of protons with a given initial density and size is assumed to correspond to the size and density of the proton cloud at the exit region. Due to the spherical symmetry of the problem considered, the subsequent time evolution of the system typically maintains its symmetry. The equation of motion for the outer most protons, which can approximate the size of a proton cloud, is, in the non-relativistic limit, $$m\frac{d^2r}{dt^2} = \frac{eQ}{4\pi\varepsilon_0}\frac{r}{r^3} \quad (6)$$

where m is the proton mass and Q is the charge of the proton cloud. It is convenient to introduce the dimensionless units $\tau=t\omega_{pi}$, $r=RR_0$, where $R_0$ is the initial radius of the proton cloud, $\omega_{pi}=\sqrt{ne^2/m_p\varepsilon_0}$ is the proton plasma frequency and n is the initial proton density. In these units, the equation governing the evolution of the outer part of the proton cloud is, $$\frac{d^2R}{d^2\tau} = \frac{R}{3R^3} \quad (7)$$

Figure 10:
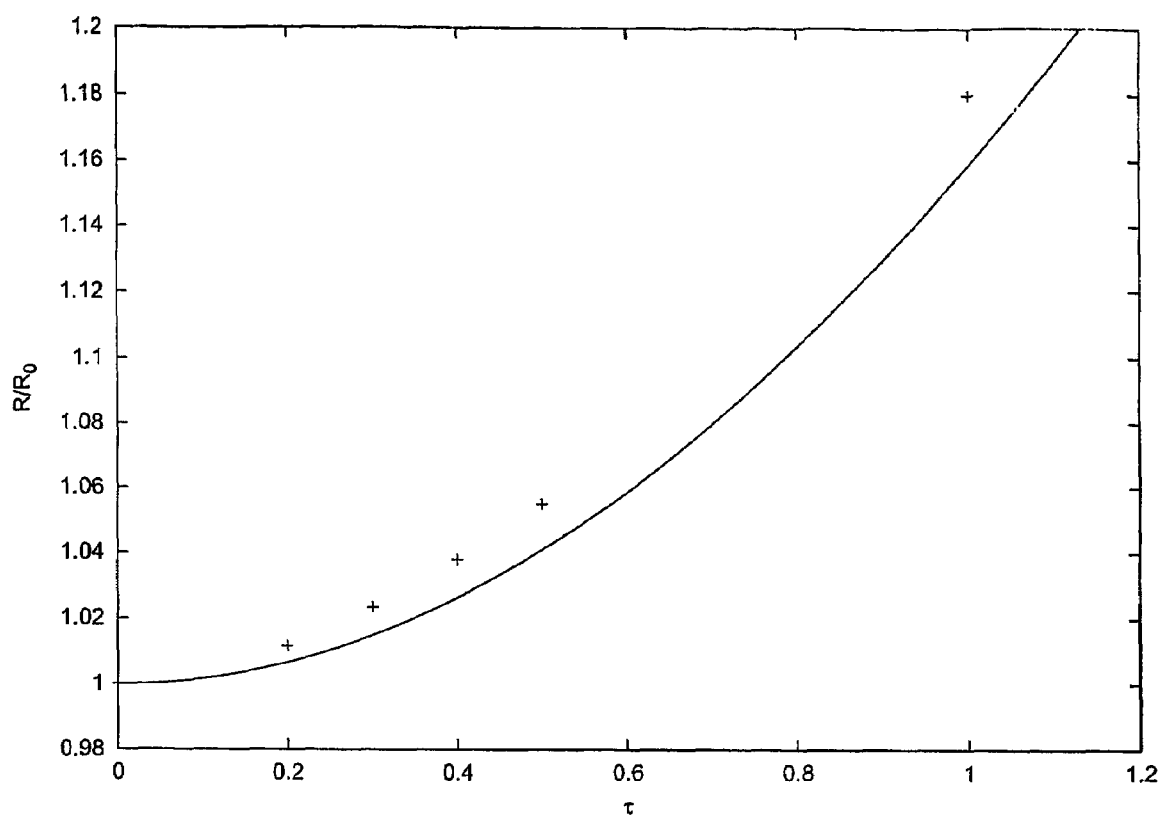
FIG. 10 shows the temporal evolution of the proton cloud's size. The solid line represents the numerical solution to Equation 7. The points represent the results of PIC simulations. τ represents time in units of ion plasma frequency, $\tau=\omega_{pi}t$.

The numerical solution to this equation with the initial conditions $R=1$, $dR/d\tau=0$ when $\tau=0$ is plotted in FIG. 10. To convert these results to the real space-time variables, the value for the proton plasma frequency $\omega_{pi}$ is used, which in turn typically requires the knowledge of the initial proton density in a cloud. The total number of protons in a cloud can be estimated using the arguments presented earlier. Through suitable calculations, the number of protons accelerated to energy levels higher than about 9 MeV is determined to be about $N\approx1.4*10^{12}$. A small fraction ($\approx0.03$) of these protons typically pass through the initial collimation device, giving $N\approx4*10^{10}$. In one embodiment of the present invention described in FIG. 1, where an exit point of the particle selection system is at 70 cm away from the source, the volume that the accelerated protons occupy is determined as the product $V=\Delta L_x\Delta L_y\Delta L_z$, where $\Delta L_x$, $\Delta L_y$ and $\Delta L_z$ are the spatial dimensions of the proton cloud. For a 0.7×0.7 cm² field size, $\Delta L_y$=0.7 cm, $\Delta L_z$=0.7 cm. $\Delta L_x$ can be found by calculating the spatial extent, at the exit point, between the fastest and the slowest particles used for the therapeutic purposes (typically about 50 MeV<E<about 500 MeV; and more typically about 80 MeV<E<about 250 MeV). For these energy levels, $\Delta L_x=L^*(1-v_s/v_f)\approx25$ cm. With that in mind, the average proton density and the proton plasma frequency are $n=N/V\approx3.5\times10^{10}$ cm$^{-3}$, $\omega_{pi}\approx6\times10^7$ s$^{-1}$. Providing a patient location 1 meter ("m") away from the secondary collimation device, the average time required for a proton beam to reach a patient is $t\approx7*10^{-9}$ s, giving $\tau=\omega_{pi}t=0.4$. FIG. 10 shows that at $\tau=0.4$, a two to three percent increase in the size of the proton cloud is expected to arise primarily from the electrostatic repulsion. FIG. 10 also shows the results of PIC simulations of the non-neutral proton plasma dynamics with the initial conditions corresponding to those used in this description. As shown here, there is a good agreement between the two approaches. The calculations shown above represent an upper limit for the rate of proton divergence due to the electrostatic repulsion. Typically, due to the energy modulation process, the total number of particles will be less than that used in the calculations (since many of the initial protons will be discarded), thus a lower beam divergence rate due to the electrostatic repulsion typically results.

In one embodiment of the present invention there is provided a proton selection system. The calculations provided herein show that ion selection systems of the present invention that utilize a magnetic field along with a collimation device can generate proton beams with energy spectra suitable for radiation treatment. Due to the broad energy and angular distributions of the laser-accelerated protons, the ion selection system provides polyenergetic positive ion (e.g., proton) beams with energy distributions that have an energy spread in them, leading to broader dose distributions as compared to the case of monoenergetic protons. A design of this embodiment provides for a collimator opening of about 1×1 cm² defined at about 100 cm SSD, the energy spread for about 80 MeV proton beam is about 9 MeV, and the energy spread for about 250 MeV proton beam is about 50 MeV. In this system, as the primary aperture opening increases, the spread in proton energy distributions increases as well. The calculated depth-dose distributions for collimator openings of about 1×1 cm², about 5×5 cm² and about 10×10 cm² show the preference of using narrower apertures. The aperture opening cannot be arbitrarily small, since it would decrease the effective dose rate for larger targets. A collimator opening of about 1×1 cm² defined at about 100 cm SSD typically provides an adequate treatment time as well as typically provides satisfactory depth-dose distributions for energy-modulated proton beams.

The proton selection systems provided by the various embodiments of the present invention open up a way for generating small beamlets of polyenergetic protons that can be used for inverse treatment planning. Due to the dosimetric characteristics of protons, the energy and intensity modulated proton therapy can significantly improve the conformity of the dose to the treatment volume. In addition, healthy tissues are spared using the methods of the present invention compared to conventional treatments. Overall results suggest that the laser accelerated protons together with the ion selection system for radiation treatments will bring significant advances in the management of cancer.

Figure 11:
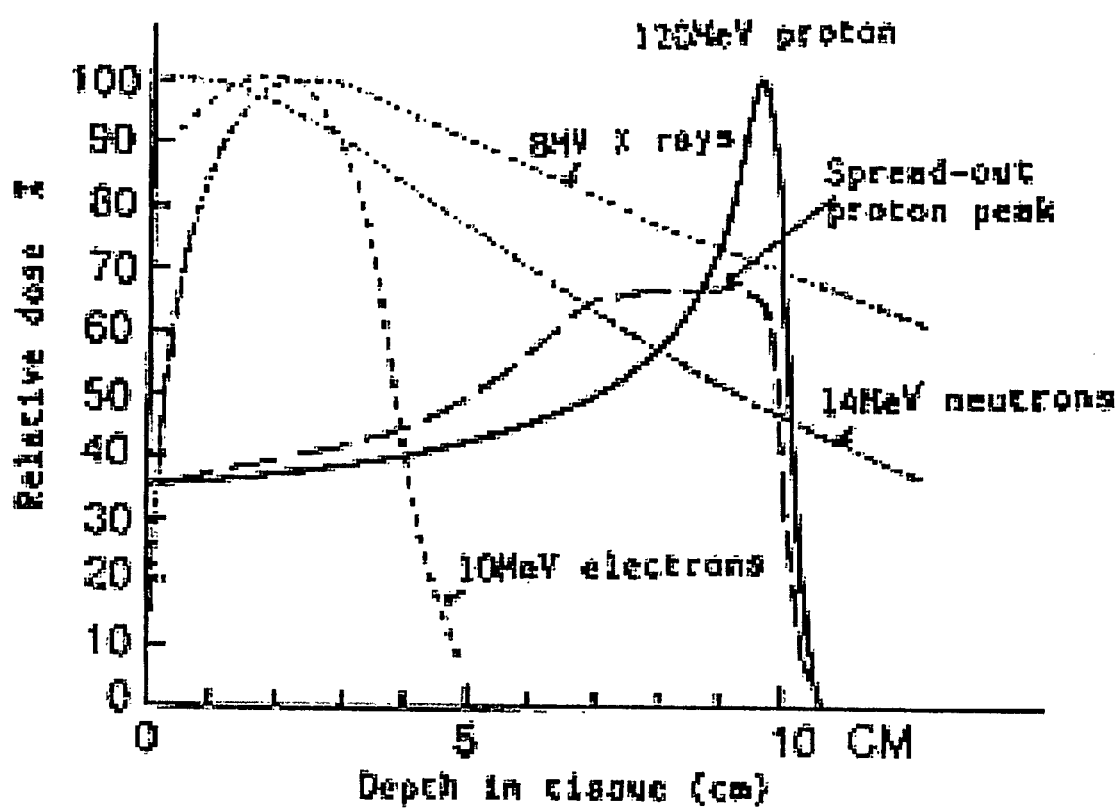
FIG. 11 shows dose distributions of various radiation modalities as a function of depth in water.

Radiation therapy is one of the most effective treatment modalities for prostate cancer. In external beam radiation therapy, the use of proton beams provides the possibility of superior dose conformity to the treatment target and normal tissue sparing as a result of the Bragg peak effect. FIG. 11 shows the energy deposition (or dose) as a function of the penetration depth for protons, photons (X-rays), electrons, and neutrons. While neutrons and photons (X-rays) show high entrance dose and slow attenuation with depth, monoenergetic protons have a very sharp peak of energy deposition as a function of the beam penetration just before propagation through tissue stops. As a consequence, it is possible for almost all of the incident proton energy to be deposited within or very near the 3D tumor volume, avoiding radiation-induced injury to surrounding normal tissues. Protons have a higher linear energy transfer component near the end of their range, and are expected to be more effective biologically for radiotherapy of deep-seated tumors than conventional medical accelerator beams or cobalt-60 sources.

In spite of the dosimetric superiority characterized by the sharp Bragg peak, utilization of proton therapy has lagged far behind that of photons for prostate treatment. This is because the operating regime for proton accelerators is at least an order of magnitude higher in cost and complexity, which results in their being too expensive for widespread clinical use compared to electron/photon medical accelerators. Conventional proton accelerators are cyclotrons and synchrotrons, of which only two such medical facilities exist in the U.S., those of Massachusetts General Hospital (MGH) (Jongen 1996, Flanz et al. 1998) and Loma Linda University Medical Center (LLUMC) (Cole 1991). Both occupy a very large space (entire floor or building). Although they are growing in number, only several such clinical facilities exist in the world (Sisterson 1999). Despite a somewhat limited number of clinical cases from these facilities, treatment records have shown encouraging results particularly for well-localized radio resistant lesions (Sisterson 1989, 1996; Austin-Seymour et al., Duggan and Morgan 1997; Seddon et al. 1990; Kjellberg 1986). The degree of clinical effectiveness for a wide variety of malignancies has not been quantified due to limited treatment experience with this beam modality. This situation will be greatly improved by the availability of a compact, flexible, and cost-effective proton therapy system, as provided by the present invention. The present invention enables the widespread use of this superior beam modality and therefore bring significant advances in the management of cancers, such as brain, lung, breast and prostate cancers.

In one embodiment of the present invention there is provided a compact, flexible and cost-effective proton therapy system. This embodiment relies on three technological breakthroughs: (1) laser-acceleration of high-energy polyenergetic protons, (2) compact system design for ion selection and beam collimation, and (3) treatment optimization software to utilize laser-accelerated proton beams. As described above, laser-proton sources have been developed to accelerate protons using laser-induced plasmas. U.S. patent application Ser. No. 09/757,150 filed Jan. 8, 2001, Pub. No. U.S. 2002/0090194 A1, Pub. Date Jul. 11, 2002, "Laser Driven Ion Accelerator", discloses a system and method of accelerating ions in an accelerator using such a laser light source system, the details of which are incorporated by reference herein in their entirety. Such laser-proton sources are compact for the reason that the accelerating gradient induced by the laser is far greater, and the beam emittance is far smaller, than current radio-frequency and magnet technology based cyclotrons and synchrotrons (Umstadter et al. 1996).

One embodiment of the present invention provides an ion-selection system in which a magnetic field is used to spread the laser-accelerated protons spatially based on their energy levels and emitting angles, and apertures of different shapes are used to select protons within a therapeutic window of energy and angle. Such a compact device eliminates the need for the massive beam transportation and collimating equipment that is common in conventional proton therapy systems. The laser-proton source and the ion selection and collimating device of the present invention are typically installed on a treatment gantry (such as provided by a conventional clinical accelerator) to form a compact treatment unit, which can be installed in a conventional radiotherapy treatment room.

A treatment optimization algorithm is also provided to utilize the small pencil beams of protons generated with ion selection systems of the present invention to obtain conformal dose distributions for cancer therapy, such as for prostate treatment. In various embodiments of the present invention there are provided optimal target configurations for laser-proton acceleration and methods for ion selection and beam collimation. In this embodiment of the present invention, dose distributions of laser-accelerated protons for cancer treatment are typically determined by dose calculation of proton beamlets, optimization of beamlet weights and delivery of beamlets using efficient scan sequence. Commercial software is available for carrying out intensity modulation of photon beams for targeting. Such software can be adapted for use with laser-accelerated proton beams by the following steps: calculating dose needed; optimizing the weights of the beam; and determining the sequence of the therapeutically suitable high energy polyenergetic positive ion beams. As a specific example, the treatment of prostate cancer is carried out by selecting beam incident angles based on the target volume and its relationship with the critical structures (rectum, bladder and femurs), preparing positive ion beams with different shapes, sizes and/or energies, optimizing the weights of individual beamlets, generating a scan sequence based on the beam weights, and verifying the final dose distribution by Monte Carlo calculations or by measuring with a suitable monitoring device.

Laser acceleration was first suggested in 1979 for electrons (Tajima and Dawson 1979) and rapid progress in laser-electron acceleration began in the 1990's after chirped pulse amplification (CPA) was invented (Strickland et al. 1985) and convenient high fluence solid-state laser materials such as Ti:sapphire were discovered and developed. The first experiment that has observed protons generated with energy levels much beyond several MeV is based on the Petawatt Laser at the Lawrence Livermore National Laboratory (LLNL) (Key et al. 1999, Snavely et al. 2000). Until then there had been several experiments that observed protons of energy levels up to 1 or 2 MeV, which were considered to be 'standard' (Maximchuck et al. 2000). Another experiment at the Rutherford-Appleton Laboratory in the U.K. has been reported recently with proton energy levels of up to 30 MeV (Clark et al. 2000). The Petawatt Laser is a specially modified arm of large NOVA Laser at LLNL. The pulse is shortened by the CPA technique (Strickland et al. 1985) into several hundred fs (femtosecond, fs=$10^{-15}$ sec), but it is not ultrashort (i.e. in the range of tens of fs). In the latest Petawatt Laser experiments, high-energy protons of 58 MeV were observed (Key et al. 1999, Snavely et al. 2000). A surprisingly large fraction of laser energy (of the order of 10%) was converted into proton energy in these experiments. Without being bound by a particular theory of operation, the electrostatic field generated by electrons driven by the laser is generally considered to be the main initiator (Wilks et al. 1999). Hydrogen atoms and thus protons, which are quickly generated from ionization of hydrogen, are typically accelerated from the back surface of the metal due to the electronic space charge to high energy levels. There are several relevant theoretical and computational studies of proton acceleration at high laser intensities (Rau et al. 1998; Bulanov et al. 1999; Wilks et al. 1999; Ueshima et al. 1999, Fourkal et al. 2002a).

Figure 12:
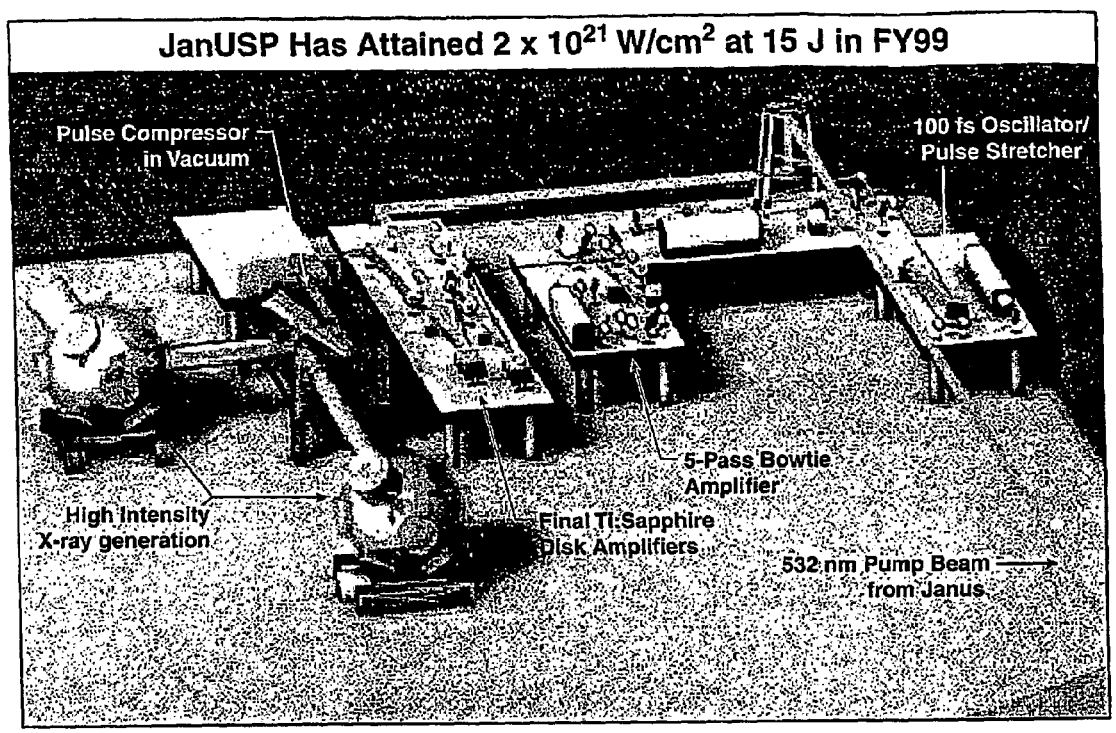
FIG. 12 shows the JanUSP laser system and target chambers.
Figure 16A:
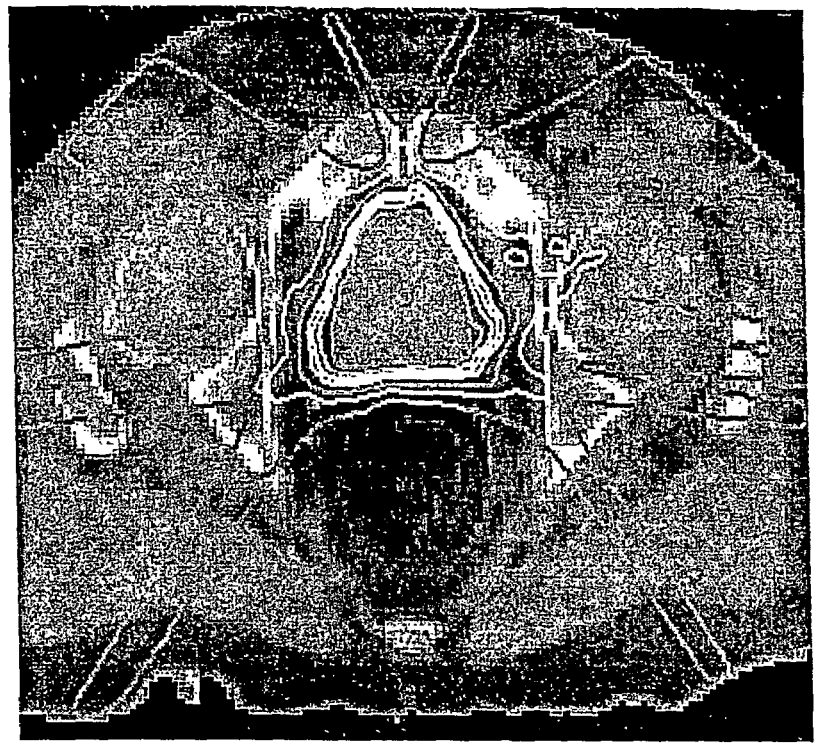
FIG. 16 shows isodose distributions for a 8-field EIMPT plan (a) and a 8-field photon IMRT plan (b), and DVHs for the target (c) and the rectum (d) for the same patient geometry using 4 different treatment modalities. The pre-scribed target (PTV) dose is 50 Gy. The isodose lines represent 5, 15, 25, 35, 40, 45, 50 and 55 Gy.
Figure 16B:
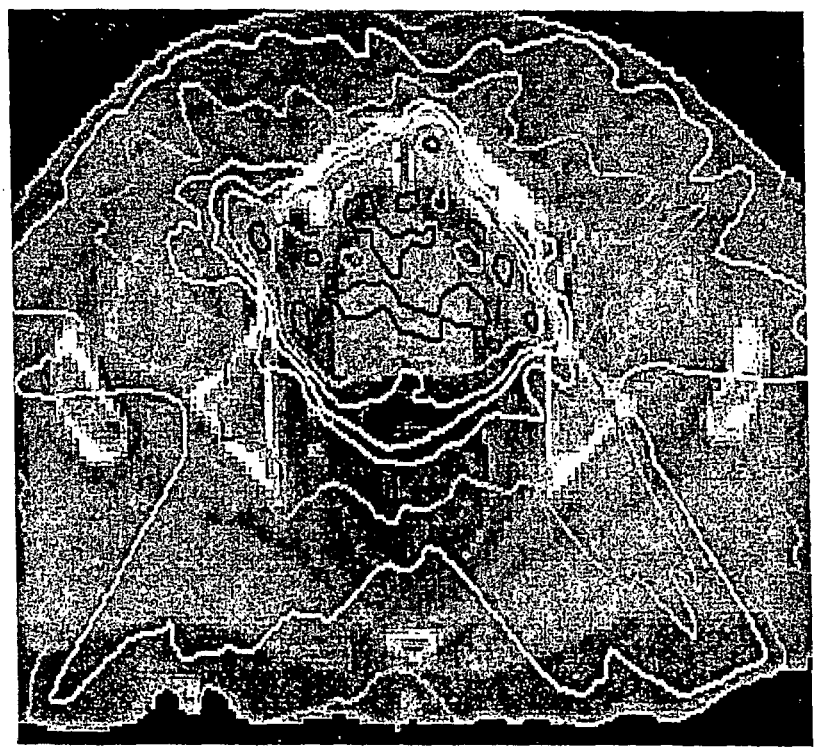
Figure 16C:
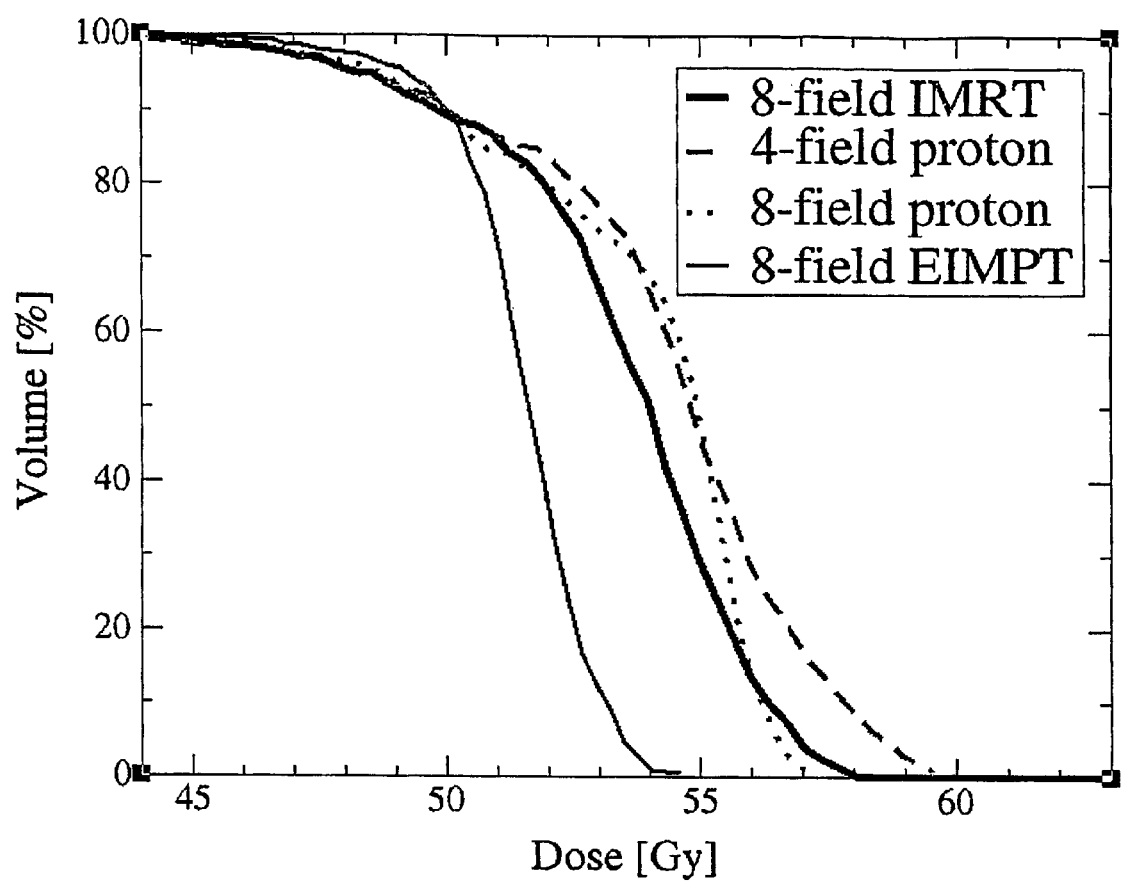
Figure 16D:
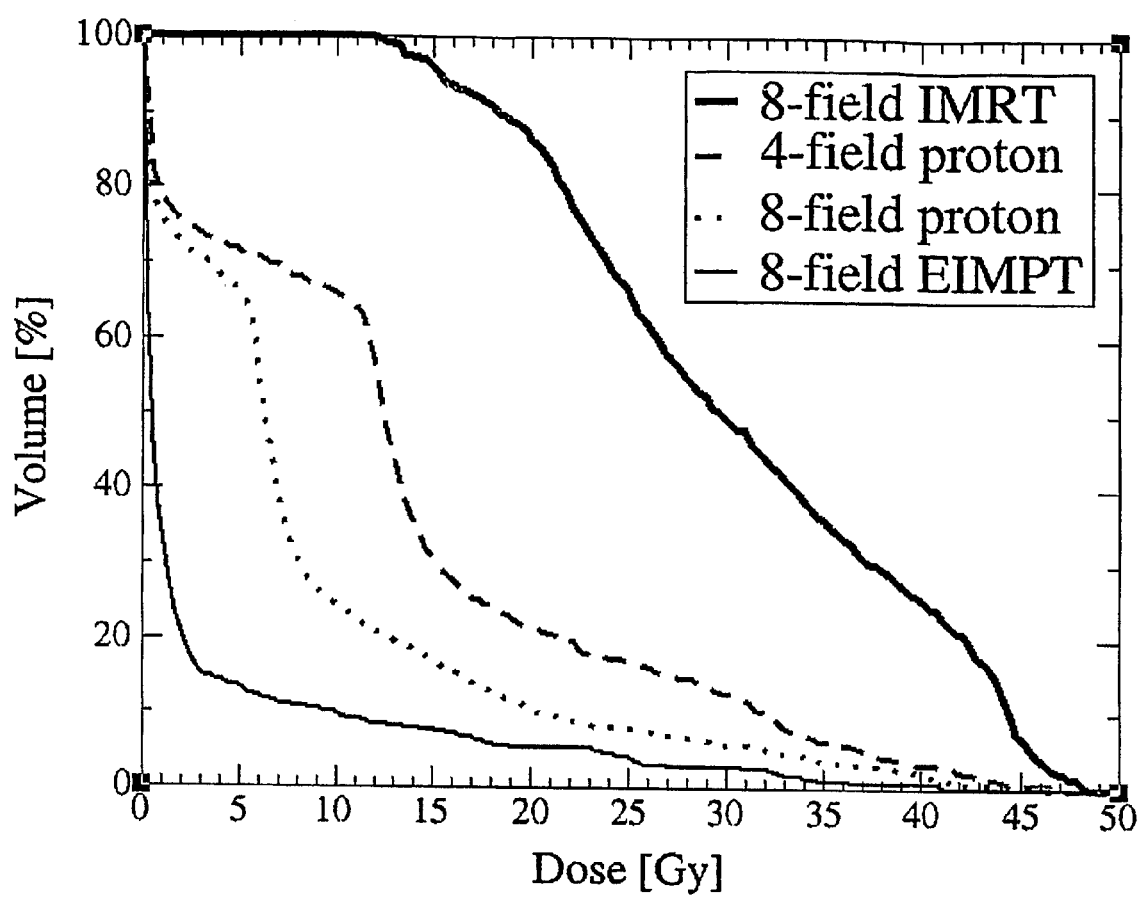

Experimental investigations on laser-proton acceleration using a short pulsed CPA intense Ti:sapphire laser (JanUSP) have been carried out. This technology is different from that of the Petawatt Laser (based on a glass laser). The short-pulsed Ti:sapphire laser can be much more compact and have higher repetition than the glass laser. This is particularly useful for radiotherapy applications as multiple shorts are typically needed for one treatment. The JanUSP laser system is shown in FIG. 12. A continuous train of 800 nm sub-100 fs pulses is emitted from a commercial mode locked oscillator pumped by 8 Watts of 530 nm light. The time-frequency transform limited oscillator output is stretched in a folded diffraction grating pulse stretcher to approximately 250 ps. The stretched 4 nJ pulse is then amplified in a regenerative amplifier to 8 mJ and then to 220 mJ in a 5 pass amplifier in a bow-tie configuration. Isolation from amplified spontaneous emission and pre-pulse leakage from the regenerative amplifier is provided by three stages of glan polarizer Pockel cell pulse slicers. The portion of the laser operates at 10 Hz and 90 mJ energy, allowing both rapid setup and timing of diagnostics at intensities up to $10^{19}$ W/cm$^2$. Two additional stages of amplification are pumped by a frequency doubled Nd:Silicate glass amplifier. These final amplifiers raise the stretched beam energy to greater than 21 J. A vacuum compressor employing two 40 cm diameter gratings is used for pulse recompression to 80 fs. The 200 TW compressed pulse is routed in vacuum to the target chamber, where it is focused onto the target by a 15 cm diameter F/2 off-axis parabola to provide focal intensities on target of >2×10$^{21}$ W/cm$^2$. The Gaussian focal spot is approximately 2 μm in diameter. Because of its high focal intensity, the JanUSP laser is a suitable laser that is coupled to a targeting system for generating high energy polyenergetic ion beams in accordance with the invention.

A facility for a laser-accelerated ion therapy system can be designed using previous neutron treatment suites in existing cancer treatment facilities, which provide adequate space and shielding. A typical laser useful in the ion therapy system has a similar construction as the JanUSP laser. The laser pulse repetition rate is typically designed at a rate of from 1–100 Hz, but typically is about 2 to 50 Hz, and most typically about 10 Hz. Laser intensity is typically in the range of from about 10$^{17}$ W/cm$^2$ to about 10$^{24}$ W/cm$^2$, more typically in the range of from about 10$^{19}$ W/cm$^2$ to about 10$^{23}$ W/cm$^2$, and even more typically in the range of from about 10$^{20}$ W/cm$^2$ to about 10$^{22}$ W/cm$^2$, and most typically about 10$^{21}$ W/cm$^2$, which is commercially available.

It has been found that the target configuration plays an important role in laser-proton acceleration. At an intensity of 10$^{21}$ W/cm$^2$, recent theoretical and computational results (Tajima 1999; Ueshima et al. 1999) show that under favorable conditions protons can be accelerated up to about 400 MeV (Table 2). It was found (Tajima 1999) that the innovation of the target and judicious choice of laser and target parameters can yield a large number of protons with energy levels>100 MeV. Depending on the details of the target preparation and geometry, as well as the pulse length and shape, the average and maximum energy levels of protons (and other ions) vary. In Case 3, with the most sophisticated target, the average proton energy is in excess of 100 MeV and the maximum is 400 MeV. The energy converted into ions amounts to 14% of the incoming laser energy. This efficiency is consistent with the Petawatt Laser, where about 10% conversion efficiency into protons was observed although parameters and preparations differed from Case 3.

TABLE 2

Particle-in-cell (PIC) Results (Ueshima et al. 1999) on proton and electron acceleration by laser irradiation on three thin targets. A laser intensity of 10$^{21}$ W/cm$^2$ on the target surface is applied.

| | Case 1 | Case 2 | Case 3 |
|---|---|---|---|
| Energy conversion | 50% | 24% | 31% |
| Ion | 4% | 8% | 14% |
| Electron | 48% | 16% | 17% |
| Peak energy H$^+$ | 200 MeV | 400 MeV | 400 MeV |
| Peak energy Al$^{10+}$ | 1 GeV | 2 GeV | 2 GeV |
| Peak energy electron | 25 MeV | 15 MeV | 20 MeV |
| Average energy H$^+$ | 58 MeV | 95 MeV | 115 MeV |
| Average energy Al$^{10+}$ | 130 MeV | 500 MeV | 500 MeV |

Without being bound to a particular theory of operation, a high laser intensity in the range of from about 10$^{17}$ W/cm$^2$ to about 10$^{24}$ W/cm$^2$ is believed to be an important parameter in the generation and acceleration of positive ions to energy levels suitable for radiation therapy. An other important parameter is the design of suitable targets that generate polyenergetic protons. Various suitable targets for generating high energy polyenergetic positive ions are known. Suitable targets have been designed using various materials, dimensions, and geometry. Laser irradiation fashion, e.g., intensity and spot size, is also known to influence the generation of positive ions. According to preliminary PIC simulations of the optimized laser target interaction (Ueshima et al. 1999; Tajima 1999, Fourkal et al. 2002a), the charge separation distance of a few microns with the electrostatic field on the order of 100 GeV/mm is expected to develop upon the irradiation of high Z materials (electron density of about 10$^{24}$/cm$^3$). With this field over this distance, protons can be accelerated to energy levels greater than 100 MeV. With proper geometry and dimensions of the target, the average proton energy levels may be increased by several times over a simple target. U.S. patent application Ser. No. 09/757,150 filed Jan. 8, 2001, Pub. No. U.S. 2002/0090194 A1, Pub. Date Jul. 11, 2002, "Laser Driven Ion Accelerator", is incorporated by reference herein for the disclosures pertaining to target construction used in a laser-proton accelerator systems. Such targets are suitably used in various embodiments of the present invention.

In Table 2, Case 3, with a particular target shape, an average proton energy greater than 100 MeV and the maximum energy at 400 MeV are provided. Various target configurations are readily tested for higher energy proton generation.

Based on these laser specifications, particle-in-cell (PIC) simulations have also been performed to investigate the effect of target shape, material and laser pulse length on the energy of laser-accelerated protons (Fourkal et al. 2002a). These results show that using a laser intensity of 10$^{21}$ W/cm$^2$ and a pulse length of 50 fs, protons can be accelerated to 310 MeV. FIG. 13 shows the angular distributions of these protons and the maximum proton energy as a function of the laser pulse length for the same laser intensity. The raw proton beams from a laser-driven proton accelerator have a broad energy spectrum and variable beam profiles for different energy levels; they typically cannot be used directly for therapeutic applications. One solution to this problem is to design a compact ion selection and collimation device in order to deliver small pencil beams (beamlets) of protons with desired energy spectra to cover the treatment depth range, as described earlier above and further below.

As shown in FIG. 14, 1 cm×1 cm beamlet depth dose curves are provided for different polyenergetic protons, described above. By combining the depth dose curves of different spectra, a spread out Bragg peak (SOBP) is achieved that covers the treatment target in the depth direction (FIG. 15). This process is termed herein, "energy modulation". Although the spectrum-based (polyenergetic) SOBP is not as clean as the monoenergetic SOBP, the weights of individual proton beamlets can be varied through an optimization routine to conform the dose distribution to the target laterally. As used herein, this process is termed "intensity modulation", which is commonly used for photon beam treatments. The estimated dose rate for the laser proton beams shown in FIGS. 14 and 15 is 1–20 Gy per minute for field sizes from 1 cm×1 cm to 20 cm×20 cm. Intensity-modulated radiation therapy (IMRT) using photon beams typically can deliver more conformal dose distributions to the prostate target (and the associated nodes) compared to conventional 4–6 photon field treatments. Modulation of the dose distribution of photon beams in the depth direction is essentially impossible, however, this is not the case with proton beams (Verhey and Munzenrider 1982). Accordingly, energy- and intensity-modulated proton therapy (EIMPT) further improves target coverage and normal tissue sparing for radiation treatments, such as for the treatment of prostate cancer. The combination of a compact ion selection and collimation device and an associated treatment optimization algorithm typically makes EIMPT possible using laser-accelerated proton beams. Without being bound to a particular theory of operation, the polyenergetic nature of a laser proton beam makes it ideal for EIMPT since it is convenient for both energy modulation (using a spectrum) and intensity modulation (through beam scanning).

To demonstrate the superiority of EIMPT for prostate treatment, dose distributions of prostate plans using different treatment modalities were compared (Ma et al. 2001a, Shahine et al. 2001). FIG. 16 shows dose volume histograms (DVH) of the target and the rectum for a prostate treatment. The proton isodose distribution is also shown. The photon IMRT plan was derived from a commercial treatment optimization system, CORVUS (NOMOS Corp., Sewickley, Pa.) using eight 15 MeV photon beams. The gantry angles were 45, 85, 115, 145, 215, 245, 275, and 315 degrees. The 8-field conventional proton plan included energy modulation but did not have intensity modulation. The proton beams were incident at the same gantry angles as the photon IMRT plan. The 8-field EIMPT included both energy modulation and intensity modulation with the same gantry angles. The 4-field conventional proton plan was derived using only 45, 115, 245, and 315 degrees ports. This shows that target coverage can be significantly improved using both energy- and intensity-modulation in a proton treatment. The rectum dose is much lower with the 8 field EIMPT compared to other beam modalities. The 8-field conventional proton plan is better than the 4-field proton plan and the latter is better than the 8-field photon IMRT plan in terms of the rectum dose. The results of Ma et al. 2001a are consistent with the findings of Cella et al. (2001), who compared 5-field intensity-modulated proton beams with 5-field IMRT (the Memorial Sloan-Kettering Cancer Center technique, Burman et al. 1997), 2-field conventional protons (the LLUMC technique, Slater et al. 1998), and the conventional 6-field photon treatment for prostate. EIMPT plans are consistently superior to conventional treatments and IMRT plans in target coverage and normal tissue sparing (lower doses to rectum, bladder and femoral heads).

The results of Ma et al. 2001a described above assumed ideal energy selection and beam collimation for the proton beamlets. The actual beamlet dose distributions of realistic proton spectra generated by the ion radiation system of the present invention will typically not be the same as the ideal dose distributions used in the preliminary calculations of Ma et al. 2001 a, which also used a 2D patient geometry to generate these plans.

The present inventor has demonstrated that different beamlet dose distributions can be combined through beamlet optimization to obtain ideal dose distributions. In one embodiment of the present invention, PIC simulations are performed to derive optimal target configurations and laser parameters and then use the simulated proton beam data to design an efficient ion selection and beam collimation device. The simulated proton phase space data is used for the Monte Carlo simulations to obtain accurate dose distributions using the proton beamlets from the proton therapy unit to achieve optimal target coverage and normal tissue sparing.

Through energy- and intensity-modulation, high-energy protons generated by a laser-accelerated proton source are developed into an effective modality for radiation therapy. The positive ion therapy systems of the present invention are comparable to conventional photon clinical accelerators both in size and in cost. Therefore, the widespread use of this compact, flexible and low-cost proton source will result in significant benefits for cancer patients.

Methods

System Design: As described above, the raw proton beams accelerated by laser induced plasmas typically cannot be used directly for radiotherapy treatment. An important component of a laser proton radiotherapy system is a compact ion selection and beam collimation device, which is coupled to a compact laser-proton source to deliver small pencil beams of protons of different energy levels and intensities. In one embodiment of the present invention there is provided an overall design of a laser-proton therapy system, which includes system structure and layout, mechanisms of the major components and research strategies for the experiment work (Ma 2000). FIG. 17 shows a schematic diagram of one embodiment of a laser-accelerated positive ion beam treatment center (e.g., laser-proton therapy unit, the laser not shown). The laser and the treatment unit are typically placed on the same suspension bench to ensure laser beam alignment (negligible energy loss due to the small distance). This also keeps the whole system compact. The target assembly and the ion selection device are placed on a rotating gantry and the laser beam is transported to the final focusing mirror 204(*f*) through a series of mirrors 204(*a*–*e*). The distances between mirrors 204(*d*) and 204(*e*) and mirrors 204(*e*) and 204(*f*) are adjusted to scan the proton beam along x- and y-axis, respectively, which generates a parallel scanned beam. An alternative method is to swing the target and ion selection device about the laser beam axis defined by mirrors 204(*d*) and 204(*e*) and that defined by

204(*e*) and 204(*f*), respectively, to achieve a scan pattern. This generates a divergent scan beam. The treatment couch is adjusted to perform coplanar and noncoplanar, isocentric and SSD (source-to-surface distance) treatments.

PIC study of proton acceleration: PIC simulations of target configurations and laser parameters are carried out for optimizing laser proton acceleration. The PIC simulation method computes the motions of a collection of charged particles (e.g., ions) interacting with each other and with externally applied fields. Charged plasma species are modeled as individual macroparticles (each macroparticle represents a large number of real particles). Since the spatial resolution is limited by the size of the particle, the spatial grid (cell) is introduced across the simulation box. The size of the grid is approximately equal to the size of the macroparticle. The charge densities as well as the electric currents are calculated at each grid position by assigning particles to the grid according to their position employing a weighting scheme. Once the charge density and the current density at the grid positions are known, the electric and magnetic fields at the same grid points are calculated using Poisson's and Maxwell's equations. These equations are typically solved using Fast Fourier Transforms (FFT). Fields at the particle positions are subsequently determined using an inverse weighting scheme in which the fields at the grid points are interpolated to the points of particle locations to yield the fields at particle locations. Particles are then moved via Newton's equations, using a leap-frog finite differencing method (positions and fields are calculated at integer time-steps, velocities at half time-steps). This procedure is repeated to give the time evolution of the system. A two-dimensional, electromagnetic relativistic PIC code is typically used for carrying out these optimization experiments. At each time step, the coordinates and momenta of the particles and electromagnetic field are calculated for the given initial and boundary conditions. All the variables to be calculated are functions of time and two spatial coordinates x and y. Different laser parameters and target geometry are simulated. Further details of our PIC simulations are described further herein and in Fourkal et al., 2002a.

PIC simulations are performed using the codes developed by Tajima (1989). These one to two-and-one-half dimensional, first-principle, full dynamics physics tools are particularly effective for ultrafast intense laser matter interaction. Those skilled in the art are experienced with high field science analyses (for example, Tajima et al. 2000) and with PIC simulations in plasma physics (Fourkal et al. 2002a). These skills can be applied to simulate previous experiments and the experimental setups currently used to confirm the experimental laser-proton acceleration results. The experimental situations are analyzed and the configurations and parameters are optimized to guide further experiments. Suitable targets used are typically simple freestanding planar foils and composite planar foils of plastic and other materials. Dense gas targets are also suitable targets. PIC simulations of these target configurations using different laser intensities, focal spot sizes and pulse lengths can be performed of the ion radiation facility of the present invention. An optimal set of laser parameters is found using these simulations that can produce protons of energy levels up to at least 250 MeV with small angular distribution and high dose rate. These PIC simulation results are used for further analytical studies on the ion selection and beam collimation system.

Characterization of laser-accelerated proton beams: Accurate determination of the characteristics of all the particle components in a laser-accelerated proton beam is particularly important. This knowledge assists the design and operation of the ion selection and beam collimation system. The energy, angular and spatial distributions of laser-accelerated protons are evaluated from the PIC simulations. Beam characterization studies are carried out for source modeling and beam commissioning for further dosimetric studies. Several Monte Carlo codes have been installed, expanded and extensively used for radiation therapy dose calculation including EGS4 (Nelson et al. 1985), PENELOPE (Salvat et al. 1996), PTRAN (Berger 1993), and GEANT (Goosens et al. 1993). The codes typically run on a PC network consisting of 16 Pentium III (866 MHz) microprocessors. Magnetic field distributions are simulated using commercial software, which is suitable for 3-dimensional field simulation and the results are compared with measurements of an ion radiation system of the present invention. Radiation transport in a magnetic field has been extensively simulated for electron beams (Ma et al. 2001b, Lee and Ma 2000). Software is implemented and verified for protons to obtain proton energy, angular and spatial distributions at the exit window of the laser-proton device. The geometry of an ion radiation system of the present invention is used in the simulations. The characteristics of the anticipated beams are studied to evaluate their advantages and disadvantages for radiation oncology application.

Figure 18:
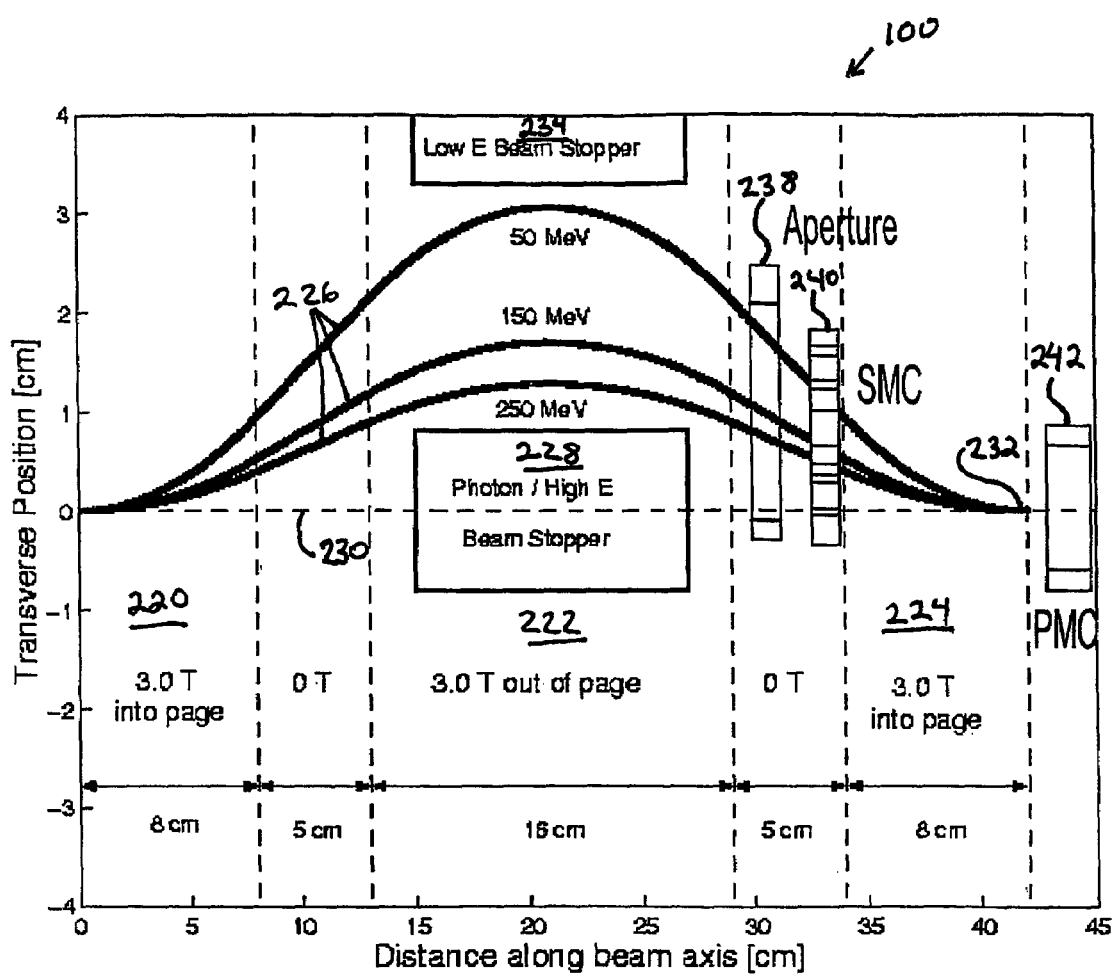
FIG. 18 shows a schematic of one embodiment of the ion selection system of the present invention showing tracks calculated for 50, 150 and 250 MeV protons in 3 T magnetic fields (moving from left to right). Protons having energy levels within an energy range pass by the beam stoppers and recombine through an exit collimator and the primary monitor chamber (PMC). The high-energy proton stopper also serves as a photon stopper and the electrons are deflected downward and terminated by the electron stopper. The secondary monitor chamber (SMC) measures both the energy spread and intensity change.
Figure 19:
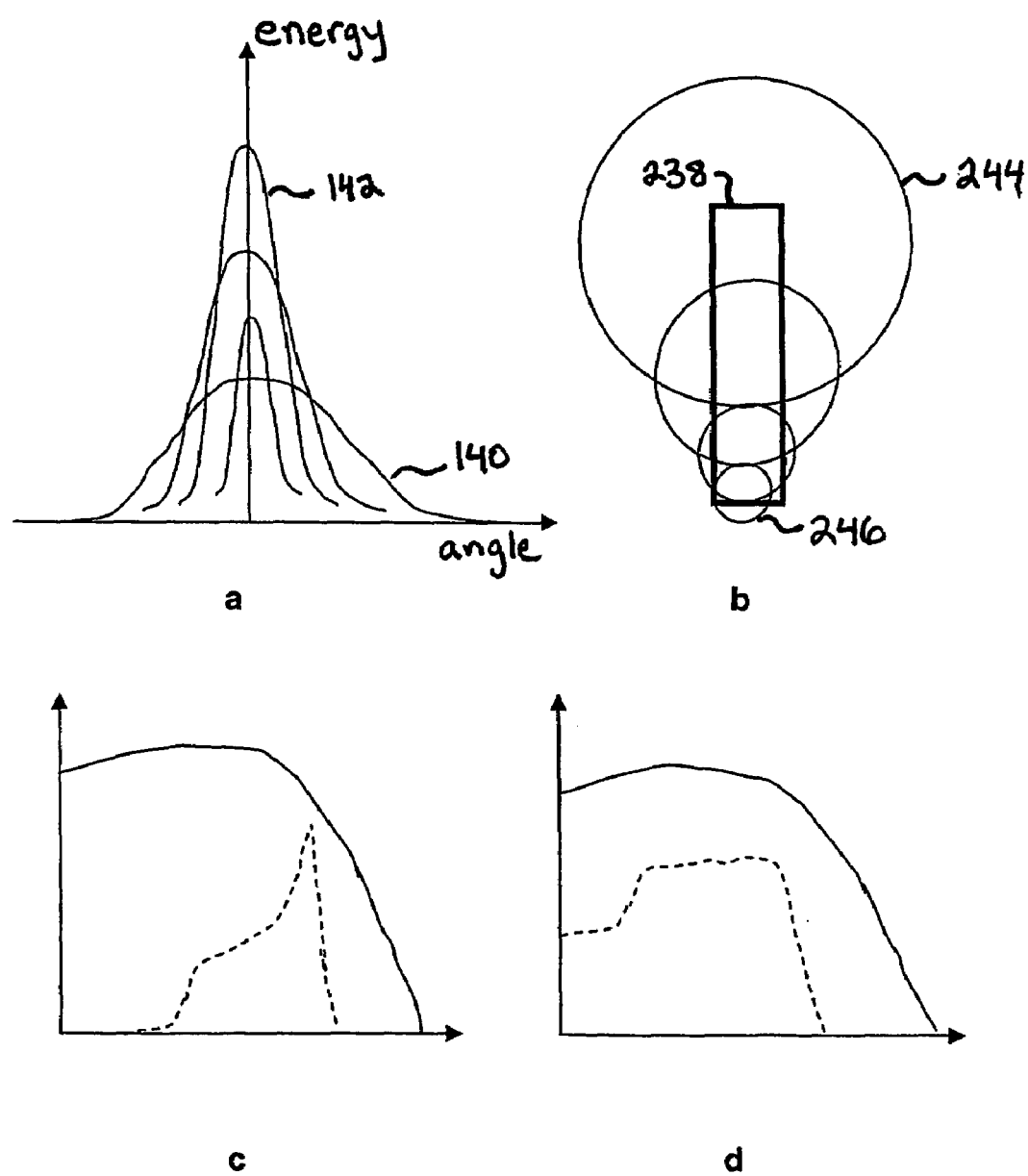
FIG. 19 shows (a) angular distributions of protons in a raw beam (each curve represents one energy); (b) spatial spread of protons after going through magnet fields (each circle represents one energy) and a rectangular aperture to select desired energy levels; (c) Energy spectrum of raw protons (solid) and selected protons (dashed); and (d) Depth dose curve of raw protons (solid) and selected protons (dashed).

Analytical study of ion selection and beam collimation: To use the proton beams for treatment, one typically removes the contaminant photons, neutrons and electrons from the beam using any of a variety of beam stopping and shielding materials. In preferred embodiments of the ion selection systems of the present invention, low-field magnets are used to separate the four major radiation components. As shown schematically in FIG. 18, several 3 Tesla magnetic fields (220, 222, 224) are used to deflect protons a small angle. A photon beam stopper (228) is placed on the beam axis (230). Suitable beam stoppers (228, 234) are used to remove unwanted low- and high-energy protons. The matching magnetic field setup in this embodiment assists the recombining of the selected protons, and the final beam is collimated by the primary and secondary collimators 242 and 240, respectively. The opening of the collimator is typically small (about 0.5 cm×0.5 cm), and the collimators are typically greater than about 10 cm in total thickness. Scattered protons from the beam stoppers 228, 234 and the protons missing the opening of the aperture are not transmitted through the collimator opening. As the bremsstrahlung photons and neutrons are also forward directed, a 1–2 cm wide, 10 cm thick tungsten stopper typically stops all the direct particles and the scattered particles are terminated by the shielding materials (not shown). Electrons typically are deflected downward by the magnetic field (220) and absorbed by an electron stopper. FIG. 19(*a*) shows the proton energy and angular distributions before and after ion selection. Lower energy protons (140) typically have larger angular spread compared to higher energy protons (142). In FIG. 19(*b*), lower energy protons (140) they typically spread over a larger area (244) spatially after going through the magnets compared to the spatial spread (246) of higher energy protons. An aperture (238) typically is used to select the desired energy components. FIG. 19(*c*) shows the energy spectrum of raw protons (solid line) and that of the resulting selected protons (dashed line). FIG. 19(*d*) shows the depth dose curve of raw protons solid line) and that of the resulting selected protons (dashed line). A secondary monitor chamber (240) ("SMC" in FIG. 18) measures the intensity of each energy component. A primary monitor chamber (242) ("PMC" in FIG. 18) is also provided. Various ways of monitoring ion beams and control systems are disclosed in U.S. patent application Ser. No. 09/757,150 filed Jan. 8, 2001, Pub. No. U.S. 2002/0090194 A1, Pub. Date Jul. 11, 2002, "Laser Driven Ion Accelerator", the portion of which pertaining to monitoring ion beams and control systems is incorporated by reference herein. A suitable laser-proton beam, as selected by the ion selection system (100) of the present invention, typically has an energy spectrum suitable for a desired treatment depth range (uniform dose over that range). By using a plurality of beams, a conformal and uniform dose coverage in the beam direction is achieved for essentially any target shape and depth.

The design parameters for the ion selection and collimating system using the experimental setup described above can be optimized by those skilled in the art. Because the proton beams are very small in cross-section, suitable magnetic field ("B-field") sources for providing high magnetic fields within a small space are used. Suitable magnets for providing such magnetic fields are readily available to those skilled in the art. The ion selection system of the present invention does not require strict B-field spatial distribution, for example, the fields may have a slow gradient or a fast gradient. Likewise, the opposing B-fields may be matched or mismatched. One skilled in the art can perform theoretical optimization studies on different magnets to determine various compact geometries. A suitable compact geometry is illustrated in FIG. 18, which provides dimensions of less than 50 cm in length and less than 40 cm in diameter. The properties of the primary beam for treatment and the leakage through the collimating system together with other contaminant particles can be investigated using a numerical simulation program for further treatment planning dose calculations. Criteria for proton spectra and beamlet dose distributions are determined based on the minimum requirements for beam penumbra laterally and in the depth direction for treatment optimization. The results are used to guide further optimization work on collimator design and proton energy selection and modulation studies. Source models for the proton beams are also investigated so that for patient simulation, the phase-space information can be reconstructed from the source models rather than using large phase-space data files (inefficient for simulation and large disk space, Ma 1998, Ma et al. 1997) or simulating the laser proton device every time. Beam commissioning procedures are also established by one skilled in the art for validating the source model parameters and the beam reconstruction accuracy.

Figure 20:
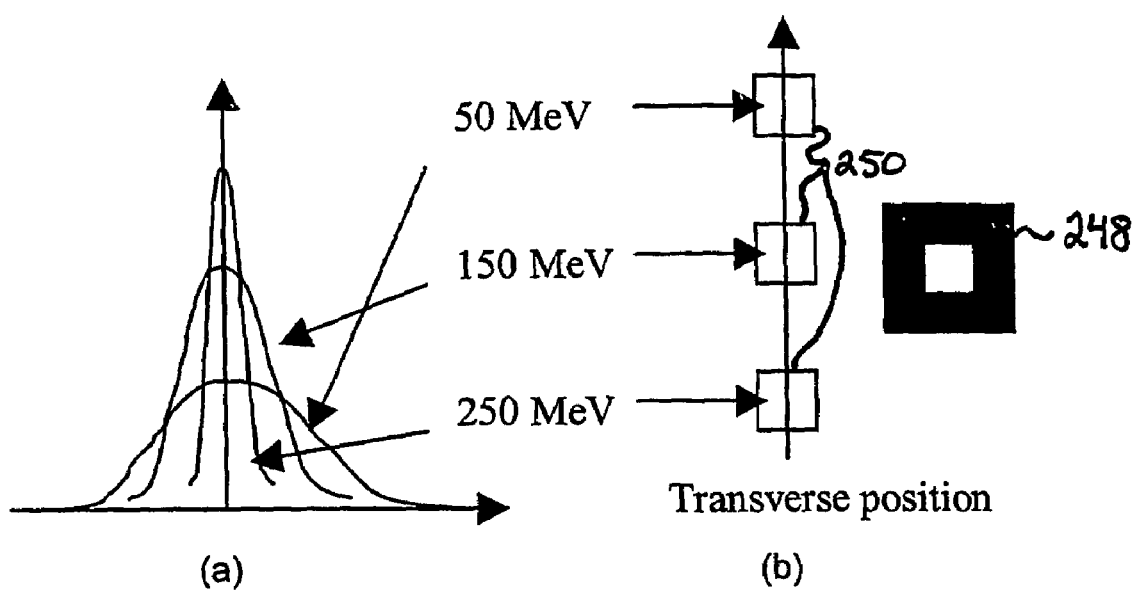
FIG. 20 depicts (a) angular distributions for different energy protons in the raw laser-proton beam; (b) spatial spreads of protons of different energy levels after going through a square collimator and the magnets. A square aperture on the right hand side of (b) is used to select a desired energy.

FIG. 20 illustrates one set of design principles of the present invention of the ion selection mechanism. Since different laser-protons have different angular distributions (three energy levels are shown in FIG. 20(a)), a collimator (e.g. 108, FIG. 1) is typically used (i.e., positioned at the distance along beam axis 0 cm in FIG. 18) to define the field size. When the initial collimator (108) has a square opening, and the polyenergetic collimated protons of different energy levels have passed through the magnet fields, the collimated protons will reach different transverse locations (250) (as shown at the distance 30 cm in FIG. 18). FIG. 20 (a and b) shows the square fields of 50, 150 and 250 MeV protons, which are well separated spatially. The transverse plane is referred to as "the energy space (plane)" as different proton energy levels typically occupy different transverse locations. Because of the finite size of the initial collimator there typically is some overlap of proton energy levels, which typically depends on the size of the initial collimator, the magnetic field strength and the distance from the energy plane to the initial collimator. For selecting the desired energy of this embodiment, a second collimator is typically used, which is typically positioned at the corresponding transverse location. As shown in FIG. 20(b), a square aperture (248) (on the right hand side) is used to select either the 50, 150 or the 250 MeV field. A differential transmission chamber (the secondary monitor chamber, SMC in FIG. 18) is used to measure the intensity of each energy component. Multiple laser pulses are typically provided to produce a combination of protons to provide a desired spectrum. The desired proton energy spectrum is used to produce a therapeutically high energy polyenergetic positive ion beam, which provides uniform dose distributions over a desired depth range.

Another embodiment of the ion selection system of the present invention is to use variable aperture sizes at the energy space (plane) to select both an energy and the total number of protons of that energy (intensity) simultaneously. This embodiment typically requires fewer laser pulses to achieve a desired proton spectrum compared to the preceding embodiment. This variable aperture size embodiment preferably uses an elongated aperture at the energy space with variable widths at different transverse (energy) locations. Without being bound by a particular theory of operation, this design allows for energy and intensity selection simultaneously from the same laser pulse. This appears to be a highly efficient way to use a polyenergetic laser-proton beam to achieve a uniform dose over a depth range for radiation therapy. A variable energy aperture size typically uses a subsequent differential magnetic system to recombine the fields of different proton energy levels to a similar field size.

In certain embodiments, a secondary collimation device (138) (FIG. 1) is typically provided to define the final field size and shape of the positive ions that form the therapeutically suitable high energy polyenergetic positive ion beam. Small shaped beams (e.g., squares, circles, rectangles, and combinations thereof) are provided in to modulate the intensity of individual beamlets so that a conformal dose distribution to the target volume can be achieved. Since the individual proton beams can have variable energy spectra for providing a uniform dose distribution over the depth range of the target volume, EIMPT can be used to produce a more uniform proton dose distribution in the target than photon IMRT (Lomax 1999, Ma et al. 2001).

Another method of modulating the spatially separated high energy polyenergetic positive ion beam is to deliver EIMRT using a plurality of individual narrow energy polyenergetic proton beams at a time with a relatively large field that covers at least a portion of the cross-section of the target volume at the corresponding depth (i.e., the depth of the Bragg Peak). In this embodiment, there is provided a modulatable secondary collimation device that is capable of modulating the spatially separated beam. The modulatable secondary collimation device may have a variable shape, which can be realized using an aperture, as described earlier, such as a multileaf collimator (MLC). A number of laser pulses are typically provided using this embodiment to treat a target volume. While the aperture that modulates the energy levels typically moves in the transverse direction to select a desired energy spectrum to cover the depth range of at least a portion of the entire target volume, the modulatable secondary collimation devices (e.g., the MLC) are capable of changing the field shape of the recombined beam to enclose at least a portion of the cross-section of the target volume at the corresponding depths.

The methods described herein for the ion selection systems (100) of the present invention may suitably be performed using the devices and instrumentalities described herein. Because the proton beams are typically small in cross-section, it is possible to establish a high magnetic field within a small space. Certain embodiments of the present invention do not require strict B-field spatial distribution, rather, the magnetic fields may have a slow gradient, they may be spatially overlapping, or both. Suitable embodiments of the present invention will include at least two magnetic field sources that have matching, opposite, B-fields. For example, the ion selection system geometry provided in FIG. 18, which is less than 50 cm in length and less than 40 cm in diameter, includes a first magnetic field source (220) of 3.0 T into the page, a second magnet field source (224) of 3.0 T into the page, and a third magnetic field source (222) of 3.0 T out of the page. The geometry may be further reduced in the beam direction by using higher magnetic fields, smaller photon beam stoppers, or both.

Improvement of Monte Carlo dose calculation tools: Dose calculation tools for EIMPT are also provided in accordance with the invention. Dose calculation is performed in treatment optimization for laser accelerated proton beam therapy because the dose distributions of small proton beamlets are significantly affected by the beam size and heterogeneous patient anatomy. Patient dose calculations are estimated using the GEANT3 system. The code is designed as a general purpose Monte Carlo simulation. The dose distributions shown in FIG. 16 (*a–d*) took about 100 hours of CPU time on a Pentium III 450 MHz PC. Much faster computers that are currently available should be able to reduce this computation time by at least about one or two orders of magnitude. For accelerating dose calculation, a fast proton dose calculation algorithm has been developed based on conventional photon and electron Monte Carlo dose calculation algorithms (Ma et al. 1999a–b, 2000ab, Deng et al. 2000ab, Jiang et al. 2000a, 2001, Li et al. 2000, 2001). Various variance reduction techniques have been implemented in the code to speed up the Monte Carlo simulation. These include "deterministic sampling" and "particle track repeating" (Ma et al. 2000b, Li et al. 2000), which are very efficient for charged particle simulations. The implementation of this fast Monte Carlo code is tested using the GEANT3 code. The source models are also implemented to reconstruct the phase-space parameters (energy, charge, direction and location) for the proton pencil beams emerging from the laser proton therapy device during a Monte Carlo dose calculation. Suitable software is available (Moyers et al 1992, Ma et al. 1999b) that can be adapted for use in treating patients with laser-accelerated polyenergetic positive ions. Such software first converts the patient CT data into a simulation phantom consisting of air, tissue, lung and bone. Based on the contours of the target volume and critical structures, the software computes the dose distributions for all the beamlets of different spectra, incident angles (e.g., gantry angles specified by the planner), and incident locations (e.g., within a treatment port/field). The final dose array for all the beamlets is provided to the treatment optimization algorithm, as described further below.

Improvement of treatment optimization tools: In certain embodiments, improved treatment optimization tools for EIMPT are also provided. A treatment optimization algorithm has been developed based on typical polyenergetic proton beams generated from a typical laser proton accelerator and actual patient anatomy. Commonly used "inverse-planning" techniques include computer simulated annealing (Webb 1990, 1994), iterative methods (Holmes and Mackie 1994a, Xing and Chen 1996), filtered back projection and direct Fourier transformation (Brahme 1988, Holmes and Mackie 1994b). Considering the calculation time and the possible complexity with proton beams, the iterative optimization approach (based on a gradient search) is suitably adopted. This is based on iterative optimization algorithms for photon and electron energy- and intensity-modulation (Pawlicki et al. 1999; Jiang 1998, Ma et al. 2000b, Jiang et al. 2000b). Improved algorithms for energy- and intensity-modulated proton beams are tested. Further improvements of the algorithm is carried out in view of the special features of the realistic proton beams. The "optimizer" performs the following tasks: (1) takes the beamlet dose distributions from the dose calculation algorithm (see above), (2) adjusts the beamlet weights (intensities) to produce the best possible treatment plan based on the target/critical structure dose prescriptions, and (3) outputs the intensity maps (beamlet weighting factors) for all the beam ports and gantry angles for beam delivery sequence studies.

Treatment plan comparison: The present invention has been evaluated for the treatment modality for prostate cancer. Comparisons are made of treatment plans generated by EIMPT using laser-accelerated proton beams with those generated by existing beam modalities such as conventional photon and proton beams and photon IMRT. A group of 20 clinical cases for prostate alone, prostate+seminal vesicles, and prostate+seminal vesicles+lymph nodes have been performed using EIMPT under the same conditions as for conventional radiotherapy treatments using conventional photons and protons and photon IMRT. The treatment plans are compared with those using a commercial RTP system for conventional photon beams with 4 or 6 photon fields (the FOCUS system) and a commercial treatment optimization system for IMRT with 5–9 intensity modulated photon fields (the CORVUS system). These cases are also planned using the proton treatment planning module in the FOCUS system, for conventional proton treatments with 2–6 fields.

The plans are evaluated using isodose distributions, DVHs, TCP, NTCP and other biological indices with emphasis on target coverage, target dose homogeneity and normal tissue sparing. The same objective (penalty) functions are used for both proton EIMPT and photon IMRT, under similar conditions. The "goodness" of a treatment plan is judged based on the appearance of the isodose distributions and on DVH, TCP, NTCP and other biological indices. A significantly improved plan is considered to possess one or more of the following: (a) more uniform (5–10%) dose within the target volume, much less (moderate vs. high or low vs. moderate) dose to the immediately adjacent normal structures, (b) a significantly reduced exit/scatter dose (by a factor of two or more) to remote organs, and (d) an unambiguously improved dose distribution. Furthermore, a physician typically makes a clinical judgment as to whether a particular plan would be used and provide reasons justifying this decision.

Production of Radioisotopes. The present invention also provides methods of producing radioisotopes using the laser-accelerated high energy polyenergetic ion beams provided herein. The production of 2-deoxy-2-$^{18}$F fluoro-D-glucose ("[$^{18}$F]FDG") is carried out by proton bombardment of the chemical precursors leading to the radioisotopes. These processes use proton beams generated using traditional cyclotron and synchrotron sources. For example, J. Medema, et al. [http://www.kvi.nl/~agorcalc/ecpm31/abstracts/medema2.html] have reported on the production of [$^{18}$F] Fluoride and [$^{18}$F] FDG by first preparing [$^{18}$F] fluoride via the $^{18}$O(p, n) [$^{18}$F] nuclear reaction in $^{18}$O enriched water, and producing the [$^{18}$F]FDG by recovering the [$^{18}$F]fluoride via the resin method and the cryptate drying process. The present invention provides high energy polyenergetic ion beams suitable for use in this process of preparing radioisotopes. Thus, the process of producing radioisotopes includes the steps of forming a high energy polyenergetic proton beam as described herein to provide an appropriate particle, target and beam current. A target precursor is filled with $H_2^{18}O$. The high energy polyenergetic proton beam irradiates the target precursor until a preselected integrated beam current or time is reached. The target pressure is typically monitored by a pressure transducer. When the integrated beam current or the time is reached the [$^{18}F$]fluoride is used for chemically synthesizing [$^{18}F$] FDG. The final product is isotonic, colorless, sterile, and pyrogen free and is suitable for clinical use.

Figure 23:
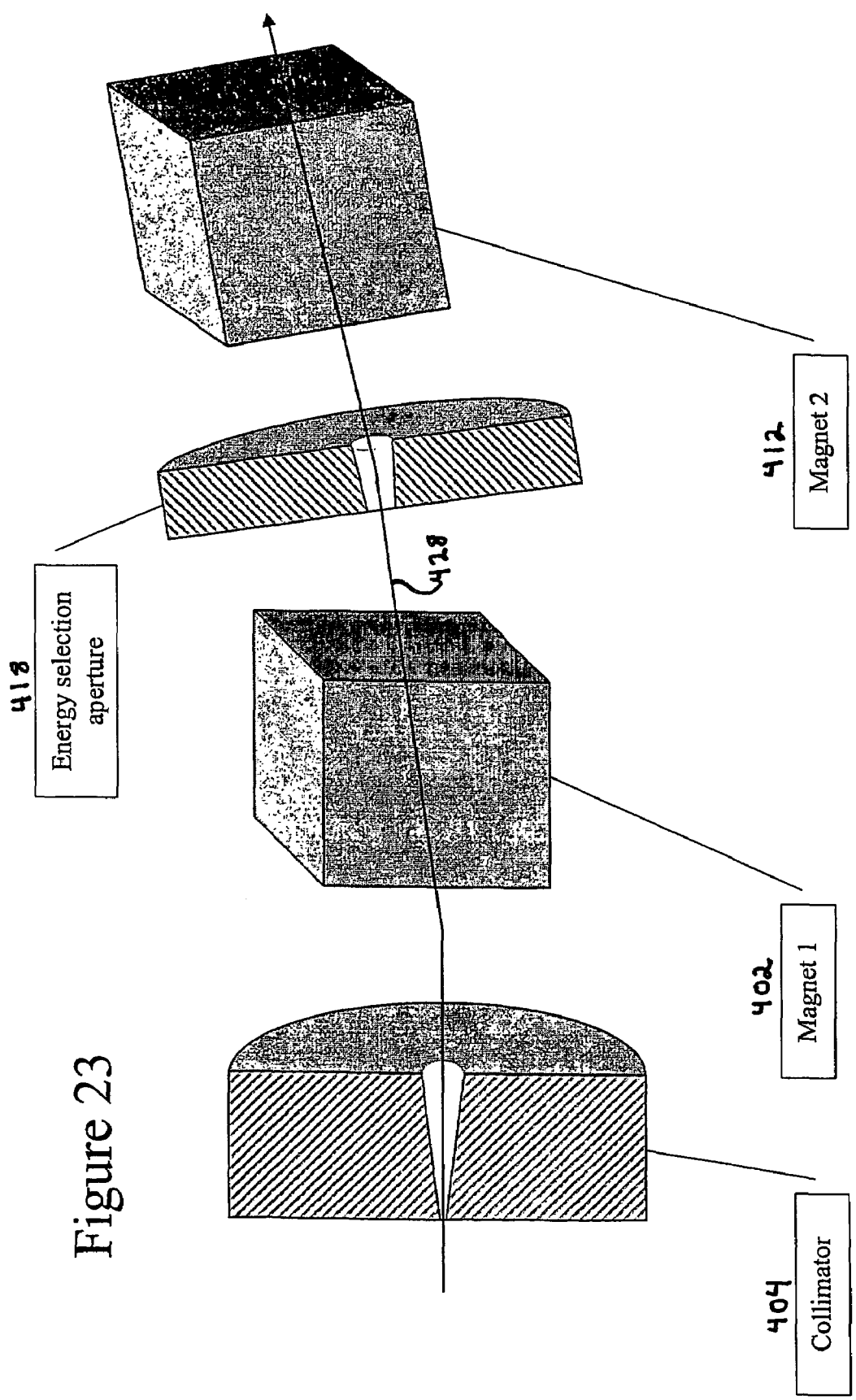
FIG. 23 depicts a sectional view of an ion selection system depicted in FIG. 22.

Various alternate embodiments of the present invention are further depicted in FIGS. 21–44, in which the ion tracks are illustrated to provide a general position and orientation of the ions. For example, FIGS. 21, 23 (schematic cross sections) and 22 (perspective) depicts an embodiment of an ion selection system (100) composed of a collimation device (408) capable of collimating a laser-accelerated high energy polyenergetic positive ion beam, the laser-accelerated high energy polyenergetic ion beam having a plurality of high energy polyenergetic positive ions; a first magnetic field source (magnet 202) capable of spatially separating the high energy polyenergetic positive ions according to their energy levels; an aperture (418) capable of modulating the spatially separated high energy polyenergetic positive ions; and a second magnetic field source (magnet 412) capable of recombining the modulated high energy polyenergetic positive ions.

Figure 21:
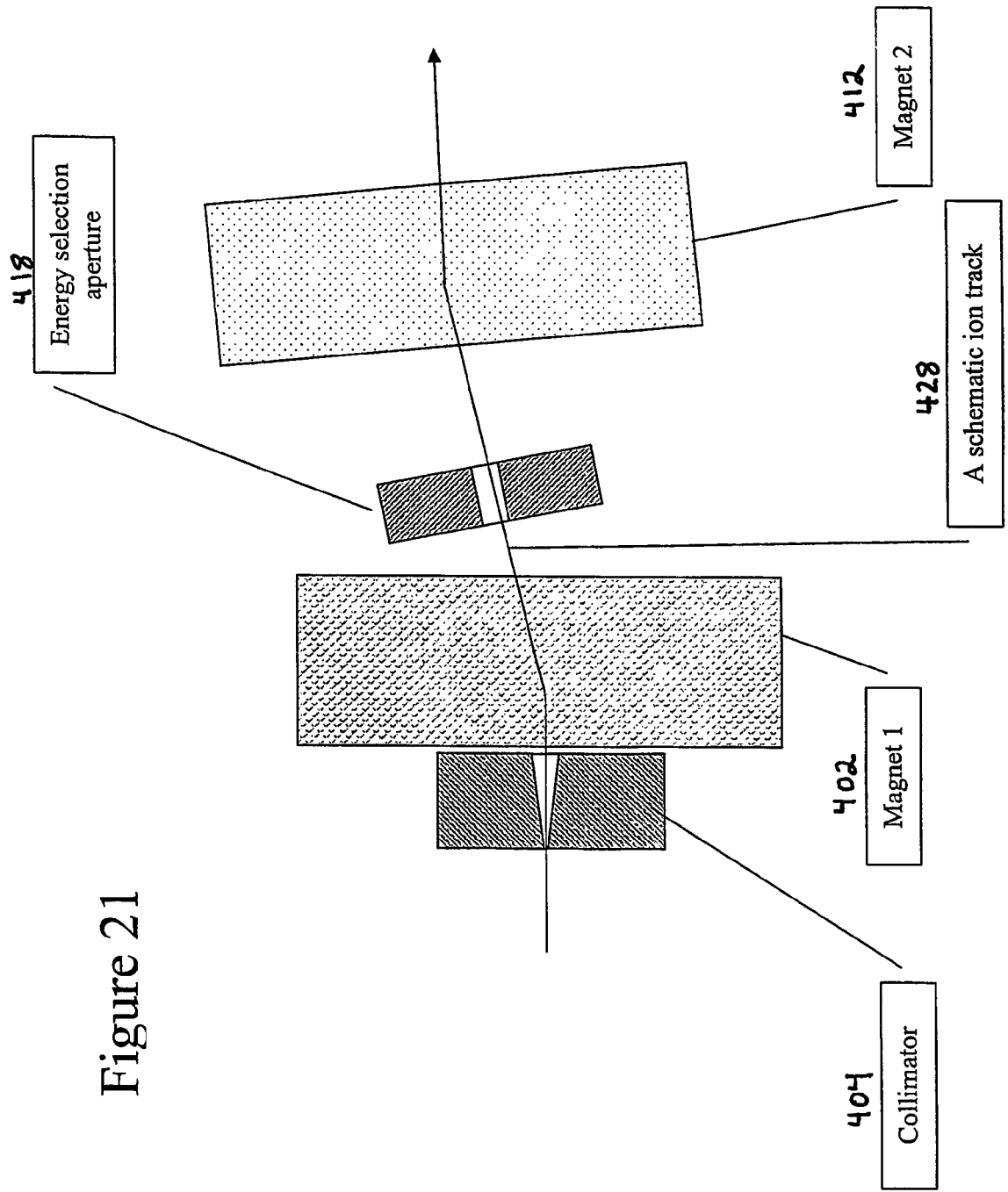
FIG. 21 depicts a sectional view of an embodiment of an ion selection system of the present invention.
Figure 22:
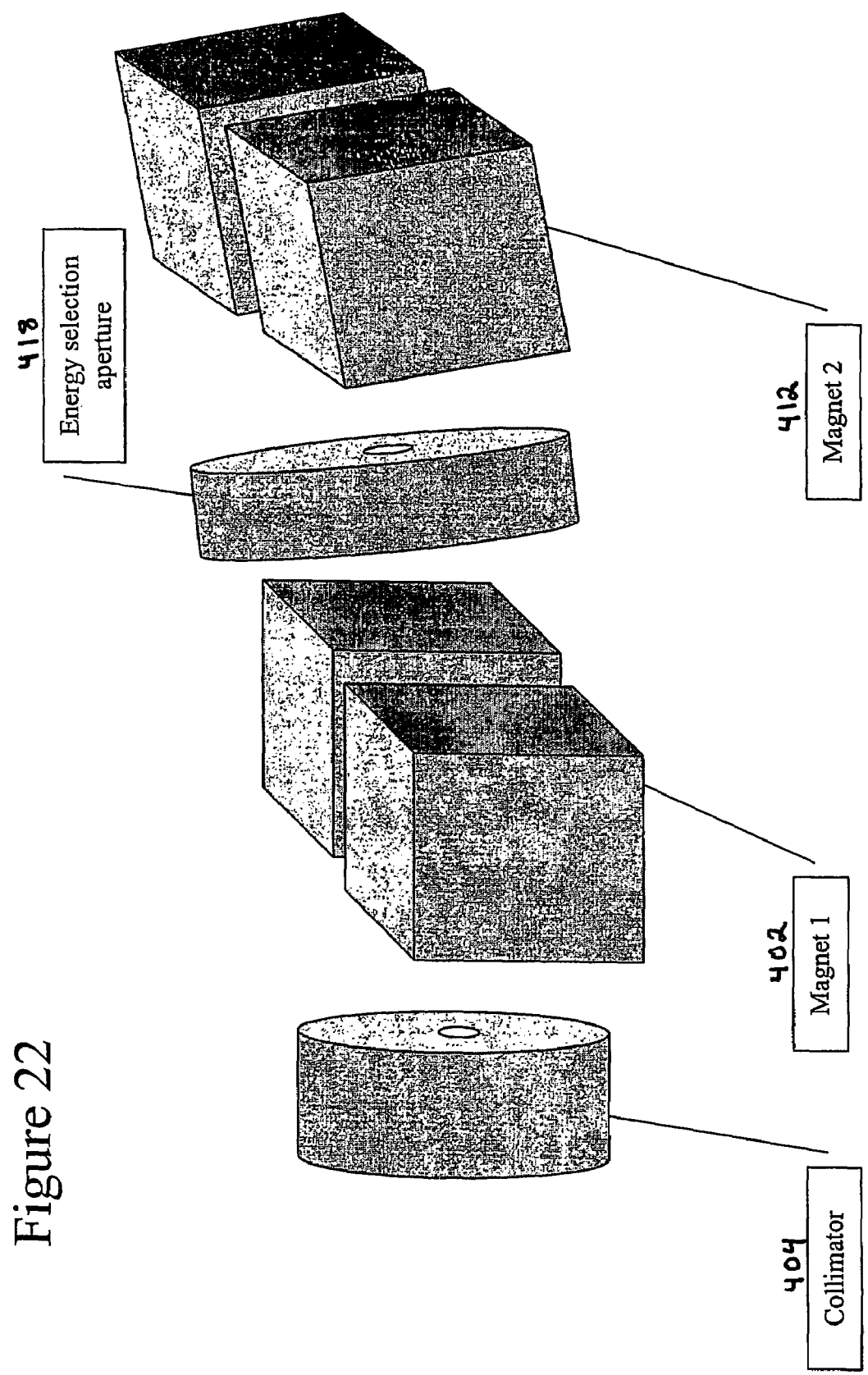
FIG. 22 depicts a perspective view of an embodiment of an ion selection system of the present invention.
Figure 24:
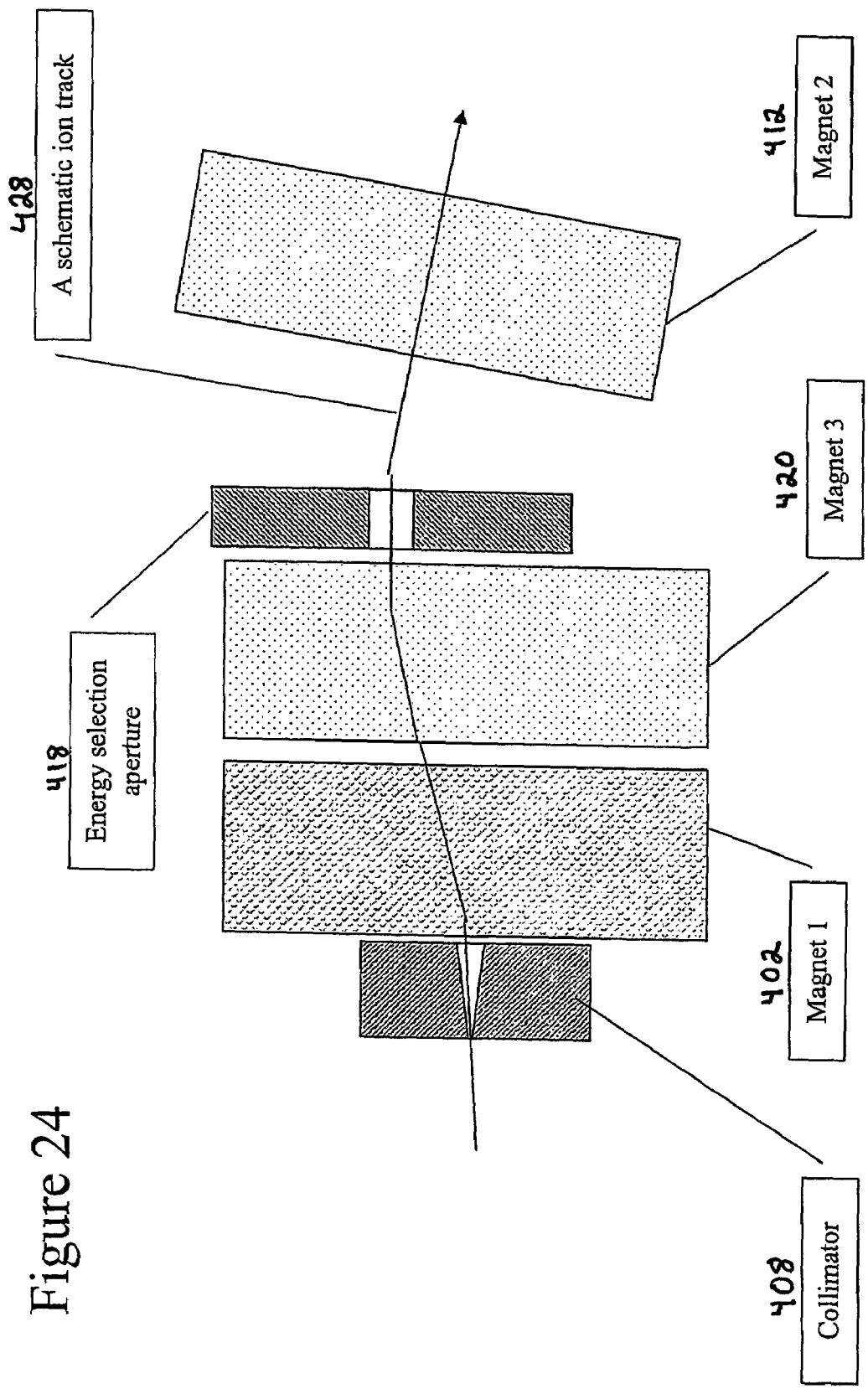
FIG. 24 depicts a sectional view of an embodiment of an ion selection system of the present invention.

FIG. 24 depicts a schematic of an embodiment of an ion selection system similar to that provided in FIG. 21 that further includes a third magnetic field source (magnet 420), the third magnetic field source capable of bending the trajectories (428) of the spatially separated high energy polyenergetic positive ions towards the aperture (418).

Figure 25:
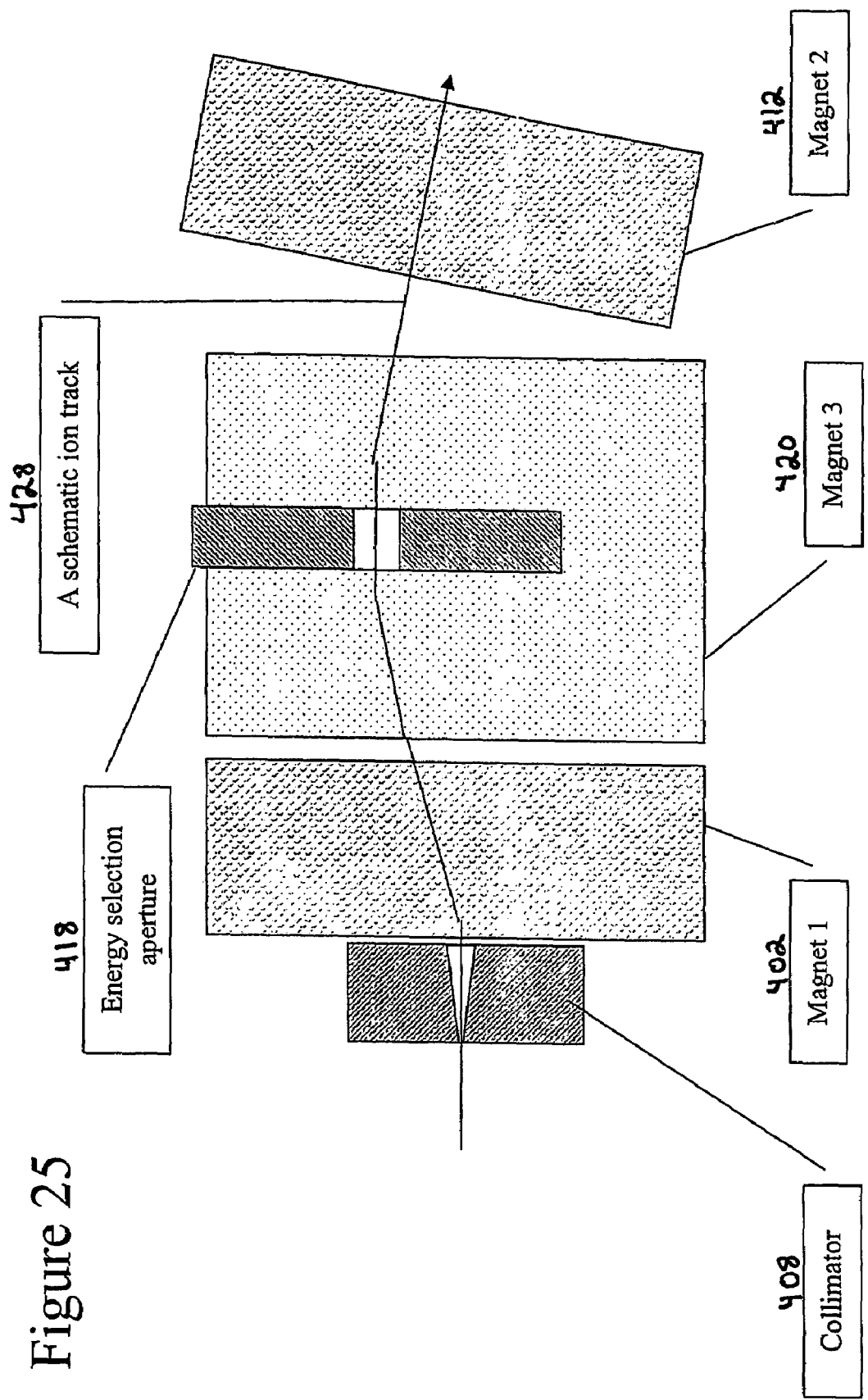
FIG. 25 depicts a sectional view of an embodiment of an ion selection system of the present invention.

FIG. 25 depicts a schematic of an embodiment of an ion selection system similar to that provided in FIG. 24 that shows the aperture (418) being placed inside the magnetic field of the third magnetic field source (magnet 420).

Figure 26:
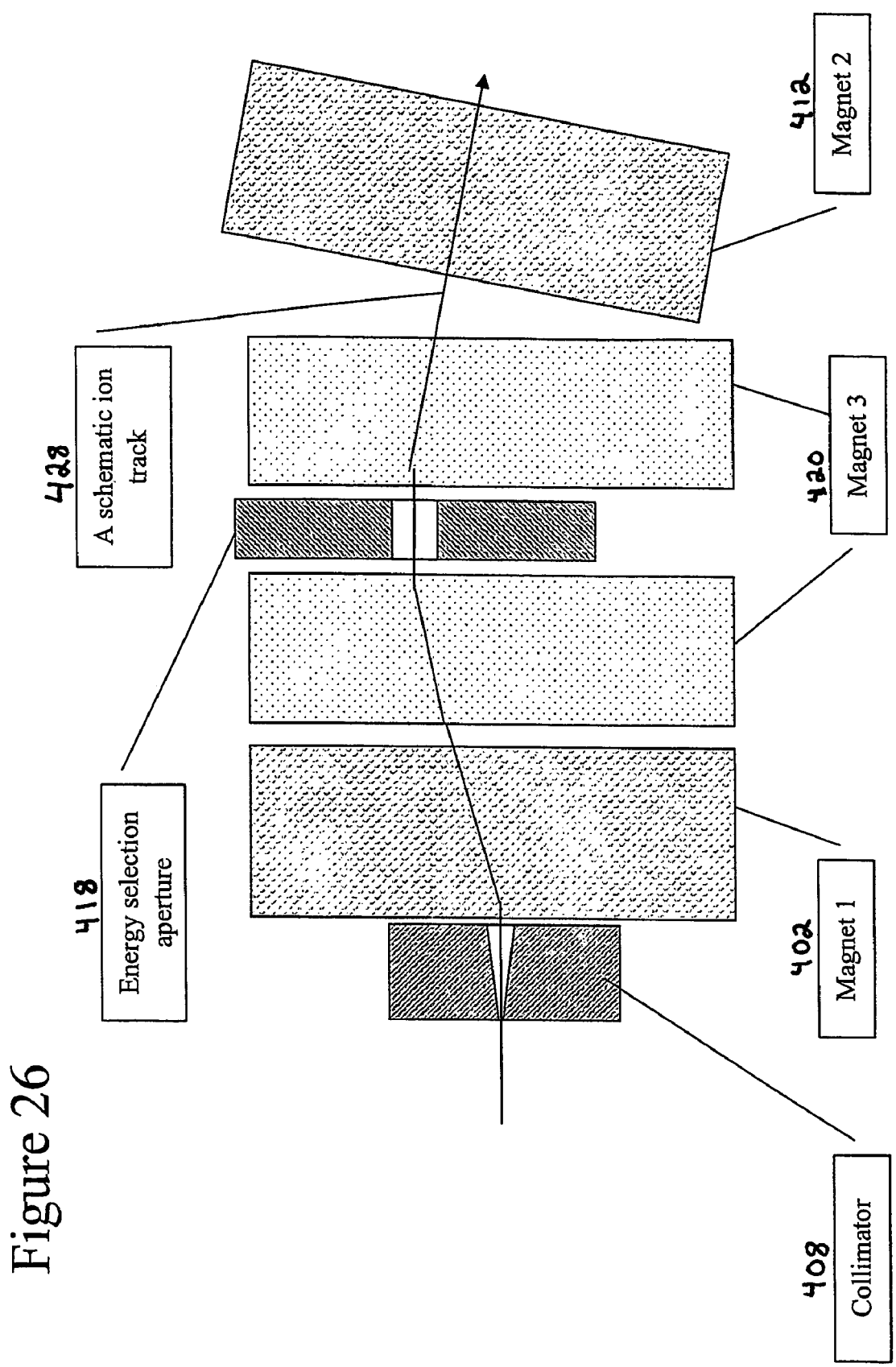
FIG. 26 depicts a sectional view of an embodiment of an ion selection system of the present invention.

FIG. 26 depicts a schematic of an embodiment of an ion selection system similar to that provided in FIG. 24 that shows the aperture (418) being placed outside of the magnetic field of the third magnetic field source (magnet 420), where the third magnetic field source is separated into two portions.

Figure 27:
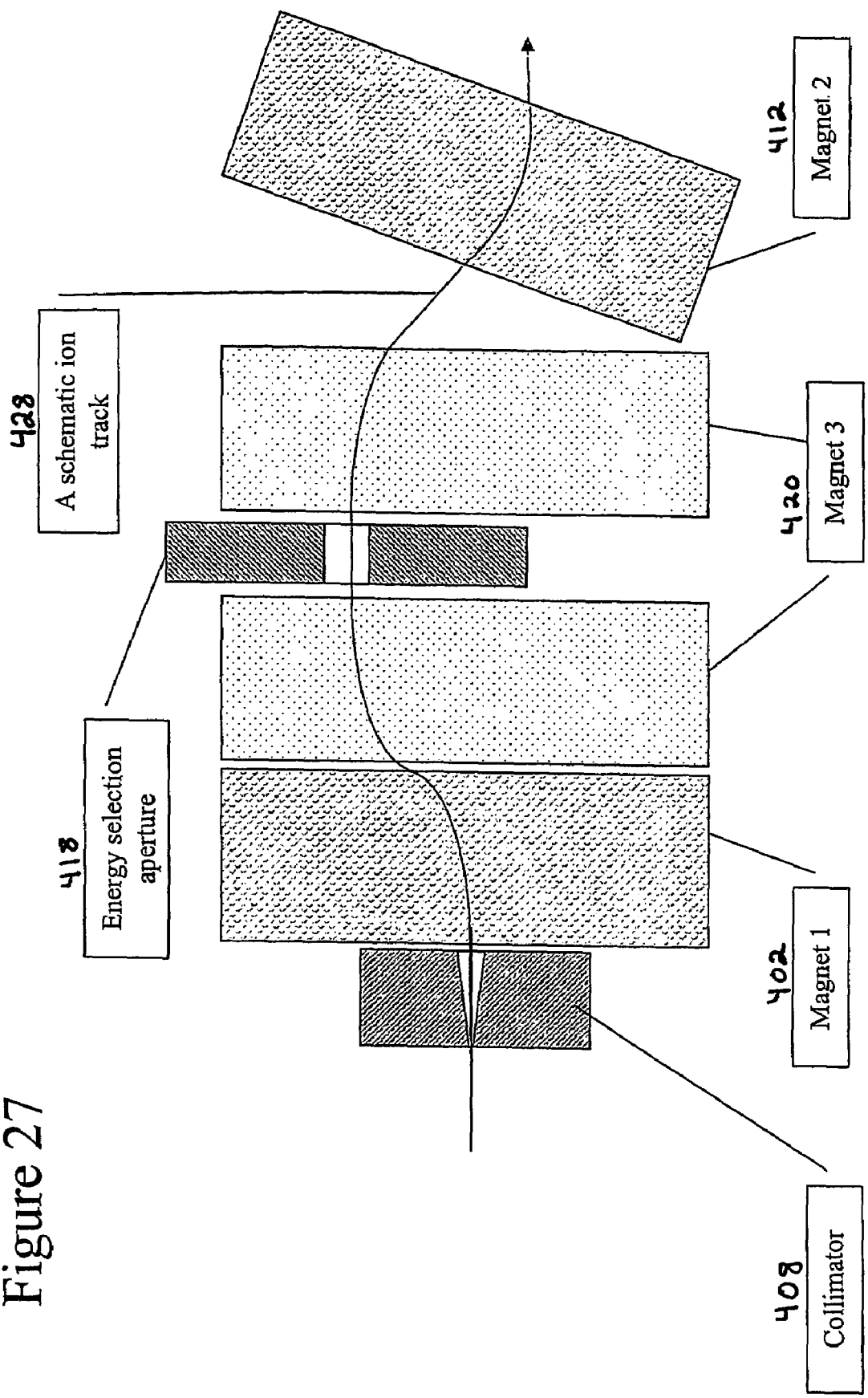
FIG. 27 depicts a sectional view of an embodiment of an ion selection system of the present invention.

FIG. 27 depicts a schematic of an embodiment of an ion selection system in which the magnetic field of the third magnetic field source (magnet 420) is capable of bending the trajectories (428) of the modulated high energy polyenergetic positive ions towards the second magnetic field source (magnet 412).

Figure 28:
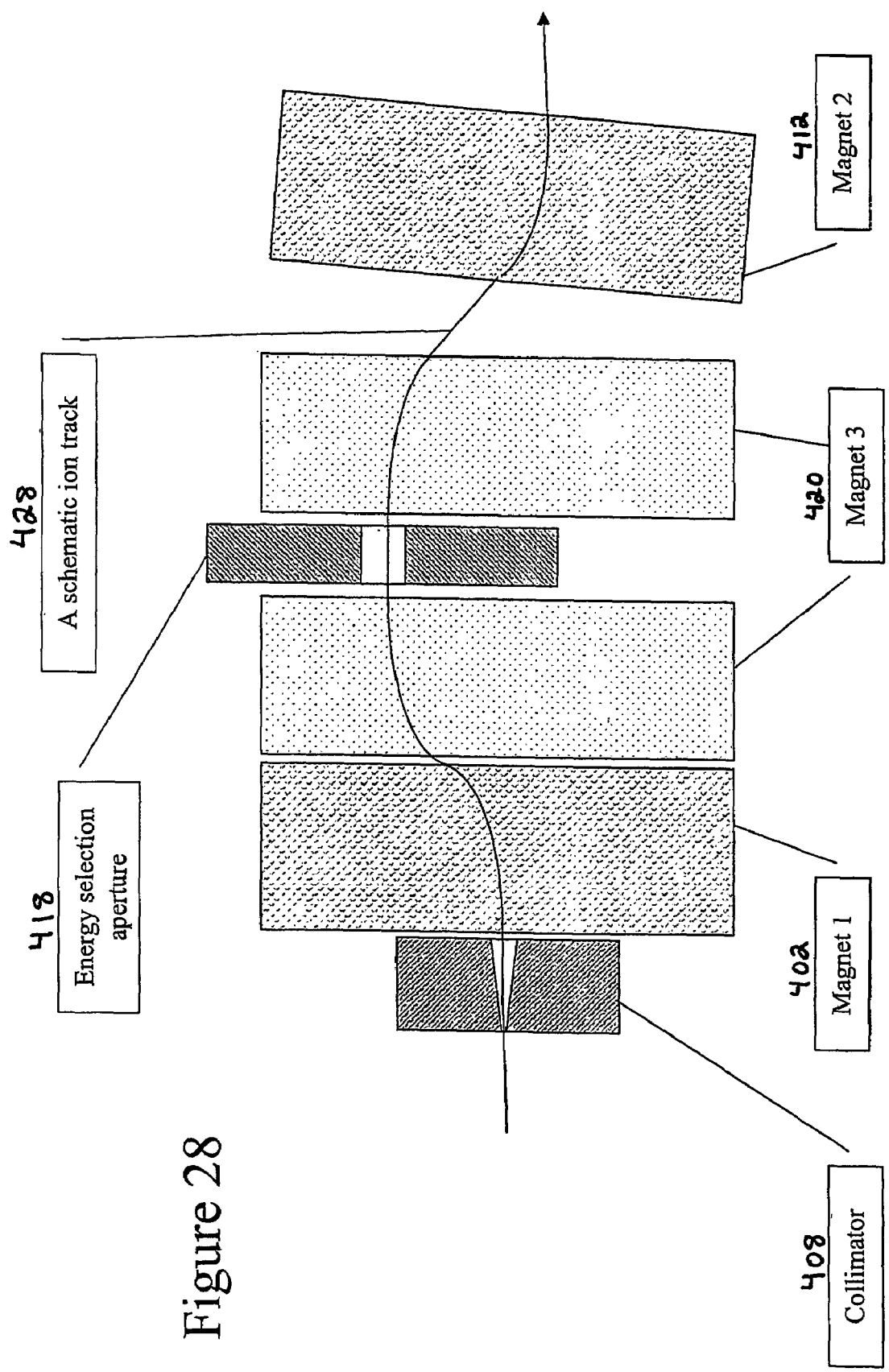
FIG. 28 depicts a sectional view of an embodiment of an ion selection system of the present invention.

FIG. 28 depicts a schematic of an embodiment of an ion selection system in which the second magnetic field source (magnet 412) is capable of bending the trajectories (428) of the modulated high energy polyenergetic positive ions towards a direction that is not parallel to the direction of the laser-accelerated high energy polyenergetic ion beam.

Figure 29:
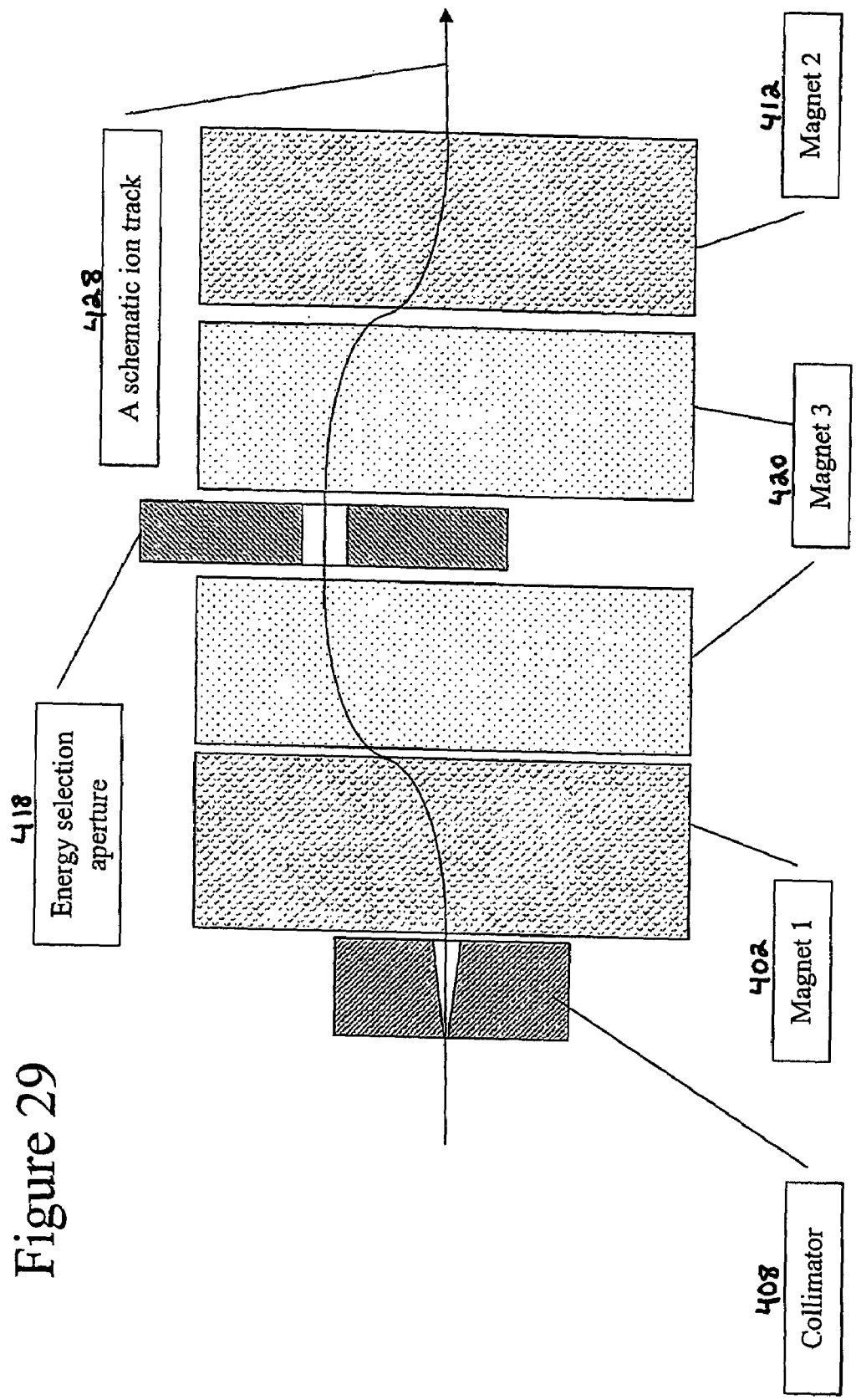
FIG. 29 depicts a sectional view of an embodiment of an ion selection system of the present invention.

FIG. 29 depicts a schematic of an embodiment of an ion selection system in which the second magnetic field source (magnet 412) is capable of bending the trajectories (428) of the modulated high energy polyenergetic positive ions towards a direction that is parallel to the direction of the laser-accelerated high energy polyenergetic ion beam.

Figure 30:
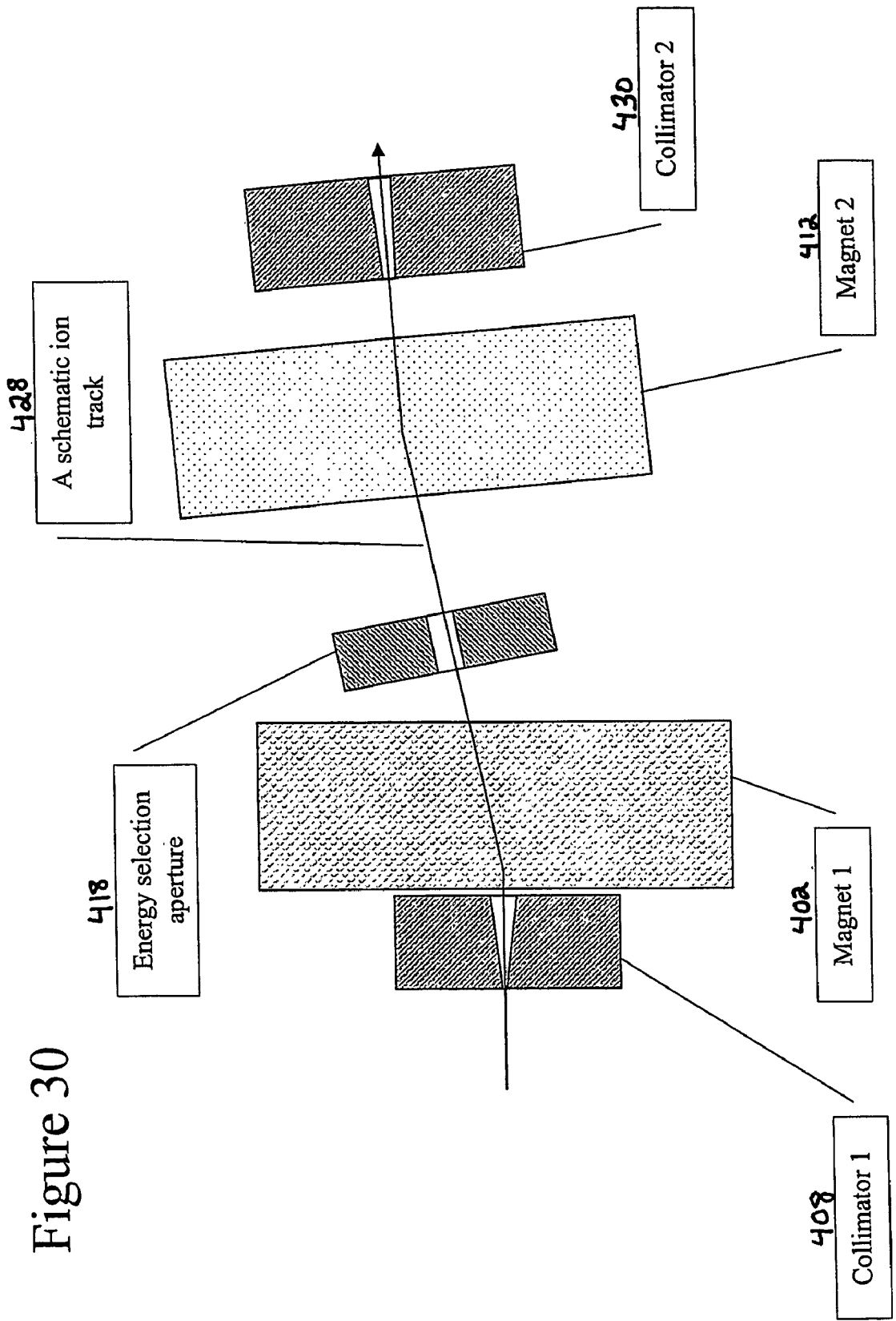
FIG. 30 depicts a sectional view of an embodiment of an ion selection system of the present invention.

FIG. 30 depicts a schematic of an embodiment of an ion selection system that further shows a secondary collimation device (430) capable of fluidically communicating a portion of the recombined high energy polyenergetic positive ions therethrough.

Figure 31:
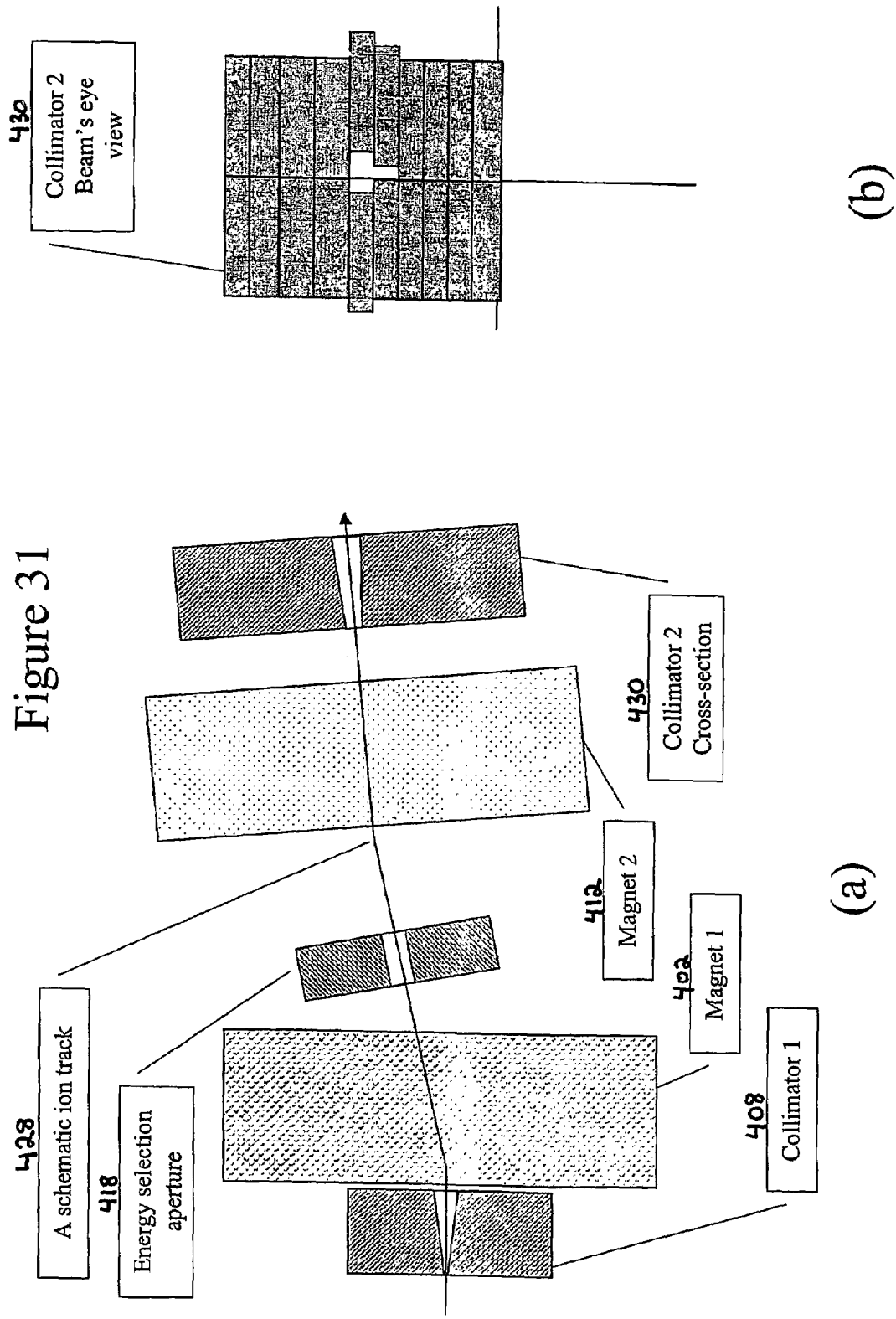
FIG. 31($a$) depicts a sectional view of an embodiment of an ion selection system of the present invention.

FIG. 31 depicts an embodiment of an ion selection system that shows a secondary collimation device (430) that is capable of modulating the beam shape of the recombined high energy polyenergetic positive ions.

Figure 32:
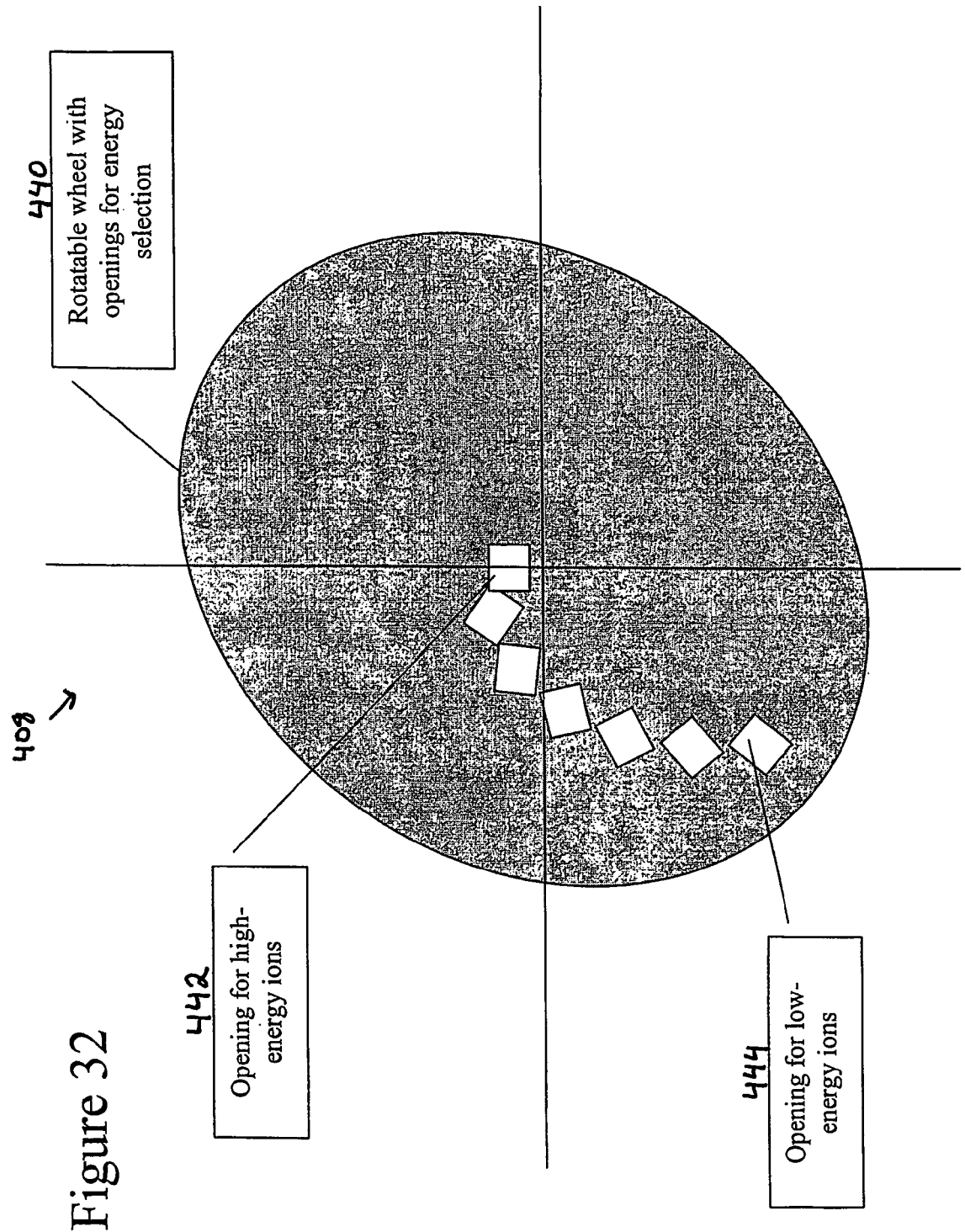
FIG. 32 depicts a schematic illustration of an energy selection aperture.

FIG. 32 depicts details of a rotatable wheel (440) with an aperture (418) having a plurality of openings (442, 444), each of the openings capable of fluidically communicating high energy polyenergetic positive ions therethrough.

FIG. 33 depicts details of an aperture that is a multileaf collimator (408) having openings (444, 442) that are capable of passing low energy ions, high energy ions, respectively, or a combination thereof.

Figure 34:
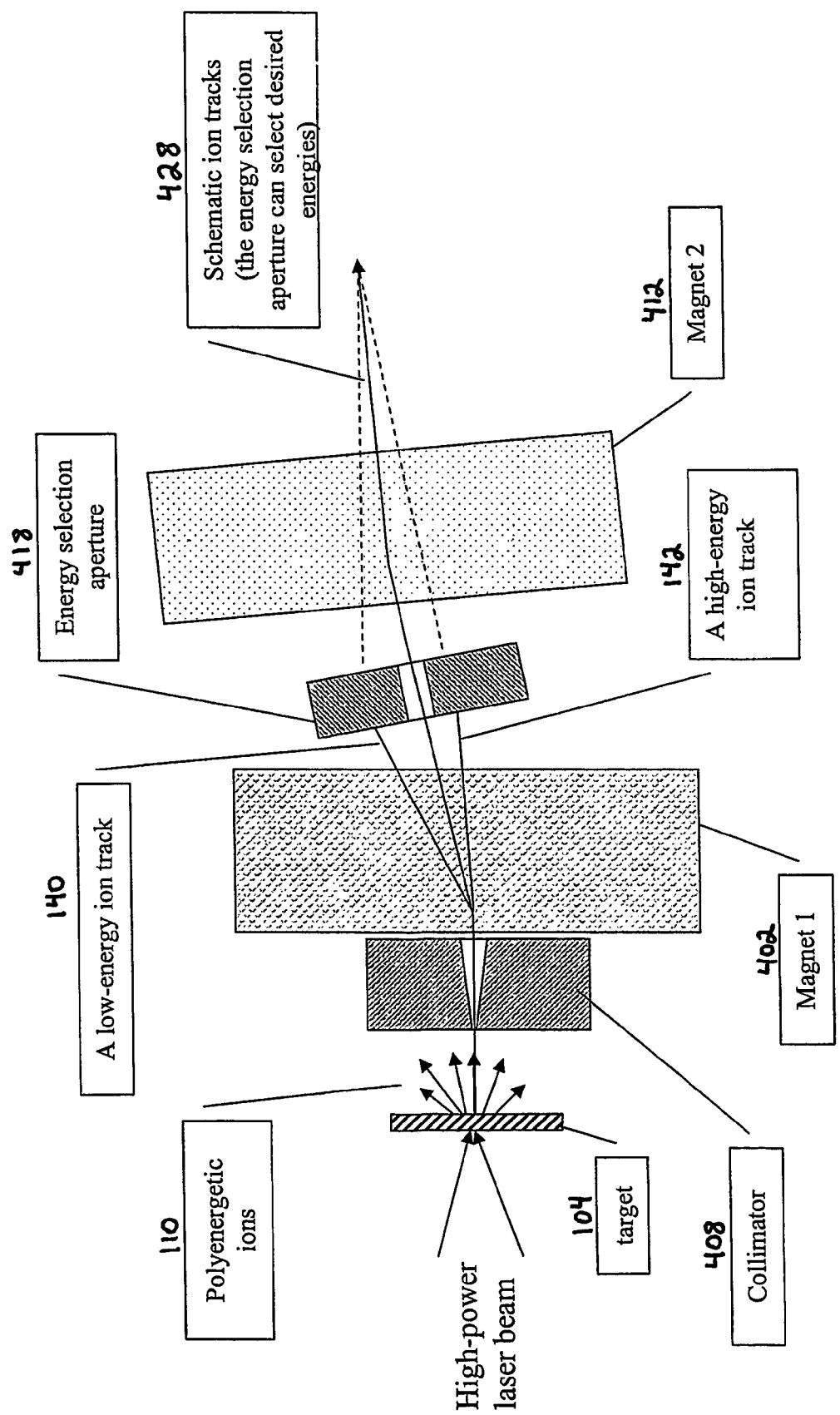
FIG. 34 depicts a sectional view of an embodiment of an ion selection system of the present invention.

FIG. 34 depicts how an ion selection system in accordance with the invention manipulates ion beams. This figure depicts the forming of a laser-accelerated high energy polyenergetic ion beam including a plurality of high energy polyenergetic positive ions (110), the high energy polyenergetic positive ions (110) characterized as having a distribution of energy levels. The collimating of the laser-accelerated ion beam (110) is performed using a collimation device (collimator 408), and the positive ions (140, 142) are spatially separated according to their energy levels using a first magnetic field (magnet 402). The spatially separated high energy polyenergetic positive ions are modulated using an energy selection aperture (418) and the modulated high energy polyenergetic positive ions are recombined (428) using a second magnetic field (magnet 412). In this embodiment, a portion of the positive ions are transmitted through the aperture, e.g., having energy levels in the range of from about 50 MeV to about 250 MeV, and other portions are blocked by the energy selection aperture (418).

Figure 35:
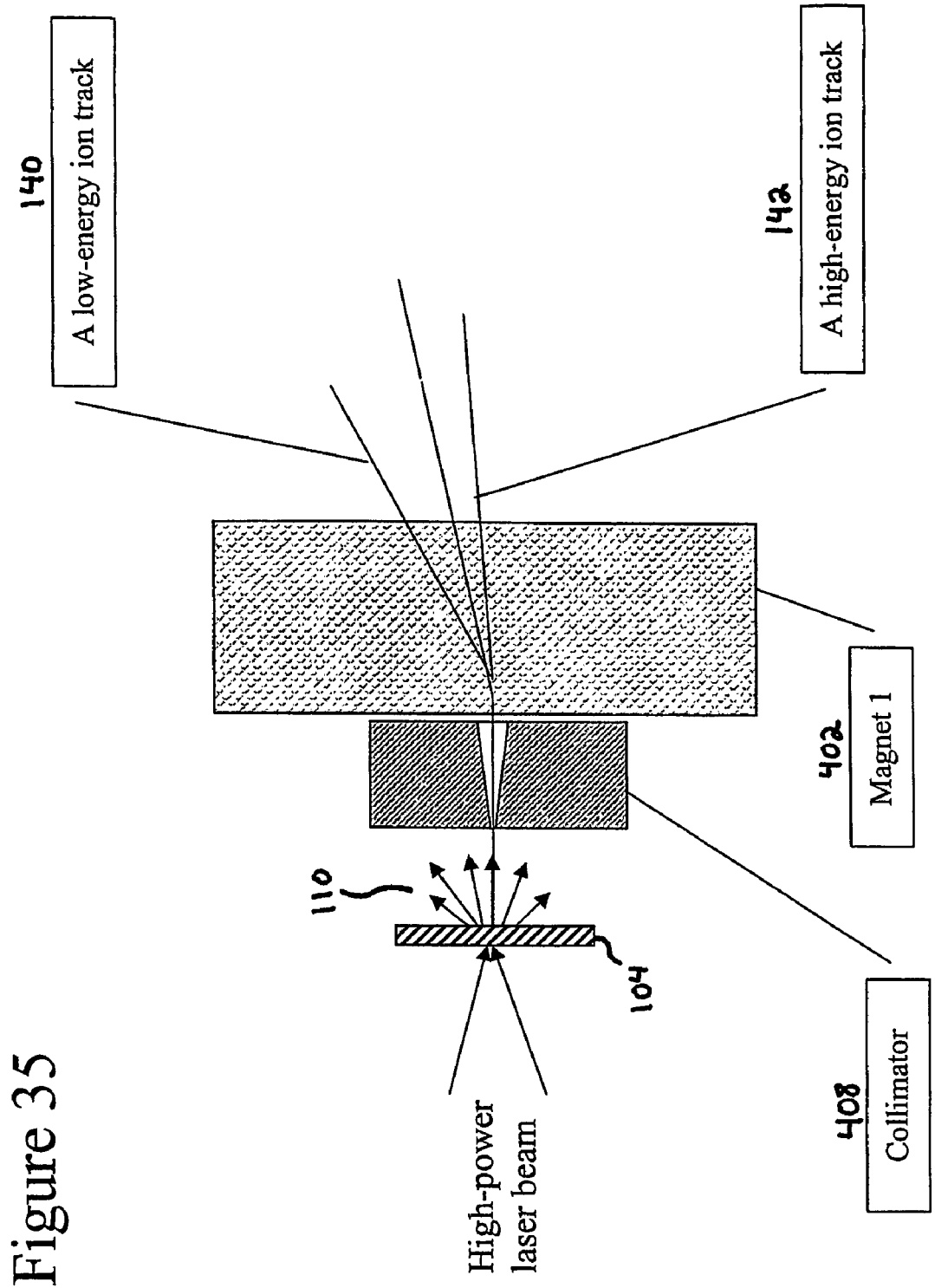
FIG. 35 depicts a sectional view of an embodiment of an ion selection system of the present invention.

FIG. 35 depicts the bending of the trajectories of the positive ions (140, 142) in a direction away from the beam axis of the laser-accelerated high energy polyenergetic ion beam (110) using the first magnetic field (magnet 402).

Figure 36:
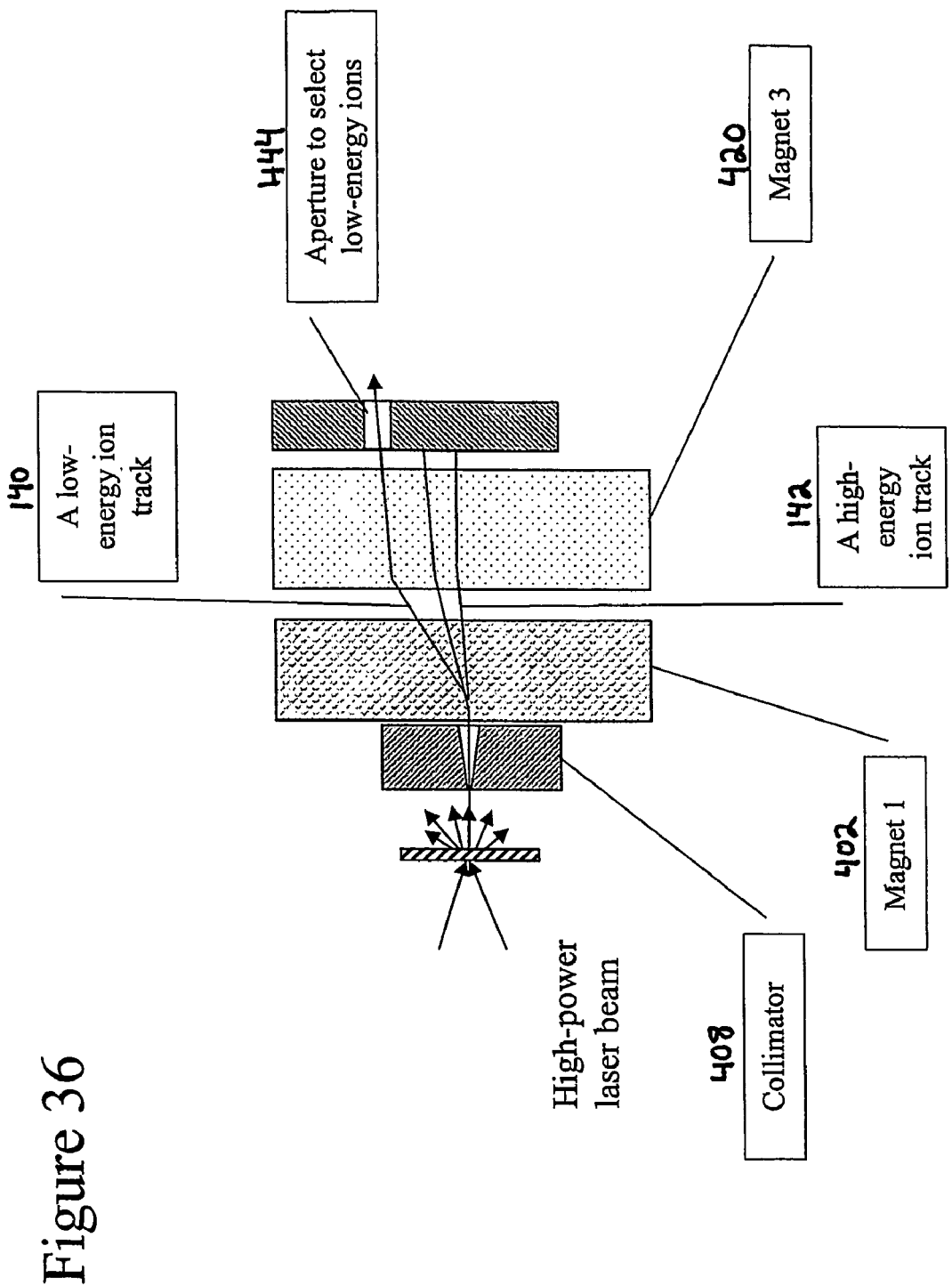
FIG. 36 depicts a sectional view of an embodiment of an ion selection system of the present invention.

FIG. 36 depicts the bending of the trajectories of the spatially separated positive ions (140, 142) in a direction towards aperture (444) using the third magnetic field (magnet 420).

Figure 37:
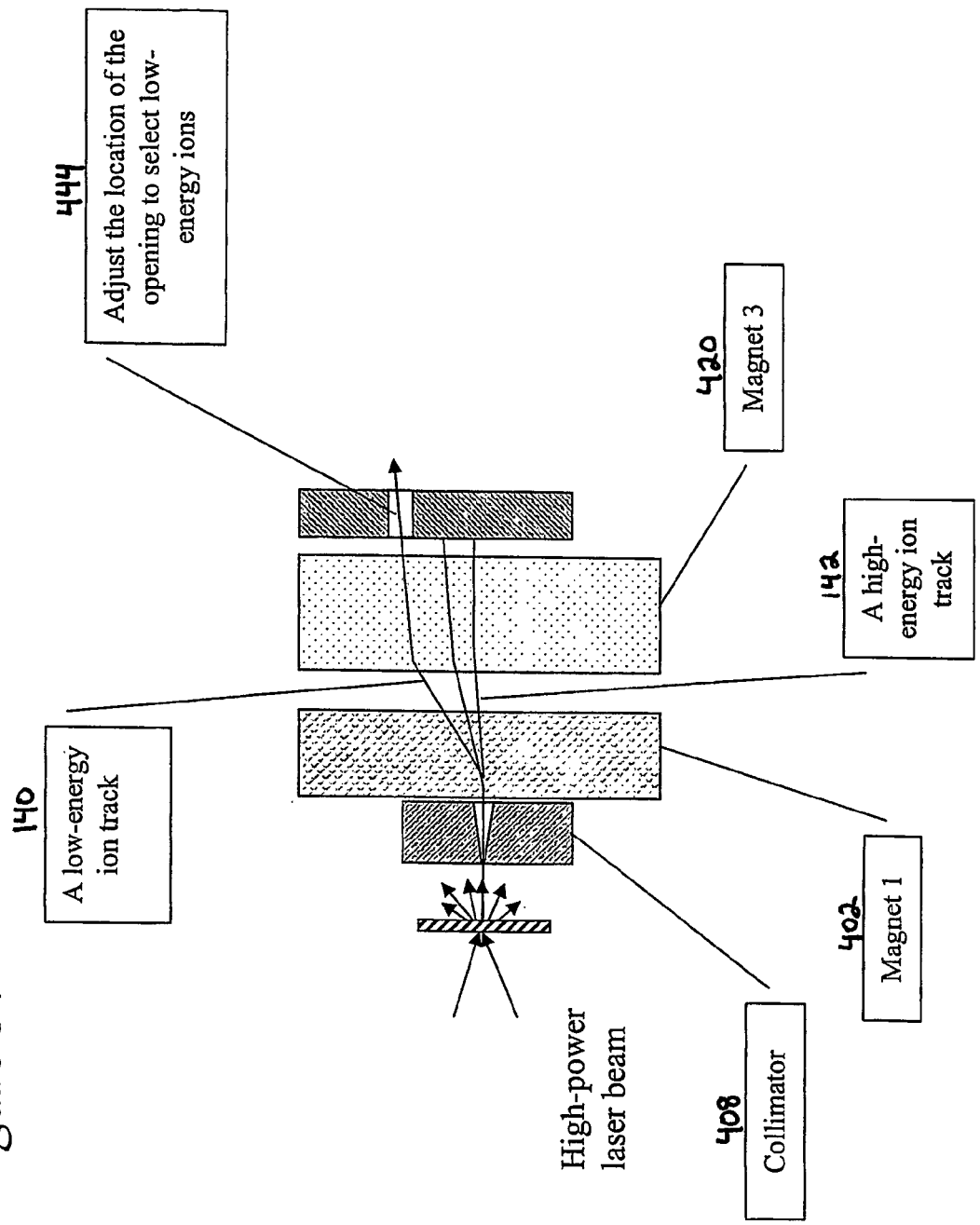
FIG. 37 depicts a sectional view of an embodiment of an ion selection system of the present invention.
Figure 38:
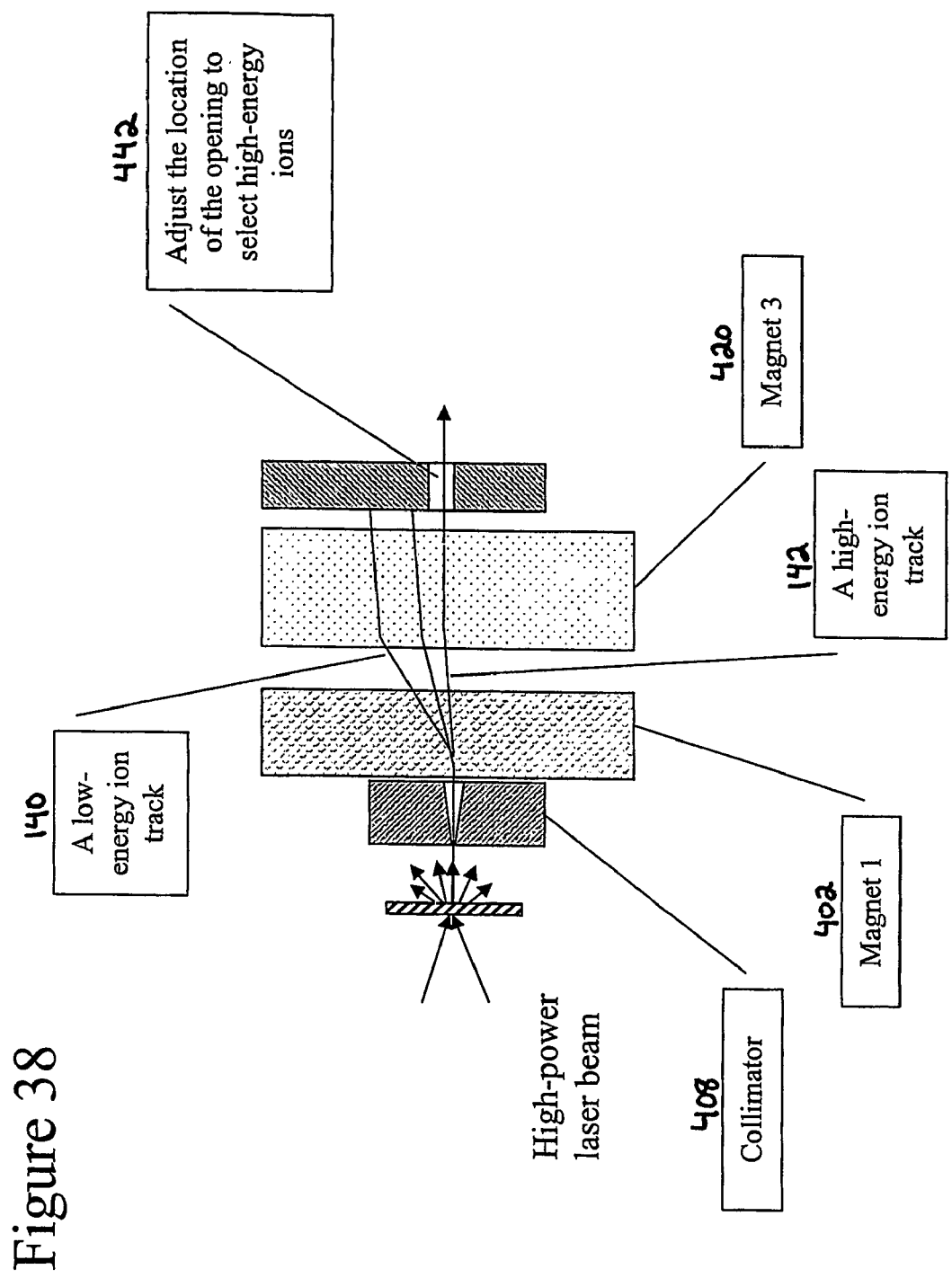
FIG. 38 depicts a sectional view of an embodiment of an ion selection system of the present invention.

FIGS. 37 and 38 depict the spatially separated high energy positive ions being modulated by energy level (low energy (140) and high energy (142), respectively) using a location-controllable opening in aperture (442, 444).

Figure 39:
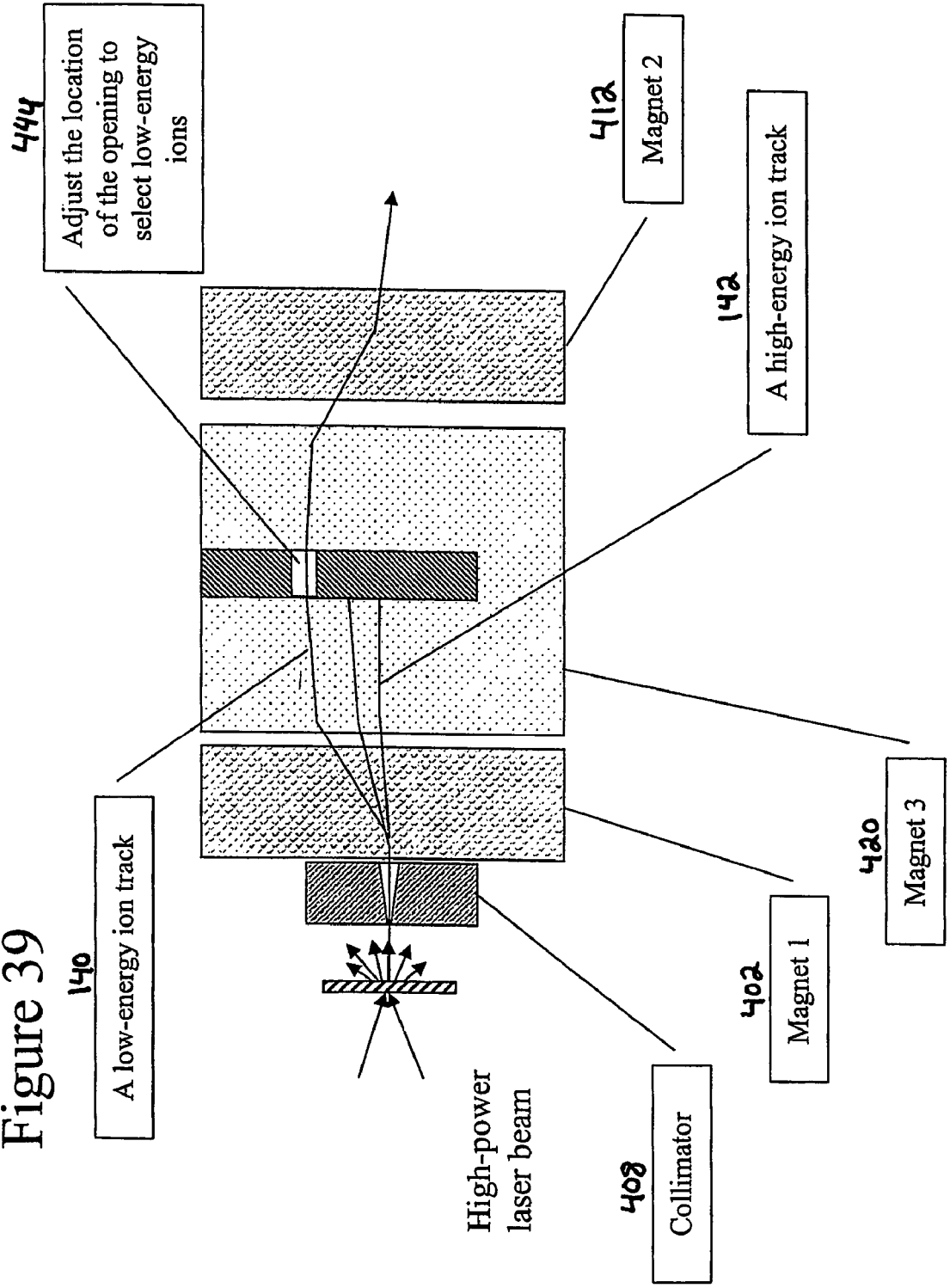
FIG. 39 depicts a sectional view of an embodiment of an ion selection system of the present invention.

FIG. 39 depicts an embodiment of an ion selection system in which the third magnetic field (magnet 420) is capable of bending the selected positive ions towards the second magnetic field (magnet 412), as in FIG. 28.

Figure 40:
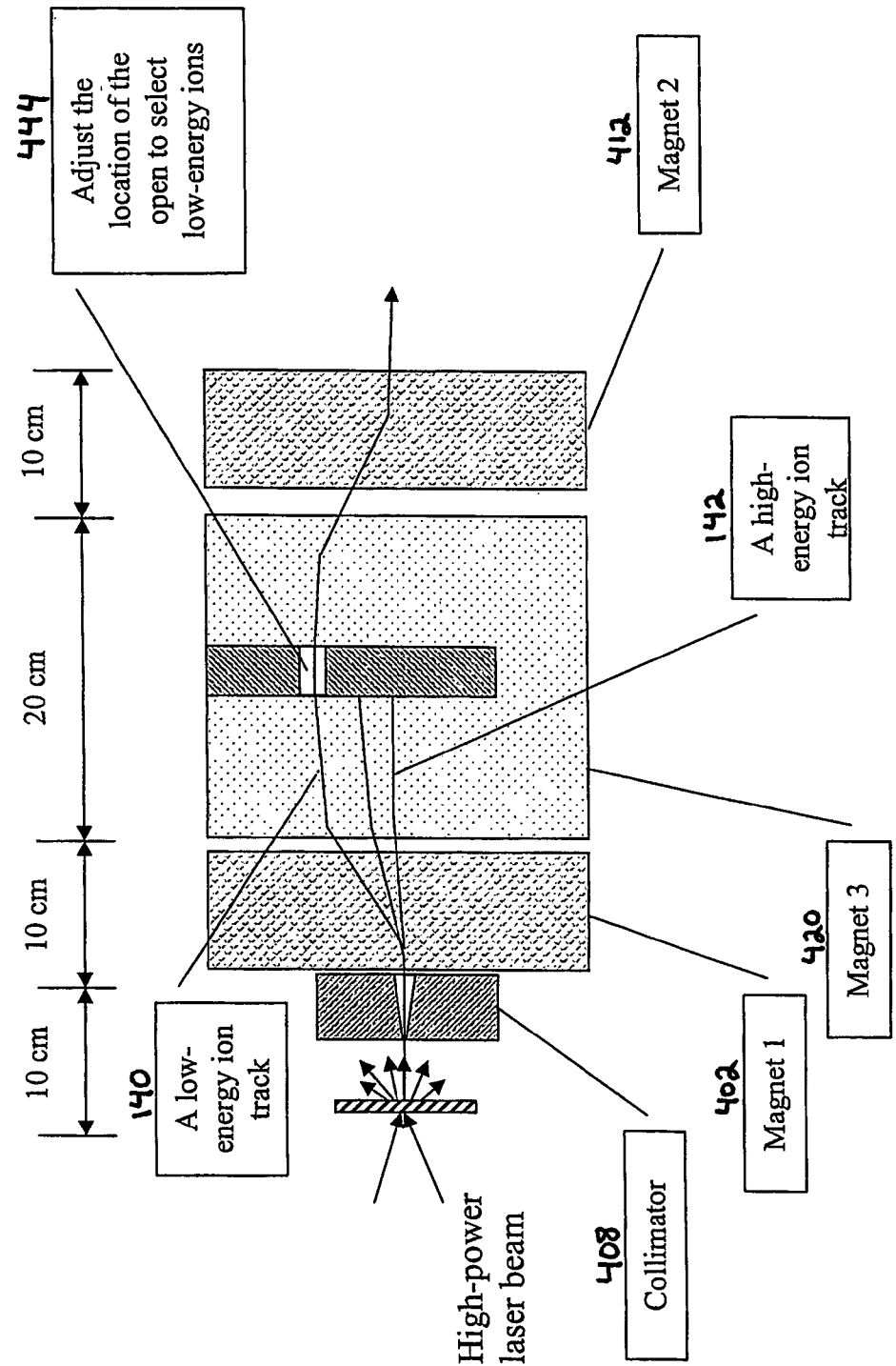
FIG. 40 depicts a sectional view of an embodiment of an ion selection system of the present invention.

FIG. 40 depicts an embodiment of an ion selection system in which the high energy polyenergetic positive ions are spatially separated over distances up to about 50 cm.

Figure 41:
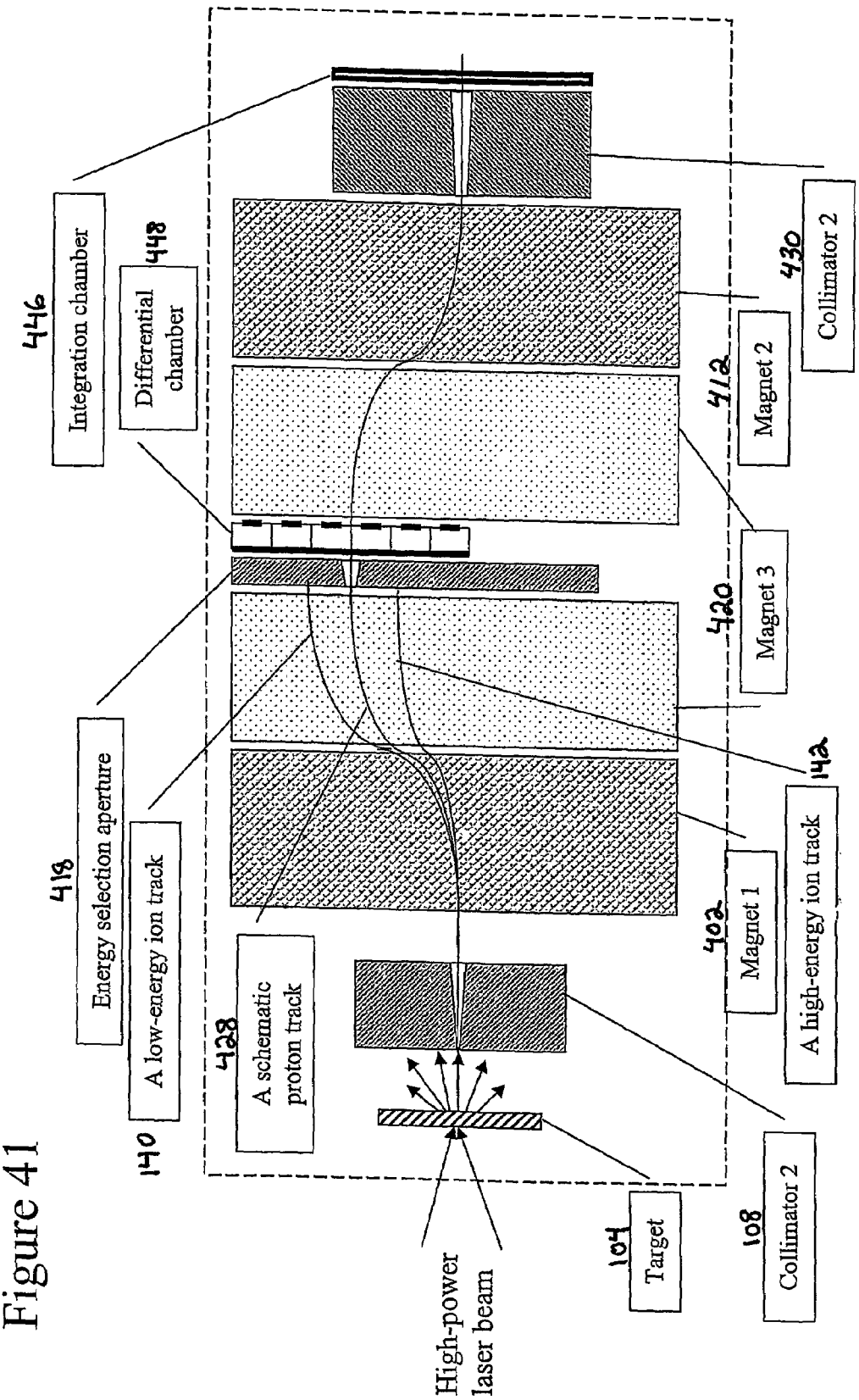
FIG. 41 depicts a sectional view of a laser-accelerated high energy polyenergetic positive ion therapy system of the present invention.

FIG. 41 depicts an embodiment of an ion therapy system that includes a laser-targeting system, the laser-targeting comprising a laser and a targeting system (104) capable of producing a high energy polyenergetic ion beam (110), the high energy polyenergetic ion beam including high energy polyenergetic positive ions having energy levels of at least about 50 MeV. The high energy polyenergetic positive ions are spatially separated (428) based on energy level (140, 142), and an ion selection system capable of producing a therapeutically suitable high energy polyenergetic positive ion beam from a portion of the high energy polyenergetic positive ions is provided. Also provided is a differential chamber (448) and an integration chamber (446). Positive ions of different energies will typically pass through different parts of the differential chamber (448) that measures the differences in energies of the ions, which monitors the energy of the selected ions. Typically, the differential chamber (448) does not control the energy selection aperture, The integration chamber is provided to generate a signal that is analyzed (e.g., by a computer or suitable data processor, not shown) to determine the position of the aperture (418) and the aperture openings.

Figure 42:
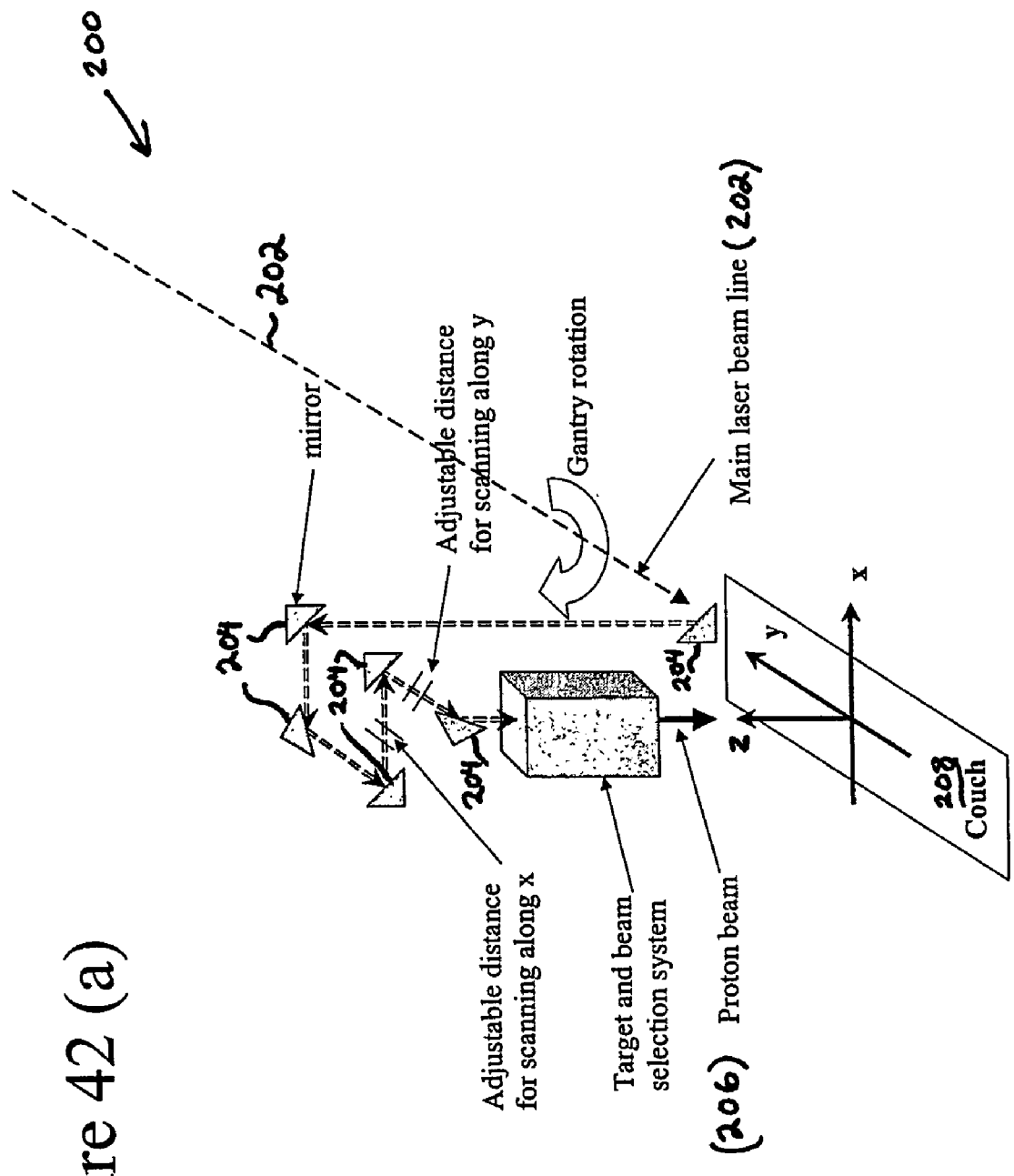
FIG. 42($a$) depicts a perspective view of an embodiment of a laser-accelerated high energy polyenergetic positive ion beam treatment center.
Figure 42:
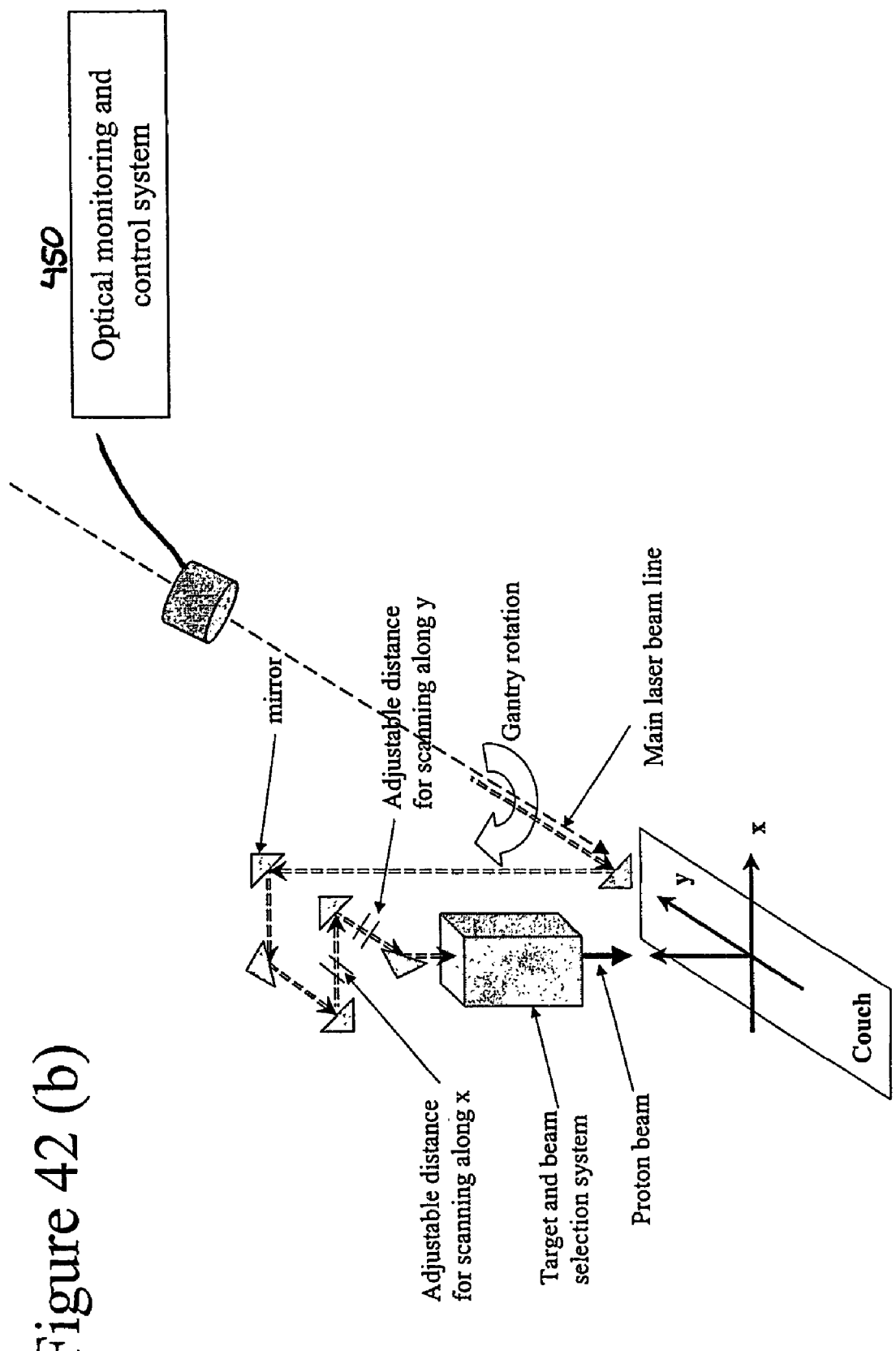
Figure 42C:
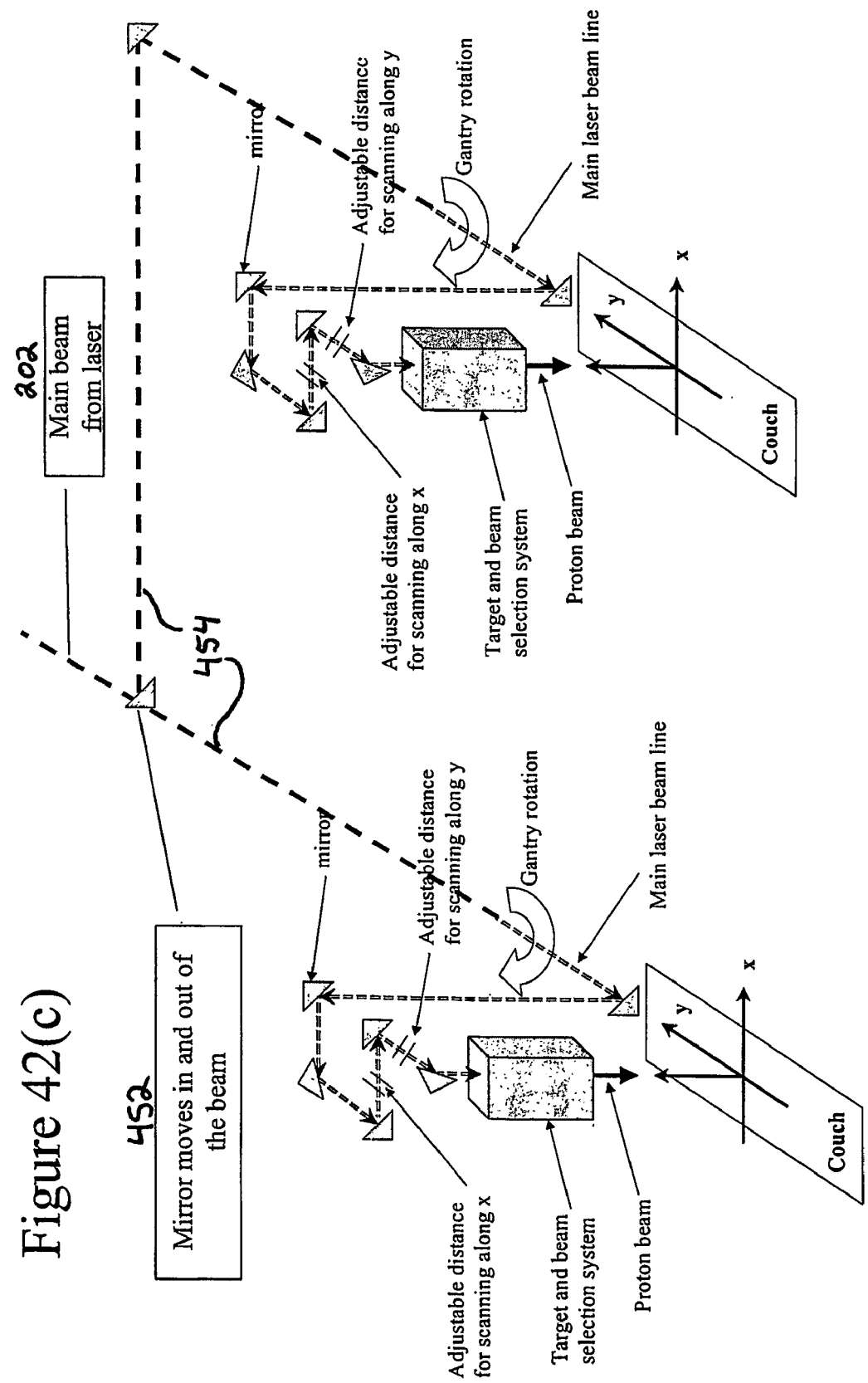
Figure 42D:
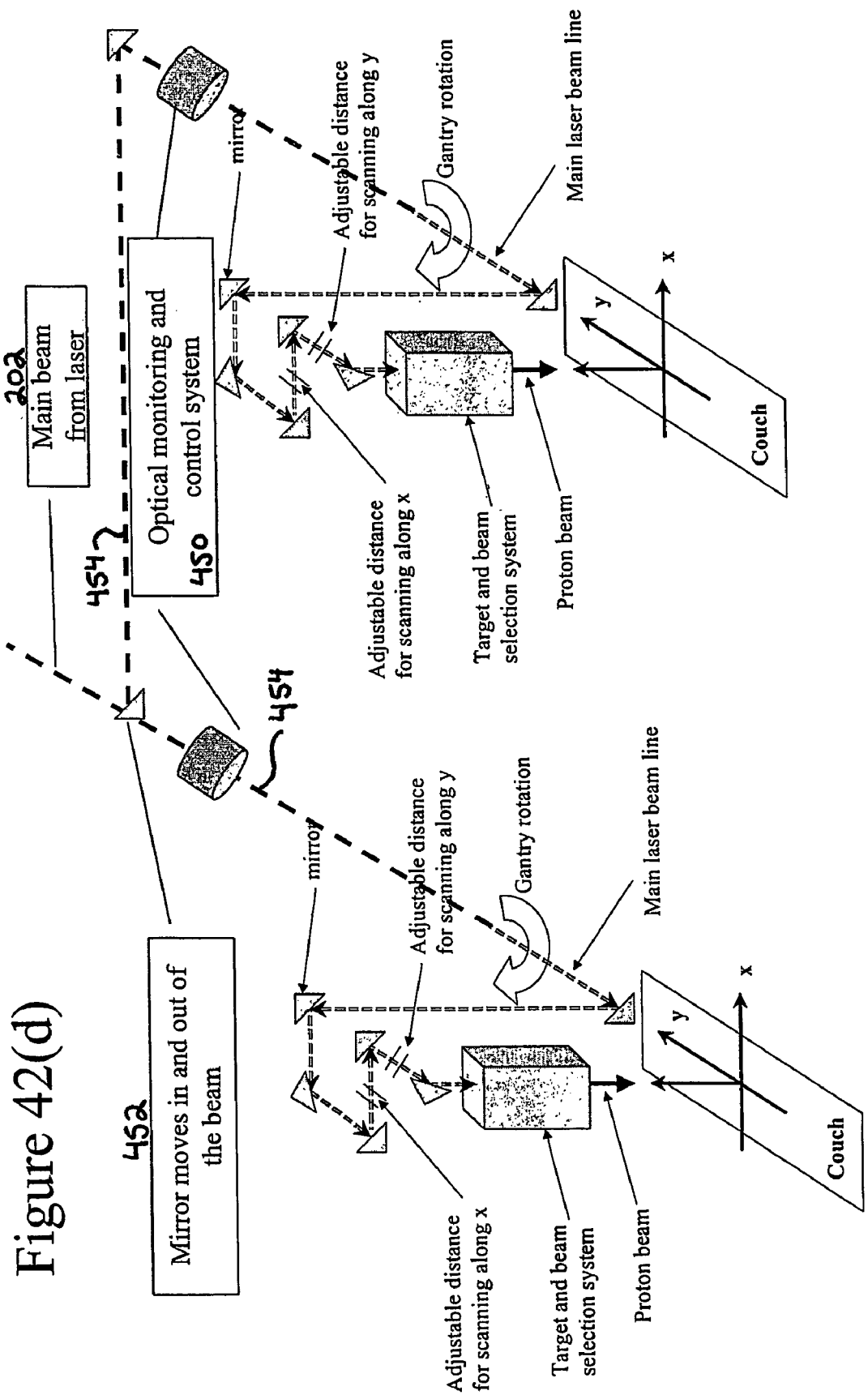

FIGS. 42(a–d) depicts perspective diagrams of a variety of laser-accelerated high energy polyenergetic positive ion beam treatment centers (200), that each suitably include at least one of the ion therapy systems depicted in FIGS. 21–41 and a location for securing a patient (i.e., a couch, 208). For example, FIG. 42(a) depicts a suitable treatment center of the type described above with respect to FIG. 17 in which the laser beam (202) is reflectively transported to the target assembly (100) using a plurality of mirrors (204). FIG. 42(b) depicts a suitable treatment center that includes an optical monitoring and control system (450) for the laser beam (202). FIG. 42(c) depicts a suitable treatment center in which at least one beam splitter or mirror (452) is provided to split the laser beam (202) into split or reflected laser beams 454 to each of at least two target assemblies (100) or to reflect the laser beam to one of the target assemblies (100). Depicted is a suitable treatment center that shows the laser-targeting system having two target assemblies and two ion selection systems each capable of individually producing a therapeutically suitable high energy polyenergetic positive ion beam from each of the individual high energy polyenergetic positive ion beams. An individual polyenergetic ion beam monitoring and control system is also provided for each of the therapeutically suitable high energy polyenergetic positive ion beams. This embodiment depicts a mirror (452) that is capable of being positioned in and out of the main laser beam to direct the beam to one of the ion therapy systems. Alternatively, a beam splitter can be used when a sufficiently powerful laser beam is provided so that split beams can be used simultaneously by two or more ion therapy systems. For providing patient privacy, typical ion therapy centers having two or more ion therapy systems will have an individual treatment room for each of the ion therapy systems. In such embodiments, the laser beam source is suitably located in a separate room or building. FIG. 42(d) depicts an embodiment of the treatment center that further includes an optical monitoring system (450). In this embodiment, the optical monitoring system (450) permits the operator to know, and control, which of the ion therapy systems is being activated.

Figure 43:
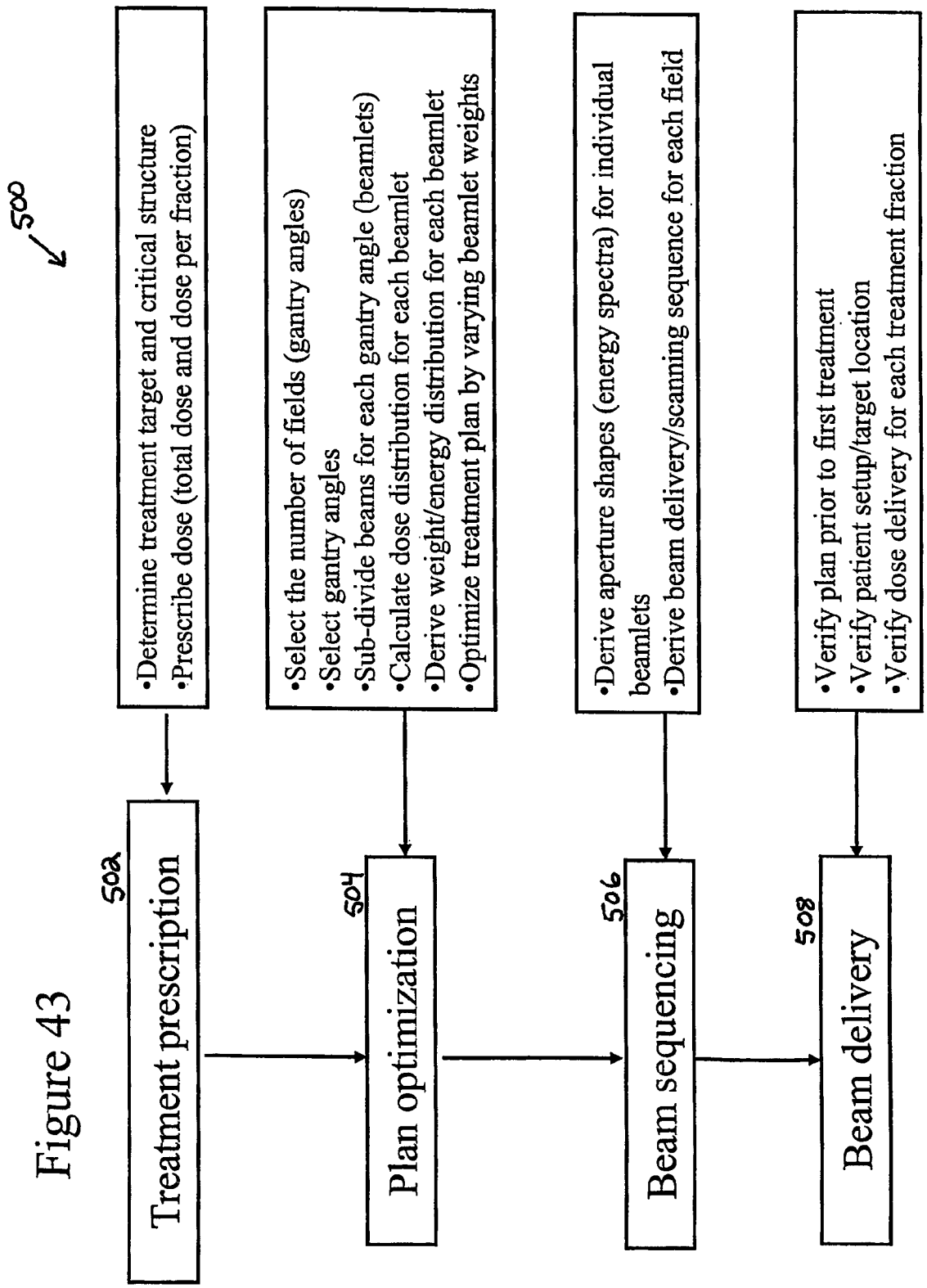
FIG. 43 depicts a flow chart of an embodiment of a method of treating a patient using polyenergetic high energy positive ions.

FIG. 43 is a flow-chart (500) of a method of treating a patient in accordance with the invention. This method includes the steps (502–508) of identifying the position of a targeted region in a patient, determining the treatment strategy of the targeted region, the treatment strategy comprising determining the dose distributions of a plurality of therapeutically suitable high energy polyenergetic positive ion beams for irradiating the targeted region (e.g., determining the energy distribution, intensity and direction of a plurality of therapeutically suitable high energy polyenergetic positive ion beams); forming the plurality of therapeutically suitable high energy polyenergetic positive ion beams from a plurality of high energy polyenergetic positive ions, the high energy polyenergetic positive ions being spatially separated based on energy level; and delivering the plurality of therapeutically suitable polyenergetic positive ion beams to the targeted region according to the treatment strategy.

Thus, methods and systems providing high energy polyenergetic positive ion radiation therapy have been provided.

While the present invention has been described in connection with the exemplary embodiments of the various figures, it is to be understood that other similar embodiments may be used or modifications and additions may be made to the described embodiment for performing the same function of the present invention without deviating therefrom. For example, one skilled in the art will recognize that the present invention as described in the present application may apply to any configuration of magnets, apertures and collimators that selects positive ions based on energy from a source of laser-accelerated high energy polyenergetic positive ions. Therefore, the present invention should not be limited to any single embodiment, but rather should be construed in breadth and scope in accordance with the appended claims.

REFERENCES

M. Austin-Seymour, et al., "Considerations in Fractionated Proton Radiotherapy: Clinical Potential and Results", Radiother. Oncol, 17, 29 (1990).

M. J. Berger (1993), "Proton Monte Carlo transport program PTRAN", NISTIR 5113 (Gaithersburg, Md.: NIST) (1993).

Brahme A., "Optimization of stationary and moving beam radiation therapy techniques", Radiotherapy and Oncology, (1988) 12:129–140.

S. V. Bulanov, V. A. Vshivkov, G. I. Kudnikova, T. Z. Eriskepov, F. Caligano, F. F. Kamenets, T. V. Liseikina, N. M. Naumova, and F. Pegoraro, "Interaction of petawatt laser pulses with underdense plasmas", Plasma Phys. Rep. 25, 701 (1999).

C. Burman, C. S. Chui, G. Kutcher, et al., "Planning delivery, and quality assurance of intensity modulated radiotherapy using dynamic multileaf collimator: A strategy for lasge-scale implementation for the treatment of carcinoma of the prostate", Int J Radiat Oncol Biol Phys 39: 863–73 (1997).

L. Cella, A. Lomax and R. Miralbell, "Potential role of intensity modulated proton beams in prostate cancer radiotherapy", Int. J. Radiation Oncology Biol. Phys. 49: 217–223 (2001).

E. L. Clark, K. Krushelnick, M. Zepf, F. N. Beg, M. Tatarakis, A. Machacek, M. I. K. Santala, I. Wafts, P. A. Norreys, and A. E. Dangor, "Energetic Heavy-Ion and Proton Generation from Ultraintense Laser-Plasma Interactions with Solids", Phys. Rev. Lett. 85: 1654–57 (2000).

F. T. Cole, "Accelerator Considerations in the Design of a Proton Therapy Facility", in Particle Acceleration Corp Rep (1991).

J. Deng, S. B. Jiang, J. S. Li, T. Pawlicki and C.-M. Ma, "Photon beam characterization and modeling for Monte Carlo treatment planning", Phys. Med. Biol. (2000a) 45: 411–27.

J. Deng, S. B. Jiang, T. Pawlicki, J. Li and C.-M. Ma, "Electron beam commissioning for Monte Carlo dose calculation", Phys. Med. Biol. (2000b) submitted.

J. L. Duggan and I. L. Morgan, Eds., "Application of Accelerators in Research and Industry", (AIP Press, New York, 1997), p. 1261.

Fourkal E., Tajima T., Ding M. and Ma C. M., "PIC simulation of laser proton acceleration for radiotherapy", Med. Phys. (2002a) conditionally accepted.

J. B. Flanz, S. G. Bradley, M. Goitein, A. Smith, Y. Jongen, J. Bailey, M. Ladeuze, S. Schmidt, J. Schubert, A. vanMeerbeeck, T. Hurn and R. Junge, "Initial equipment commissioning of the North Proton Therapy Center", Proc. the 1998 Cyclotron conference. (1998).

M. Goosens, S. Giani, S. Ravndal, "*GEANT: detector dexcription and simulation tool*", Technical Report CERN Program Library, long writeup, CERN, Geneva, Switzerland W5013 (1993).

Holmes T. W. and Mackie T. R. "*A comparison of three inverse treatment planning algorithms*" Phys. Med. Biol., 39:91–106, (1994a).

Holmes T. W. and Mackie T. R. "*A filtered backprojection dose calculation method for inverse treatment planning*", Med. Phys, 21:303–313, (1994b).

S. B. Jiang, "*Intensity modulated radiation therapy using compensators*", Ph.D. Thesis, Medical College of Ohio, Toledo, Ohio (1998).

S. B. Jiang, A. Kapur and C.-M. Ma, "*Electron beam modelling and commissioning for Monte Carlo treatment planning*", Med. Phys. 27:180–191 (2000a).

S. B. Jiang, J. Deng, J. S. Li, T. Pawlicki, A. L. Boyer and C.-M. Ma, "*An aperture based optimization method for modulated electron radiotherapy*", Proc. AAPM 2000 Annual Meeting (Chicago, Ill., 2000b) in press.

S. B. Jiang, J. Deng, A. L. Boyer and C.-M. Ma, "*An extrafocal source model for photon beam dose calculation*", Med. Phys. 28: 55–66 (2001).

Y. A. Jongen, et al., "*Proton therapy system for MGH's NPTC: equipment description and progress report, In Cyclotrons and Their Applications*", J. C. Cornell (ed) (New Jersey: World Scintific) 606–609 (1996).

M. H. Key, et al., "*Studies of the Relativistic Electron Source and Related Phenomena in Petawatt Laser Matter Interactions*', in "*First International Conference on Inertial Fusion Sciences and Applications*" (Bordeaux, France, 1999).

R. N. Kjellberg, "*Stereotactic Bragg Peak Proton Radiosurgery for Cerebral Arteriovenous Malformations*", Ann. Clin. Res. 18, Supp. 47,17 (1986).

M. C. Lee and C.-M. Ma, "*Monte Carlo investigation of electron beam dose distributions in a transverse magnetic field*", Phys. Med. Biol. (2000) submitted.

J. S. Li, T. Pawlicki, J. Deng, S. B. Jiang and C.-M. Ma, "*Simulation of beam modifiers for Monte Carlo treatment planning*", Proc. ICCR XIIIth (Heldelberg, Germany, 2000) 437–39.

C.-M. Ma, B. A. Faddegon, D. W. O. Rogers and T. R. Mackie, "*Accurate characterization of Monte-Carlo calculated electron beams for radiotherapy*", Med. Phys. 24 (1997) 401–416 (1997).

C.-M. Ma, "*Characterization of computer simulated radiotherapy beams for Monte Carlo treatment planning*", Radiation Phys. Chemistry 53 (1998) 329–44 (1998).

C.-M. Ma, "*A compact laser-proton radiotherapy system*", Int. Report SU-RADONC-PHYS-0006, Stanford University School of Medicine, Stanford, Calif. (2000).

C.-M. Ma, J. S. Li, T. Pawlicki, S. B. Jiang, Deng, S. Brain and A. L. Boyer, "*A Monte Carlo dose calculation tool for radiotherapy treatment planning*", Med. Phys. 26, 1084. (1999a).

C.-M. Ma, E. Mok, A. Kapur, D. Findley, S. Brain, K. Forster and A. L. Boyer, "*Clinical implementation of a Monte Carlo treatment planning system*", Med. Phys. 26:2133–43 (1999b).

C.-M. Ma and S. B. Jiang, "*Monte Carlo modelling of electron accelerators*", Phys. Med. Biol., 44: R167–212 (1999).

C.-M. Ma, *A compact laser-proton radiotherapy system*, Internal Report, SU-RADONC-PHYS-0006, Stanford University School of Medicine, Stanford, Calif. (2000).

C.-M. Ma, T. Pawlicki, S. B. Jiang, E. Mok, A. Kapur, L. Xing, L. Ma and A. L. Boyer, *Monte Carlo verification of IMRT dose distributions from a commercial treatment planning optimization system*, Phys. Med. Biol., 45:2483–95 (2000a).

C.-M. Ma, T. Pawlicki, M. C. Lee, S. B. Jiang, J. S. Li, J. Deng, E. Mok, B. Yi, G. Luxton & A. L. Boyer, *Energy- and intensity-modulated electron beam radiotherapy for breast cancer*, Phys. Med. Biol. 45: 2293–2311 (2000b).

C.-M. Ma, J. S. Li, T. Pawlicki, S. B. Jiang and J. Deng, *MCDOSE—a Monte Carlo dose calculation tool for radiotherapy treatment planning*, Proc. ICCR XIIIth (Hiedelberg, Germany, 123–25 (2000c).

C.-M. Ma, T. Tajima, B. Shahine, M. C. Lee, T. Guerrero and A. L. Boyer, *Laser-accelerated proton beams for radiation therapy*, AAPM 2001 Annual Meeting (Salt Lake City) (2001).

C.-M. Ma, T. Pawlicki, M. C. Lee, S. B. Jiang, J. S. Li, J. Deng, and A. L. Boyer (2001b), *Electron beam modulation with transverse magnetic fields for radiation therapy*, AAPM 2001 Annual Meeting (Salt Lake City) submitted.

Maximchuck, S. Gu, K. Flippo, and D. Umstadter, V. Yu. Bychenkov., *Forward Ion Acceleration in Thin Films Driven by a High-Intensity Laser*, Phys. Rev. Lett 84 4108–4111 (2000).

M. F. Moyers, D. W. Miller, J. V. Siebers, R. Galindo, S. Sun, M. Sardesai and L. Chan, *Water equivalence of various materials for 155 to 250 MeV protons*, (abstract) Med. Phys. 19:892 (1992).

T. A. Pawlicki, S. B. Jiang, J. Deng, J. S. Li and C.-M. Ma, "*Monte Carlo calculated beamlets for photon beam inverse planninig*", Med. Phys. 26: 1064–65 (1999).

Rau and T. Tajima, '*Strongly nonlinear magnetosonic waves and ion acceleration*', Phys. Plasma 5, 3575 (1998).

F. Salvat, J. M. Fernandez-Vera, J. Baro and J. Sempau, *PENELOPE, An Algorithm and Computer Code For Monte Carlo Simulation of Electron-Photon Showers* (Spain: Informes Tecnicos Ciemat) (1996).

J. M. Seddon, '*Relative Survival Rates after Alternative Therapies for Uveal Melanoma*', Ophtalmol. 97, 769(1990).

Shahine, M. C. Lee, J. S. Li, J. Deng, T. Guerrero, A. L. Boyer and C-M. Ma, *Monte Carlo dose calculation for energy- and intensity-modulated proton therapy*, AAPM 2001 Annual Meeting (Salt Lake City) submitted.

J. M. Sisterson, '*Clinical Use of Protons and Ion Beams from a Worldwide Perspective*', Nucl. Instr. Methods B40, 1350 (1989).

J. M. Sisterson, "*Proton Therapy in 1996*".

J. M. Sisterson, *World wide charged particles patient totals*, Particles, 23, 1 (1999).

J. D. Slater, L. T. Yonemoto, C. J. Rossi, et al. *Conformal proton therapy for prostate carcinoma*, Int J Radiat Oncol Biol Phys 42: 299–304 (1998).

R. A. Snavely, et al., *Intense high energy proton beams from Petawatt Laser irradiation of solids*, Phys. Rev. Lett. 85:2945–48 (2000)

Strickland, G. Mourou, Opt. Comm. 56, 219 (1985)

T. Tajima, '*Compact Laser Proton Accelerator beyond 100 MeV for Medicine*', (LLNL, Livermore, 1999).

T. Tajima, "*Computational Plasma Physics*", (Addison-Wesley, Reading, Mass., 1989).

T. Tajima and J. M. Dawson, '*Laser electron accelerator*', Phys. Rev. Lett. 43, 267 (1979).

T. Tajima, K. Mima, and H. Baldis, Eds. "*High Field Science*" (Plenum, New York, 2000).

Y. Ueshima, Y. Sentoku, Y. Kishimoto, and T. Tajima, '*Simulation on interaction of a relativistically intense short*

*pulse laser with solid thin film'*, in Proc. JIFT Workshop, K. Mima and T. Tajima, Eds. (JIFT, Tokai, 1999).

Umstadter, S. Y. Chen, A. Maksimchuk, G. Mourou, and G. Mourou, *'Nonlinear Optics in Relativistic Plasmas and Laser Wakefield Acceleration of Electrons'*, Science 273, 472(1996).

D. Umstadter, S. Y. Chen, A. Maksimchuk, G. Mourou, and R. Wagner, Science 273, 606 (1996).

L. J. Verhey and J. E. Munzenrider, *Proton beam therapy*, Ann Rev. Biophys. Bioeng. 11:331–57 (1982).

Webb S., *Optimization of conformal radiotherapy dose distributions by simulated annealing.* Phys. Med. Biol., 34:1349–1370 (1990).

Webb S. *Optimizing the planning of intensity-modulated radiotherapy.* Phys. Med. Biol., 39:2229–2246 (1994).

S. C. Wilks, W. L. Kruer, T. Cowan, S. Hatchett, M. Key, A. B. Langdon, B. Lasinski, A. McKinnon, P. Patel, T. Phillips, M. Roth, P. Springer, R. Snavely, Bull. Amer. Phys. Soc. 44, 229 (1999).

Xing L and Chen G. T. Y. *Iterative methods for inverse treatment planning.* Phys. Med. Biol, 41:2107–2123, (1996).

What is claimed:

1. An ion selection system, comprising:
    a collimation device capable of collimating a laser-accelerated high energy polyenergetic ion beam, said laser-accelerated high energy polyenergetic ion beam comprising a plurality of high energy polyenergetic positive ions;
    a first magnetic field source capable of spatially separating said high energy polyenergetic positive ions according to their energy levels;
    an aperture capable of modulating the spatially separated high energy polyenergetic positive ions; and
    a second magnetic field source capable of recombining the modulated high energy polyenergetic positive ions.

2. The ion selection system of claim 1, wherein the modulated high energy polyenergetic positive ions have energy levels in the range of from about 50 MeV to about 250 MeV.

3. The ion selection system of claim 1, wherein said first magnetic field source is capable of bending the trajectories of the high energy polyenergetic positive ions away from a beam axis of said laser-accelerated polyenergetic ion beam.

4. The ion selection system of claim 3, further comprising a third magnetic field source, said third magnetic field source capable of bending the trajectories of the spatially separated high energy polyenergetic positive ions towards the aperture.

5. The ion selection system of claim 4, wherein the aperture is placed outside of the magnetic field of said third magnetic field.

6. The ion selection system of claim 4, wherein the magnetic field of said third magnetic field source is capable of bending the trajectories of the modulated high energy polyenergetic positive ions towards the second magnetic field source.

7. The ion selection system of claim 6, wherein the second magnetic field source is capable of bending the trajectories of the modulated high energy polyenergetic positive ions towards a direction parallel to the direction of the laser-accelerated high energy polyenergetic ion beam.

8. The ion selection system of claim 1, further comprising a secondary collimation device capable of fluidically communicating a portion of the recombined high energy polyenergetic positive ions therethrough.

9. The ion selection system of claim 8, wherein said secondary collimation device is capable of modulating the beam shape of the recombined high energy polyenergetic positive ions.

10. The ion selection system of claim 1, wherein said aperture comprises a plurality of openings, each of the openings capable of fluidically communicating high energy polyenergetic positive ions therethrough.

11. The ion selection system of claim 10, wherein the aperture is a multileaf collimator.

12. A method of forming a high energy polyenergetic positive ion beam, comprising:
    forming a laser-accelerated high energy polyenergetic ion beam comprising a plurality of high energy polyenergetic positive ions, said high energy polyenergetic positive ions characterized as having a distribution of energy levels;
    collimating said laser-accelerated ion beam using a collimation device;
    spatially separating said high energy positive ions according to their energy levels using a first magnetic field;
    modulating the spatially separated high energy polyenergetic positive ions using an aperture; and
    recombining the modulated high energy polyenergetic positive ions using a second magnetic field.

13. The method according to claim 12, wherein the step of modulating the spatially separated high energy polyenergetic positive ions gives rise to a portion of the positive ions being transmitted through the aperture, said portion of the positive ions having energy levels in the range of from about 50 MeV to about 250 MeV.

14. The method according to claim 12, wherein said trajectories of the high energy polyenergetic positive ions are bent away from a beam axis of said laser-accelerated high energy polyenergetic ion beam using said first magnetic field.

15. The method according to claim 14, wherein the trajectories of the spatially separated high energy polyenergetic positive ions are further bent towards the aperture using a third magnetic field.

16. The method according to claim 15, wherein the spatially separated high energy positive ions are modulated by energy level using a plurality of controllable openings in said aperture.

17. The method according to claim 15, wherein the third magnetic field further bends said trajectories towards the second magnetic field.

18. The method according to claim 17, wherein the second magnetic field bends said trajectories towards a direction parallel to the direction of a laser-accelerated high energy polyenergetic ion beam.

19. The method according to claim 12, wherein a portion of the recombined high energy polyenergetic positive ions is fluidically communicated through a secondary collimation device.

20. The method according to claim 12, wherein a plurality of high energy polyenergetic positive ion beamlets are fluidically communicated through a plurality of controllable openings in said aperture to modulate the spatially separated high energy positive ions.

21. The method according to claim 12, wherein the high energy polyenergetic positive ions are spatially separated over distances up to about 50 cm according to an energy distribution of the high energy polyenergetic positive ions, said distances being measured perpendicularly to a beam axis of said laser-accelerated ion beam entering the first magnetic field.

22. The method of claim 12, further comprising irradiating a radioisotope precursor with the recombined spatially separated high energy polyenergetic positive ions.

23. A laser-accelerated high energy polyenergetic positive ion therapy system, comprising:
    a laser-targeting system, said laser-targeting comprising a laser and a targeting system capable of producing a high energy polyenergetic ion beam, said high energy polyenergetic ion beam comprising high energy polyenergetic positive ions having energy levels of at least about 50 MeV, the high energy polyenergetic positive ions being spatially separated based on energy level;
    an ion selection system capable of producing a therapeutically suitable high energy polyenergetic positive ion beam from a portion of said high energy polyenergetic positive ions; and
    an ion beam monitoring and control system.

24. The laser-accelerated high energy polyenergetic positive ion therapy system of claim 23, wherein the ion selection system comprises:
    a collimation device capable of collimating said laser-accelerated high energy polyenergetic ion beam;
    a first magnetic field source capable of spatially separating said high energy polyenergetic positive ions according to their energy levels;
    an aperture capable of modulating the spatially separated high energy polyenergetic positive ions; and
    a second magnetic field source capable of recombining the modulated high energy polyenergetic positive ions.

25. The laser-accelerated high energy polyenergetic positive ion therapy system of claim 24, wherein the modulated high energy polyenergetic positive ions are characterized as having energy levels in the range of from about 50 MeV to about 250 MeV.

26. The laser-accelerated high energy polyenergetic positive ion therapy system of claim 24, wherein said first magnetic field source provides a first magnetic field, said first magnetic field capable of bending the trajectories of the high energy polyenergetic positive ions, said bending being in a direction away from a beam axis of said laser-accelerated high energy polyenergetic ion beam.

27. The laser-accelerated high energy polyenergetic positive ion therapy system of claim 26, wherein the ion selection system further comprises a third magnetic field source, said third magnetic field source capable of bending the trajectories of the spatially separated high energy polyenergetic positive ions towards the aperture.

28. The laser-accelerated high energy polyenergetic positive ion therapy system of claim 27, wherein the aperture is placed outside of the magnetic field of said third magnetic field.

29. The laser-accelerated high energy polyenergetic positive ion therapy system of claim 27, wherein the magnetic field of said third magnetic field source is capable of bending the trajectories of said portion of the spatially separated high energy polyenergetic positive ions towards the second magnetic field source.

30. The laser-accelerated high energy polyenergetic positive ion therapy system of claim 29, wherein the second magnetic field source is capable of bending the trajectories of said portion of the spatially separated high energy polyenergetic positive ions towards a direction parallel to a beam axis of the laser-accelerated high energy polyenergetic ion beam.

31. The laser-accelerated high energy polyenergetic positive ion therapy system of claim 24, further comprising a secondary collimation device capable of fluidically communicating a portion of the recombined high energy polyenergetic positive ions therethrough.

32. The laser-accelerated high energy polyenergetic positive ion therapy system of claim 31, wherein the secondary collimation device is capable of modulating a beam shape of the recombined high energy polyenergetic positive ions.

33. The laser-accelerated high energy polyenergetic positive ion therapy system of claim 24, wherein said aperture comprises a plurality of openings, each of the openings capable of fluidically communicating ion beamlets therethrough.

34. A method of treating a patient with a laser-accelerated high energy polyenergetic positive ion therapy system, comprising:
    identifying the position of a targeted region in a patient;
    determining the treatment strategy of the targeted region, said treatment strategy comprising determining the dose distributions of a plurality of therapeutically suitable high energy polyenergetic positive ion beams for irradiating the targeted region;
    forming said plurality of therapeutically suitable high energy polyenergetic positive ion beams from a plurality of high energy polyenergetic positive ions, the high energy polyenergetic positive ions being spatially separated based on energy level; and
    delivering the plurality of therapeutically suitable polyenergetic positive ion beams to the targeted region according to the treatment strategy.

35. The method of treating a patient according to claim 34, wherein determining the dose distributions comprises determining the energy distribution, intensity and direction of a plurality of therapeutically suitable high energy polyenergetic positive ion beams.

36. The method of treating a patient according to claim 34, wherein said therapeutically suitable polyenergetic positive ion beams are prepared by:
    forming a laser-accelerated high energy polyenergetic ion beam comprising high energy polyenergetic positive ions;
    collimating said laser-accelerated high energy polyenergetic ion beam using at least one collimation device;
    spatially separating said high energy polyenergetic positive ions according to their energy levels using a first magnetic field;
    modulating the spatially separated high energy polyenergetic positive ions using an aperture; and
    recombining the modulated high energy polyenergetic positive ions using a second magnetic field.

37. The method of treating a patient according to claim 36, wherein the modulated high energy polyenergetic positive ions have energy levels in the range of from about 50 MeV to about 250 MeV.

38. The method of treating a patient according to claim 36, wherein the trajectories of the high energy polyenergetic positive ions are bent away from a beam axis of said laser-accelerated high energy polyenergetic ion beam using said first magnetic field.

39. The method of treating a patient according to claim 38, wherein the trajectories of the spatially separated high energy polyenergetic positive ions are bent towards the aperture using a third magnetic field.

40. The method of treating a patient according to claim 39, wherein the spatially separated high energy polyenergetic positive ions are modulated by energy level using a plurality of controllable openings in said aperture.

41. The method of treating a patient according to claim 40, wherein the trajectories of the modulated high energy polyenergetic positive ions are further bent towards the second magnetic field using said third magnetic field.

42. The method of treating a patient according to claim 41, wherein the trajectories of the modulated high energy polyenergetic positive ions are bent towards a direction parallel to the direction of a beam axis of the laser-accelerated high energy polyenergetic ion beam using said second magnetic field.

43. The method of treating a patient according to claim 36, wherein a portion of the recombined high energy polyenergetic positive ions are fluidically communicated through a secondary collimation device.

44. The method of treating a patient according to claim 43, wherein the beam shape of the recombined high energy polyenergetic positive ions is modulated by the secondary collimation device.

45. A laser-accelerated high energy polyenergetic positive ion beam treatment center, comprising:
  a location for securing a patient; and
  a laser-accelerated high energy polyenergetic positive ion therapy system capable of delivering a therapeutically suitable high energy polyenergetic positive ion beam to a patient at said location, the ion therapy system comprising:
    a laser-targeting system, said laser-targeting system comprising a laser and a target assembly capable of producing a high energy polyenergetic ion beam, said high energy polyenergetic ion beam comprising high energy polyenergetic positive ions having energy levels of at least about 50 MeV;
    an ion selection system capable of producing a therapeutically suitable high energy polyenergetic positive ion beam using said high energy polyenergetic positive ions, the high energy polyenergetic positive ions being spatially separated based on energy level; and
    a monitoring and control system for said therapeutically suitable high energy polyenergetic positive ion beam.

46. The laser-accelerated high energy polyenergetic positive ion beam treatment center of claim 45, wherein the ion selection system comprises:
  a collimation device capable of collimating said high energy polyenergetic ion beam;
  a first magnetic field source capable of spatially separating said high energy polyenergetic positive ions according to their energy levels;
  an aperture capable of modulating the spatially separated high energy polyenergetic positive ions; and
  a second magnetic field source capable of recombining the modulated high energy polyenergetic positive ions into said therapeutically suitable high energy polyenergetic positive ion beam.

47. The laser-accelerated high energy polyenergetic positive ion beam treatment center of claim 46, wherein the modulated high energy polyenergetic positive ions are characterized as having energy levels in the range of from about 50 MeV to about 250 MeV.

48. The laser-accelerated high energy polyenergetic positive ion beam treatment center of claim 46, wherein said first magnetic field source is capable of bending the trajectories of the high energy polyenergetic positive ions away from a beam axis of said laser-accelerated polyenergetic ion beam entering the first magnetic field.

49. The laser-accelerated high energy polyenergetic positive ion beam treatment center of claim 48, wherein the ion selection system further comprises a third magnetic field source capable of bending the trajectories of the spatially separated high energy polyenergetic positive ions towards the aperture.

50. The laser-accelerated high energy polyenergetic positive ion beam treatment center of claim 49, wherein the aperture is placed outside of the magnetic field of said third magnetic field.

51. The laser-accelerated high energy polyenergetic positive ion beam treatment center of claim 49, wherein the magnetic field of said third magnetic field source is capable of bending the trajectories of the modulated high energy positive ions towards the second magnetic field source.

52. The laser-accelerated high energy polyenergetic positive ion beam treatment center of claim 51, wherein the second magnetic field source is capable of bending the trajectories of the modulated high energy polyenergetic positive ions towards a direction parallel to a beam axis of the laser-accelerated high energy polyenergetic ion beam.

53. The laser-accelerated high energy polyenergetic positive ion beam treatment center of claim 48, further comprising a secondary collimation device capable of fluidically communicating a portion of the recombined high energy polyenergetic positive ions therethrough.

54. The laser-accelerated high energy polyenergetic positive ion beam treatment center of claim 46, wherein said aperture comprises a plurality of openings, each of the openings capable of fluidically communicating ion beamlets therethrough.

55. The laser-accelerated high energy polyenergetic positive ion beam treatment center of claim 45, wherein the target assembly and the ion selection system are placed on a rotating gantry.

56. The laser-accelerated high energy polyenergetic positive ion beam treatment center of claim 45, wherein a laser beam of said laser is reflectively transported to the target assembly using a plurality of mirrors.

57. The laser-accelerated high energy polyenergetic positive ion beam treatment center of claim 56, wherein the ion selection system is robotically mounted to give permit scanning of the therapeutically suitable high energy polyenergetic positive ion beam.

58. The laser-accelerated high energy polyenergetic positive ion beam treatment center of claim 56, further comprising at least one beam splitter to split the laser beam to each of at least two target assemblies.

59. The laser-accelerated high energy polyenergetic positive ion beam treatment center of claim 45, wherein the laser-targeting system comprises a plurality of target assemblies, each of said target assemblies capable of producing a high energy polyenergetic positive ion beam, said high energy polyenergetic positive ion beam comprising high energy polyenergetic positive ions comprising energy levels of at least about 50 MeV;
  a plurality of ion selection systems each capable of individually producing a therapeutically suitable high energy polyenergetic positive ion beam from each of said individual high energy polyenergetic positive ion beams; and
  an individual polyenergetic ion beam monitoring and control system for each of said therapeutically suitable high energy polyenergetic positive ion beams.

60. A method of producing radioisotopes, comprising:
  forming a high energy polyenergetic positive ion beam, comprising:
    forming a laser-accelerated high energy polyenergetic ion beam comprising a plurality of high energy polyenergetic positive ions, said high energy positive ions characterized as having an energy distribution;

collimating said laser-accelerated ion beam using at least one collimation device;

spatially separating said high energy polyenergetic positive ions according to energy using a first magnetic field;

modulating the spatially separated high energy polyenergetic positive ions using an aperture; and recombining the spatially separated high energy polyenergetic positive ions using a second magnetic field; and irradiating a radioisotope precursor with the recombined spatially separated high energy polyenergetic positive ions.

* * * * *